(12) United States Patent
Fanton et al.

(10) Patent No.: US 8,721,650 B2
(45) Date of Patent: May 13, 2014

(54) BONE ANCHOR INSTALLER AND METHOD OF USE

(75) Inventors: Gary S. Fanton, Portola Valley, CA (US); John Krumme, Woodside, CA (US)

(73) Assignee: Tornier, Inc., Bloomington, MN (US)

( * ) Notice: Subject to any disclaimer, the term of this patent is extended or adjusted under 35 U.S.C. 154(b) by 1740 days.

(21) Appl. No.: 11/726,736

(22) Filed: Mar. 22, 2007

(65) Prior Publication Data

US 2007/0260259 A1 Nov. 8, 2007

Related U.S. Application Data

(60) Provisional application No. 60/784,679, filed on Mar. 22, 2006.

(51) Int. Cl.
*A61B 17/56* (2006.01)
(52) U.S. Cl.
USPC ............................................ 606/99; 606/232
(58) Field of Classification Search
USPC ................................ 606/99, 232, 104; 81/453
See application file for complete search history.

(56) References Cited

U.S. PATENT DOCUMENTS

| | | | |
|---|---|---|---|
| 1,562,543 A * | 11/1925 | Cox ................................. | 81/453 |
| 3,527,223 A | 9/1970 | Shein | |
| 3,716,058 A | 2/1973 | Tanner, Jr. | |
| 4,170,990 A | 10/1979 | Baumgart et al. | |
| 4,485,816 A | 12/1984 | Krumme | |
| 4,632,100 A | 12/1986 | Somers et al. | |
| 4,665,906 A | 5/1987 | Jervis | |
| 4,669,473 A | 6/1987 | Richards et al. | |
| 4,898,156 A | 2/1990 | Gatturna et al. | |
| 4,946,468 A | 8/1990 | Li | |
| 5,002,550 A | 3/1991 | Li | |
| 5,035,712 A | 7/1991 | Hoffman | |
| 5,046,513 A | 9/1991 | Gatturna et al. | |
| 5,190,546 A | 3/1993 | Jervis | |
| 5,192,303 A | 3/1993 | Gatturna et al. | |
| 5,318,579 A | 6/1994 | Chow | |
| 5,356,413 A | 10/1994 | Martins et al. | |
| 5,358,511 A | 10/1994 | Gatturna et al. | |

(Continued)

FOREIGN PATENT DOCUMENTS

| | | | | |
|---|---|---|---|---|
| EP | 0838197 | | 4/1998 | |
| EP | 838197 A2 * | | 4/1998 | ............. A61B 17/04 |

(Continued)

OTHER PUBLICATIONS

International Search Report from international application No. PCT/US2007/064684, mailed Aug. 24, 2007, 2 pp.

(Continued)

*Primary Examiner* — Christian Sevilla
(74) *Attorney, Agent, or Firm* — Knobbe, Martens, Olson & Bear, LLP

(57) ABSTRACT

Systems, apparatuses and methods for securing tissue to bone using a bone anchoring system are described. Methods and apparatuses may allow transformation between locked and unlocked states, thereby allowing adjustment of the tension in the suture. The apparatus and/or methods may allow unidirectional movement of a suture, while preventing slippage or movement of the suture and tissue in the opposite direction. Ends of a suture may be individually tensioned to adjust positioning of a tissue with respect to a bone.

29 Claims, 39 Drawing Sheets

(56) References Cited

U.S. PATENT DOCUMENTS

| | | | |
|---|---|---|---|
| 5,372,599 A | 12/1994 | Martins | |
| 5,383,905 A | 1/1995 | Golds et al. | |
| 5,391,173 A | 2/1995 | Wilk | |
| 5,417,712 A | 5/1995 | Whittaker et al. | |
| 5,486,197 A | 1/1996 | Le et al. | |
| 5,505,735 A | 4/1996 | Li | |
| 5,522,820 A | 6/1996 | Caspari et al. | |
| 5,522,845 A | 6/1996 | Wenstrom, Jr. | |
| 5,554,171 A | 9/1996 | Gatturna et al. | |
| 5,571,104 A | 11/1996 | Li | |
| 5,584,835 A | 12/1996 | Greenfield | |
| 5,601,557 A | 2/1997 | Hayhurst | |
| 5,645,553 A * | 7/1997 | Kolesa et al. | 606/157 |
| 5,647,874 A | 7/1997 | Hayhurst | |
| 5,649,963 A | 7/1997 | McDevitt | |
| 5,662,654 A | 9/1997 | Thompson | |
| 5,662,657 A | 9/1997 | Carn | |
| 5,681,352 A * | 10/1997 | Clancy et al. | 606/232 |
| 5,702,397 A | 12/1997 | Goble et al. | |
| 5,725,557 A | 3/1998 | Gatturna et al. | |
| 5,766,218 A | 6/1998 | Arnott | |
| 5,843,127 A | 12/1998 | Li | |
| 5,876,434 A | 3/1999 | Flomenblit et al. | |
| 5,893,856 A | 4/1999 | Jacob et al. | |
| 5,957,953 A | 9/1999 | DiPoto et al. | |
| 5,964,770 A | 10/1999 | Flomenblit et al. | |
| 5,972,000 A | 10/1999 | Beyar et al. | |
| 5,984,927 A | 11/1999 | Wenstrom, Jr. et al. | |
| 6,027,523 A * | 2/2000 | Schmieding | 606/232 |
| 6,042,583 A | 3/2000 | Thompson et al. | |
| 6,066,160 A | 5/2000 | Colvin et al. | |
| 6,077,216 A | 6/2000 | Benderev et al. | |
| 6,113,611 A | 9/2000 | Allen et al. | |
| 6,146,406 A | 11/2000 | Shluzas et al. | |
| 6,200,330 B1 | 3/2001 | Benderev et al. | |
| 6,210,413 B1 | 4/2001 | Justis et al. | |
| 6,299,448 B1 | 10/2001 | Zdrahala et al. | |
| 6,328,758 B1 | 12/2001 | Tornier et al. | |
| 6,334,446 B1 | 1/2002 | Beyar | |
| 6,387,041 B1 | 5/2002 | Harari et al. | |
| 6,406,480 B1 | 6/2002 | Beyar et al. | |
| 6,447,524 B1 | 9/2002 | Knodel et al. | |
| 6,451,024 B1 | 9/2002 | Thompson et al. | |
| 6,527,774 B2 | 3/2003 | Lieberman | |
| 6,544,273 B1 | 4/2003 | Harari et al. | |
| 6,585,730 B1 | 7/2003 | Foerster | |
| 6,635,058 B2 | 10/2003 | Beyar et al. | |
| 6,656,183 B2 | 12/2003 | Colleran et al. | |
| 6,663,642 B2 | 12/2003 | Beyar et al. | |
| 6,692,516 B2 | 2/2004 | West, Jr. et al. | |
| 6,730,110 B1 | 5/2004 | Harari et al. | |
| 6,746,455 B2 | 6/2004 | Beyar et al. | |
| 6,770,076 B2 | 8/2004 | Foerster | |
| 6,773,437 B2 | 8/2004 | Ogilvie et al. | |
| 6,960,160 B2 | 11/2005 | Browning | |
| 6,986,781 B2 | 1/2006 | Smith | |
| 7,083,638 B2 | 8/2006 | Foerster | |
| 7,090,690 B2 | 8/2006 | Foerster et al. | |
| 7,309,337 B2 | 12/2007 | Colleran et al. | |
| 2001/0051816 A1 | 12/2001 | Enzerink et al. | |
| 2002/0111653 A1 | 8/2002 | Foerster | |
| 2003/0088272 A1 | 5/2003 | Smith | |
| 2003/0120309 A1 | 6/2003 | Colleran et al. | |
| 2004/0078054 A1 | 4/2004 | Biggs et al. | |
| 2004/0098050 A1 | 5/2004 | Foerster et al. | |
| 2004/0220617 A1 | 11/2004 | Pedlick et al. | |
| 2004/0267275 A1 * | 12/2004 | Cournoyer et al. | 606/99 |
| 2005/0080454 A1 | 4/2005 | Drews et al. | |
| 2005/0187555 A1 | 8/2005 | Biedermann et al. | |
| 2005/0245932 A1 | 11/2005 | Fanton et al. | |
| 2006/0089525 A1 | 4/2006 | Mamo et al. | |
| 2006/0100630 A1 | 5/2006 | West, Jr. | |
| 2006/0106423 A1 | 5/2006 | Weisel et al. | |
| 2006/0122608 A1 * | 6/2006 | Fallin et al. | 606/72 |
| 2006/0282081 A1 | 12/2006 | Fanton et al. | |
| 2006/0282082 A1 | 12/2006 | Fanton et al. | |
| 2006/0282083 A1 | 12/2006 | Fanton et al. | |
| 2007/0038219 A1 | 2/2007 | Matthis et al. | |
| 2007/0156148 A1 | 7/2007 | Fanton et al. | |
| 2007/0156149 A1 | 7/2007 | Fanton et al. | |
| 2007/0156150 A1 | 7/2007 | Fanton et al. | |
| 2007/0156176 A1 | 7/2007 | Fanton et al. | |
| 2007/0255317 A1 | 11/2007 | Fanton et al. | |
| 2007/0260259 A1 | 11/2007 | Fanton et al. | |

FOREIGN PATENT DOCUMENTS

| | | |
|---|---|---|
| EP | 1820462 | 8/2007 |
| WO | WO 94/28799 | 12/1994 |
| WO | 9639948 | 12/1996 |
| WO | WO 97/30649 | 8/1997 |
| WO | 9811829 | 3/1998 |
| WO | 9922648 | 5/1999 |
| WO | WO 2005/074827 | 8/2005 |
| WO | WO 2005/102190 | 11/2005 |
| WO | WO 2005/122954 | 12/2005 |
| WO | WO 2006/037131 | 4/2006 |

OTHER PUBLICATIONS

International Search Report from international application No. PCT/US2007/064681, mailed Jan. 21, 2008, 4 pp.
Duerig et al., "Metals: Superelastic Nitinol for Medical Devices," *Medical Plastics and Biomaterials*, Mar. 1997, 7 pp.
International Search Report from international application No. PCT/US2005/013172, dated Feb. 17, 2006, 1 pg.
International Preliminary Report on Patentability (with Written Opinion) from international application No. PCT/US2007/060098, dated Jul. 8, 2008, 9 pp.
International Search Report from international application No. PCT/US2007/060098, dated Apr. 3, 2007, 4 pp.
International Preliminary Report on Patentability (with Written Opinion) from international application No. PCT/US2007/060099, dated Jul. 8, 2008, 8 pp.
International Search Report from international application No. PCT/US2007/060099, dated May 23, 2007, 4 pp.
International Search Report and Written Opinion of international application No. PCt/US08/02885, mailed Jul. 18, 2008, 10 pp.
International Preliminary Report on Patentability with Written Opinion, from international application No. PCT/US2007/064681, mailed Oct. 2, 2008, 10 pp.

* cited by examiner

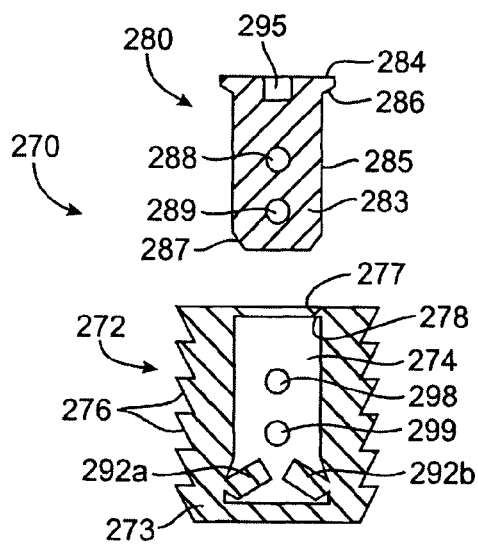
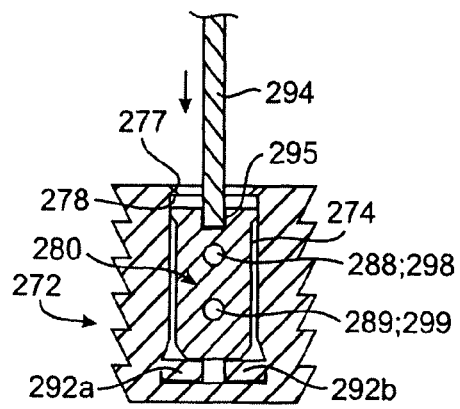
FIG. 13A
FIG. 13B
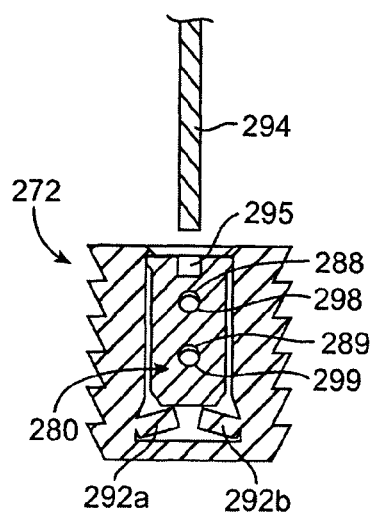
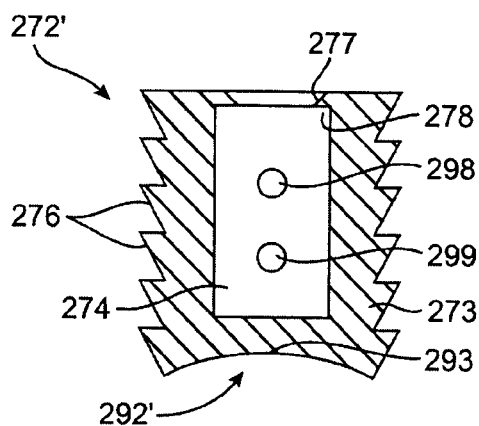
FIG. 13C
FIG. 14

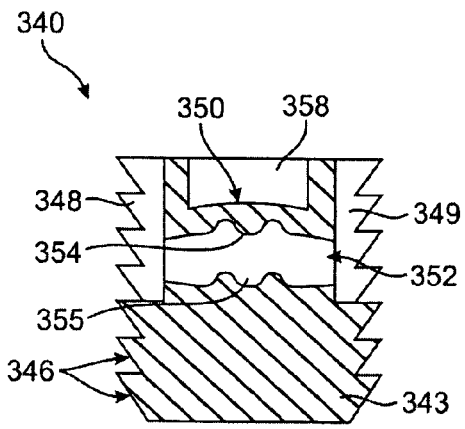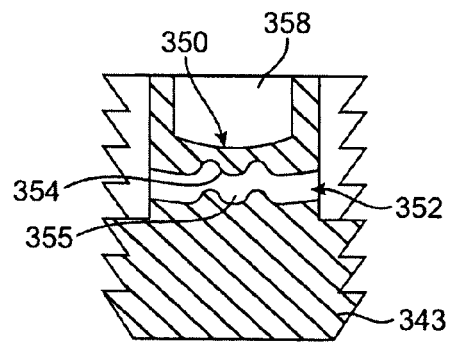
FIG. 17A  FIG. 17B
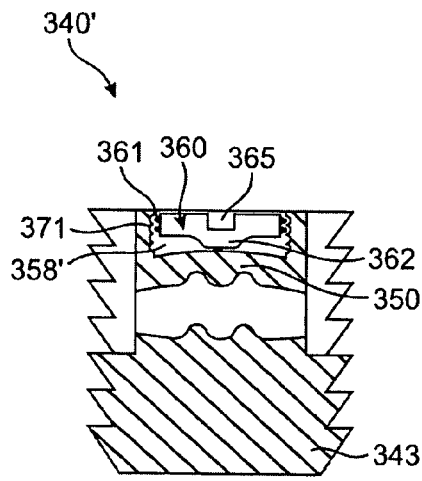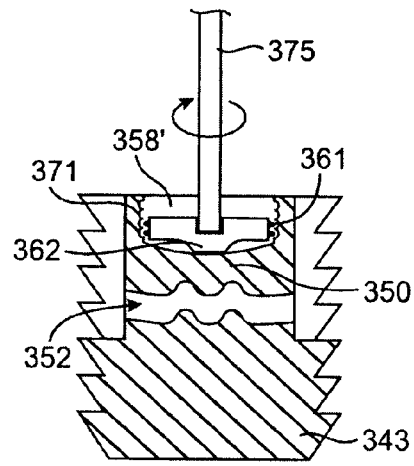
FIG. 18A  FIG. 18B
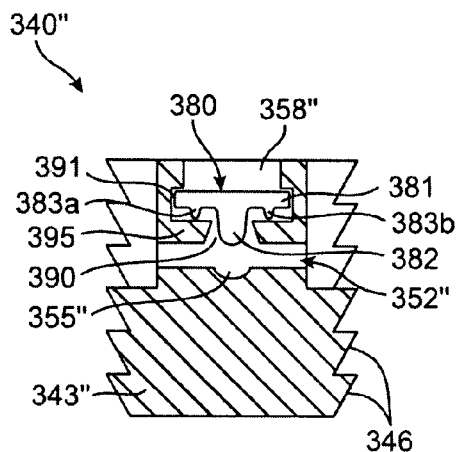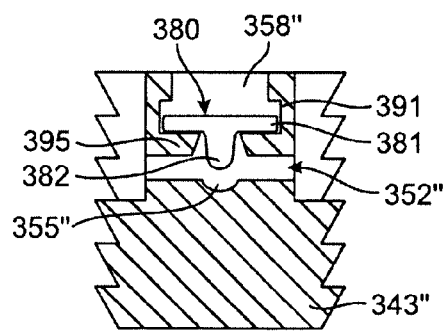
FIG. 19A  FIG. 19B

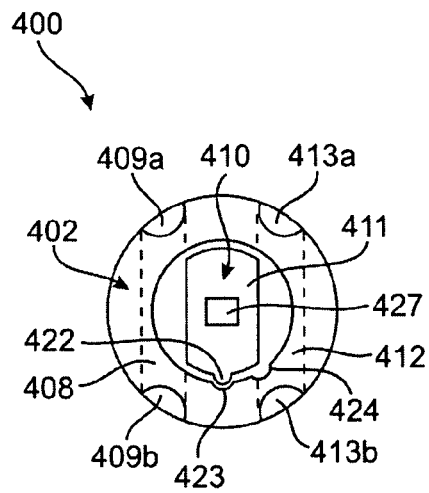
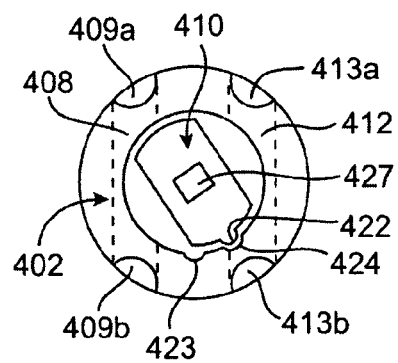
FIG. 20A
FIG. 21A
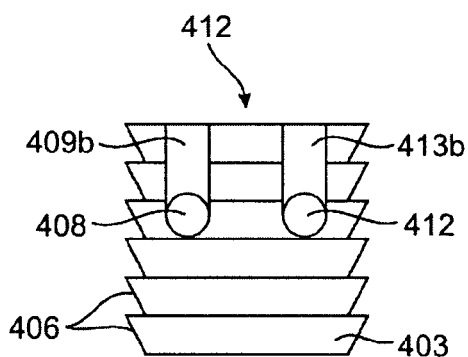
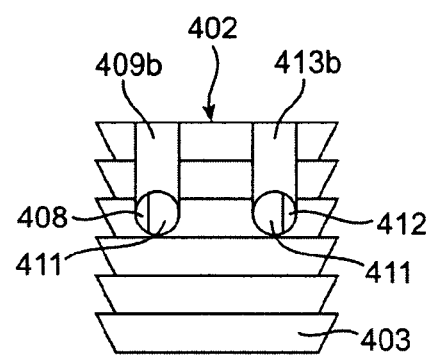
FIG. 20B
FIG. 21B

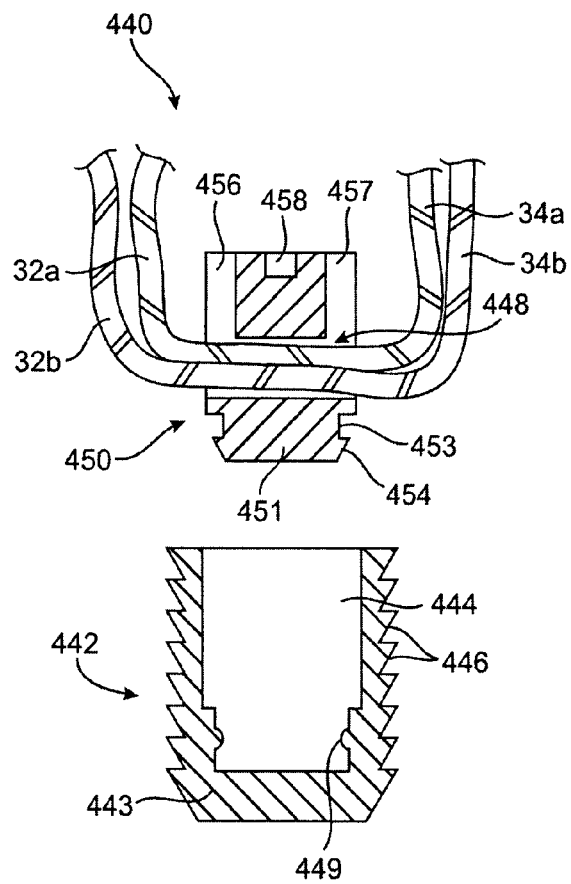
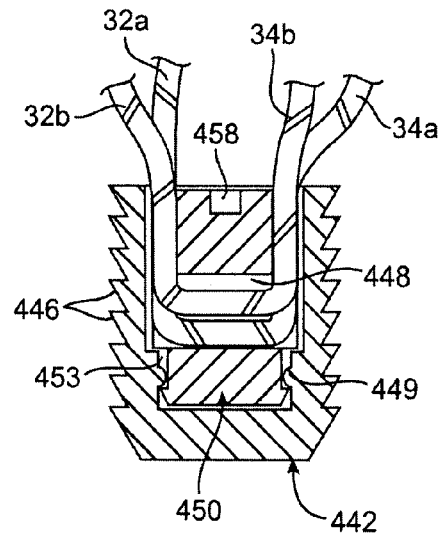
FIG. 22B
FIG. 22A
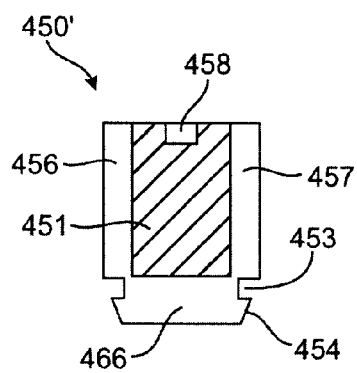
FIG. 23A
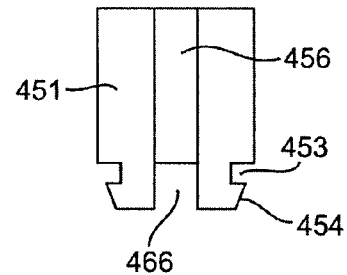
FIG. 23B
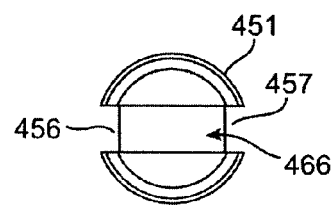
FIG. 23C

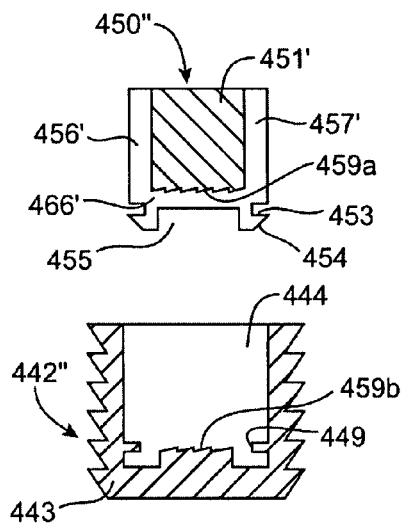
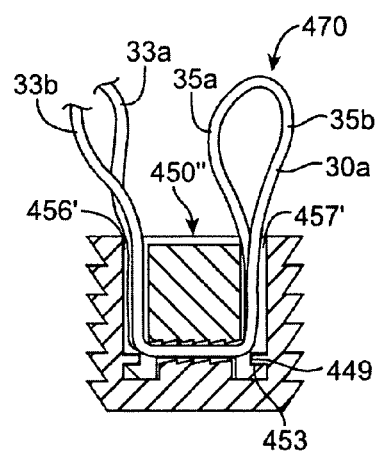
FIG. 24A  FIG. 24B
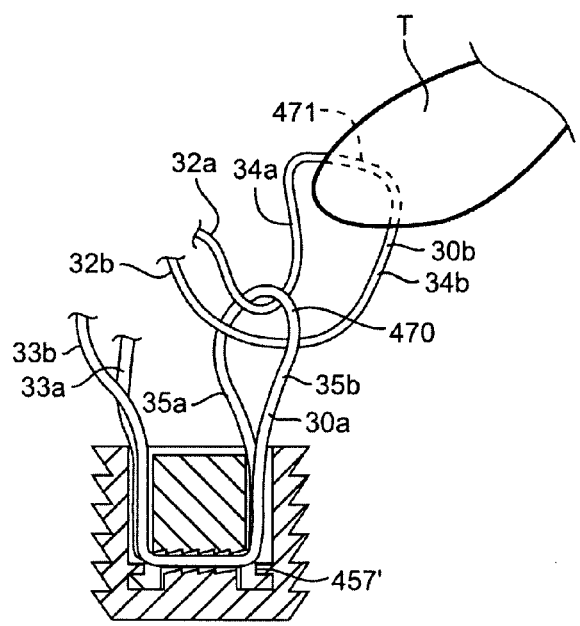
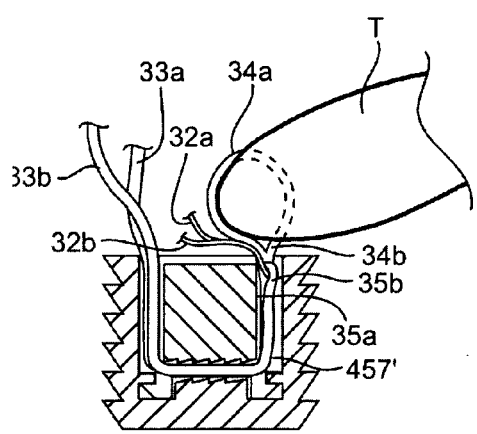
FIG. 25A  FIG. 25B

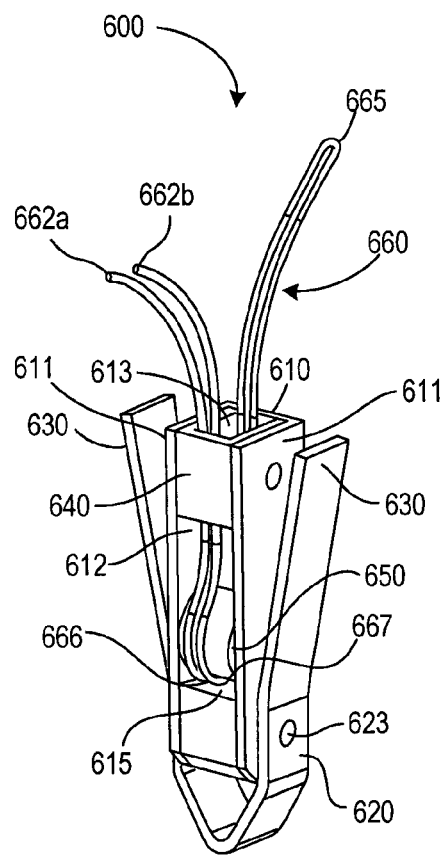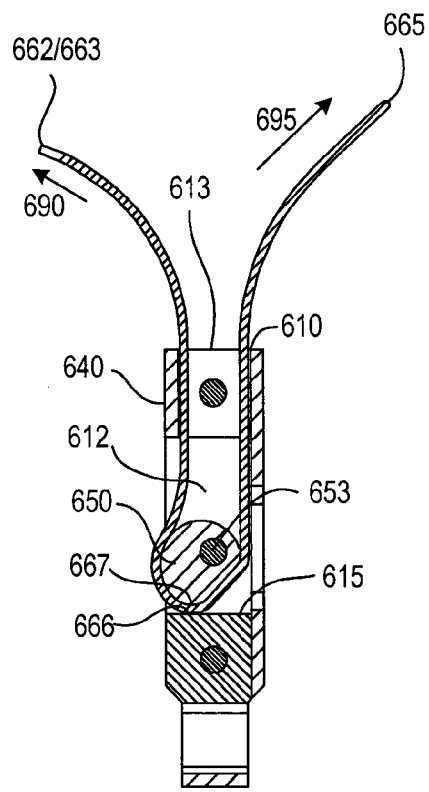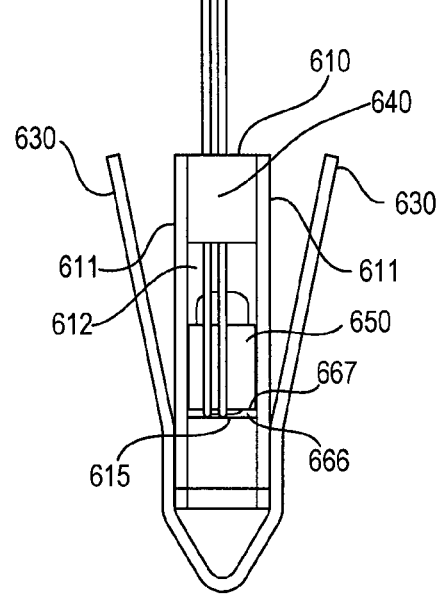
FIG. 29A
FIG. 29B
FIG. 29C

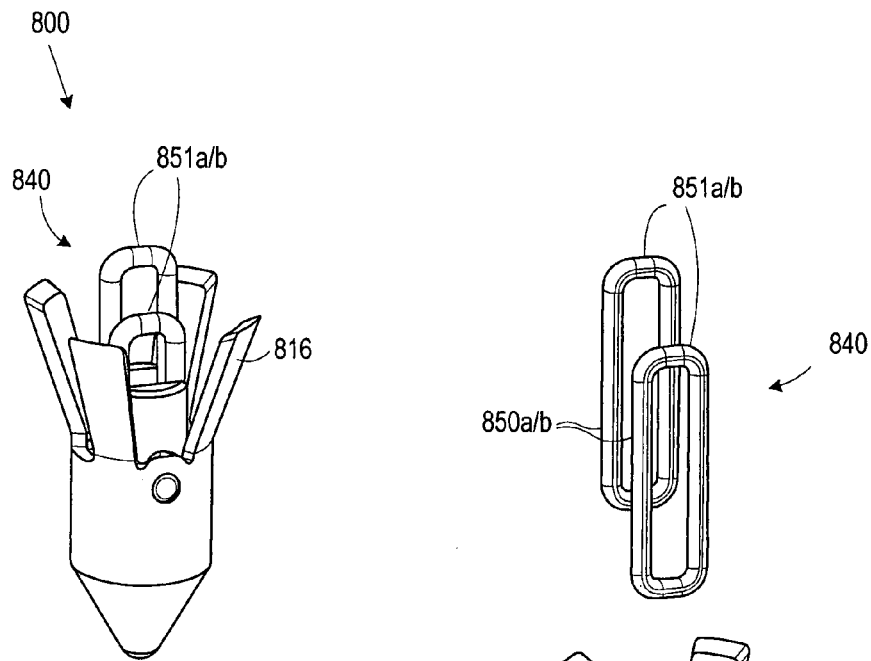
FIG. 31A
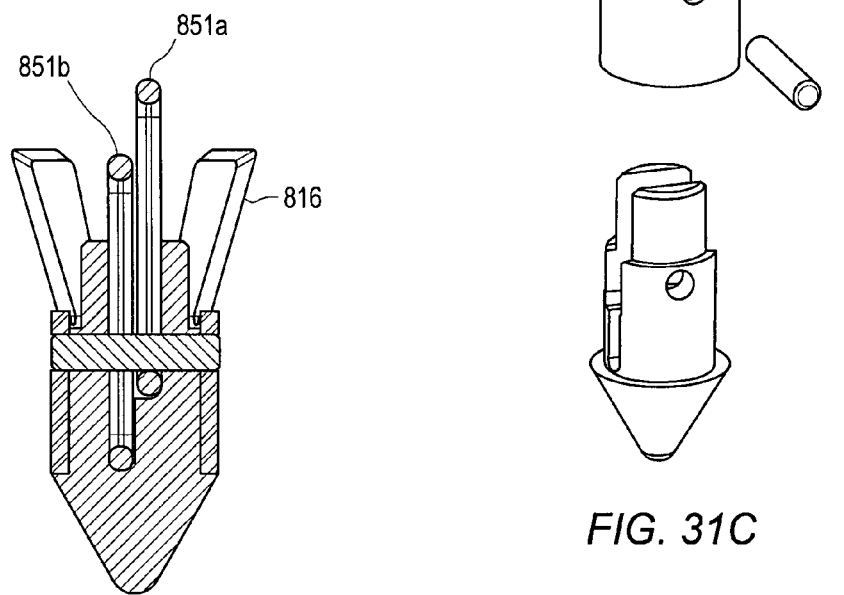
FIG. 31B
FIG. 31C

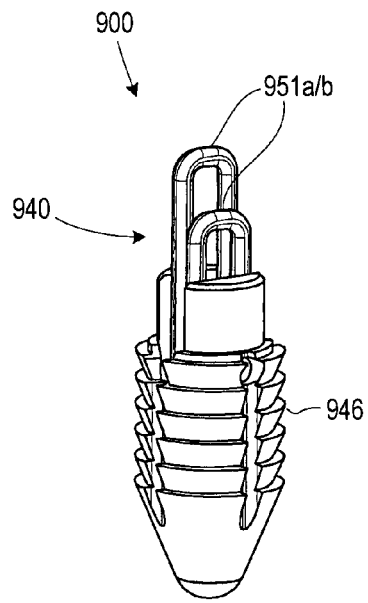
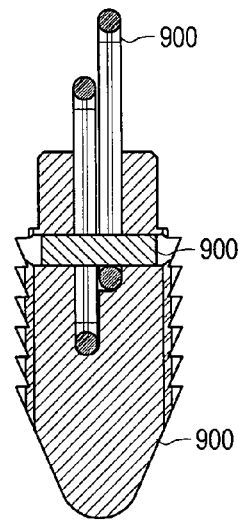
FIG. 32A FIG. 32B
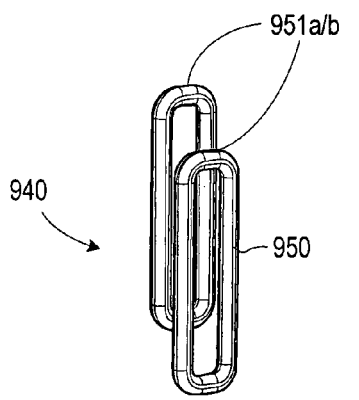
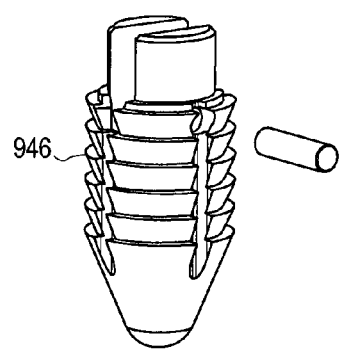
FIG. 32C

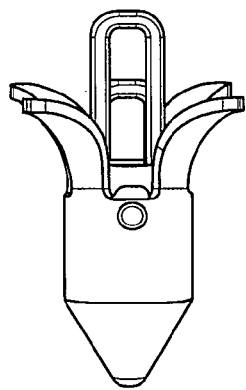
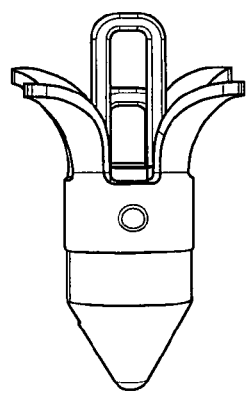
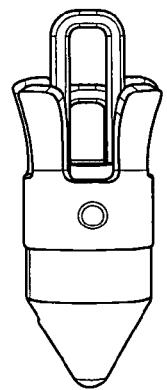
FIG. 35A  FIG. 35B  FIG. 35C
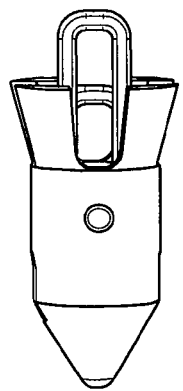
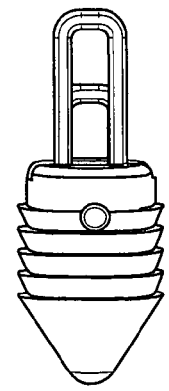
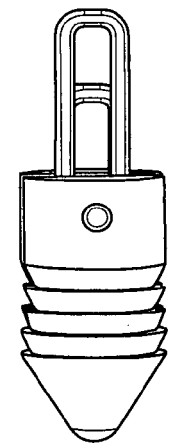
FIG. 35D  FIG. 35E  FIG. 35F
FIG. 35G

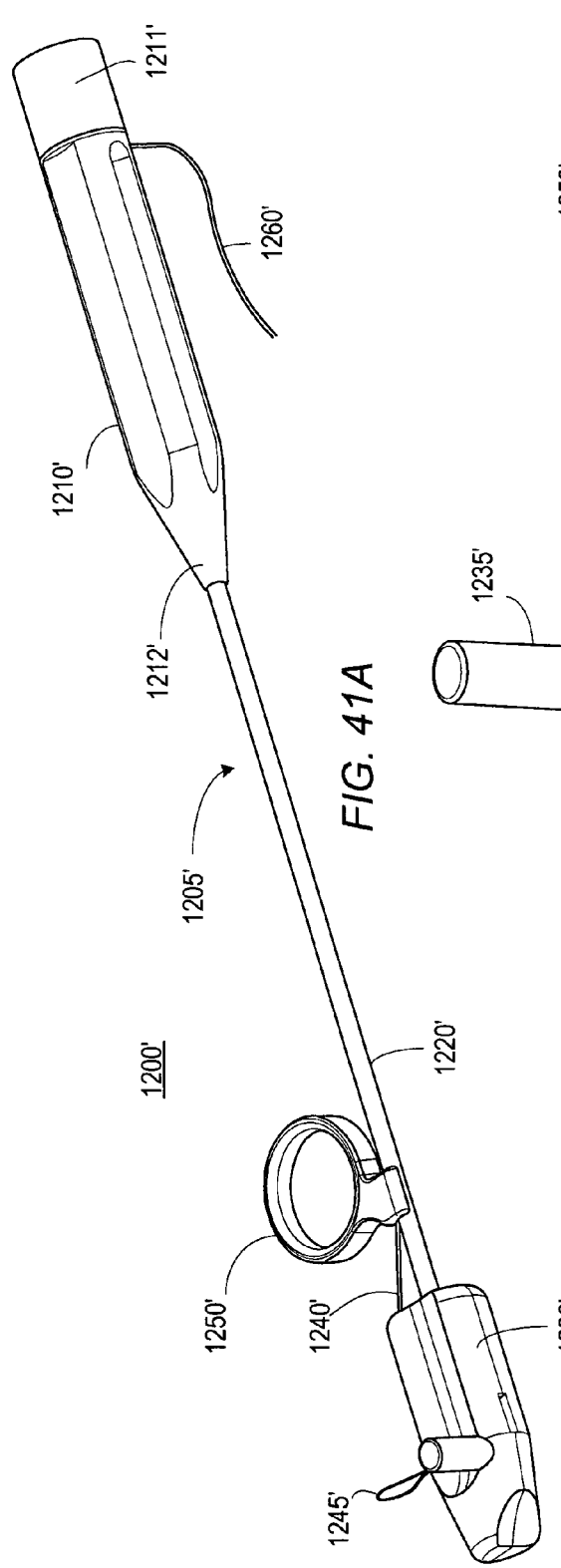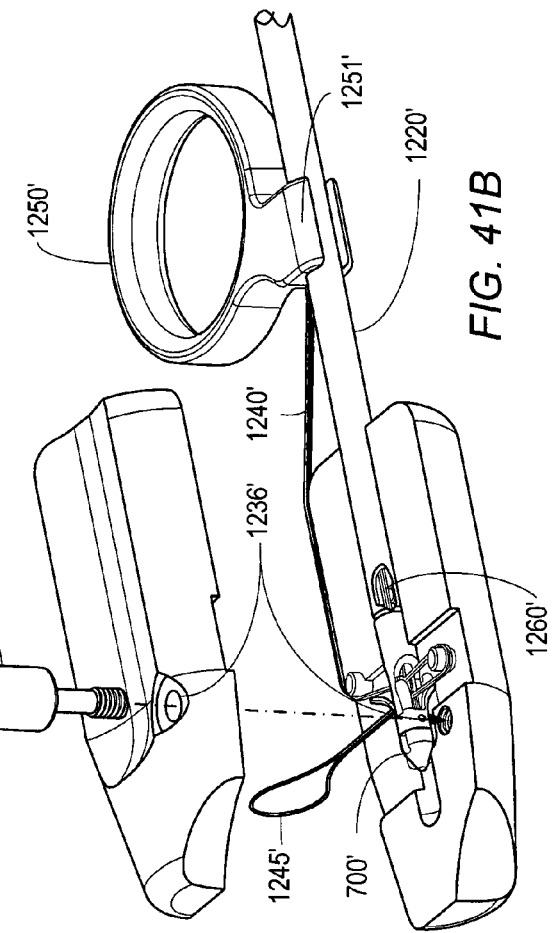
FIG. 41A
FIG. 41B

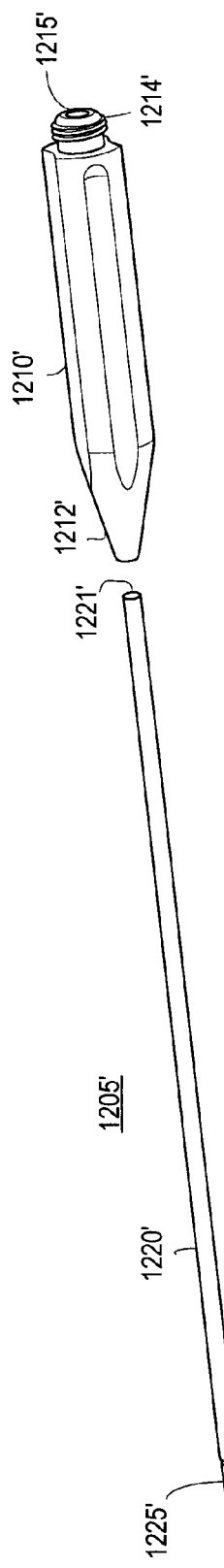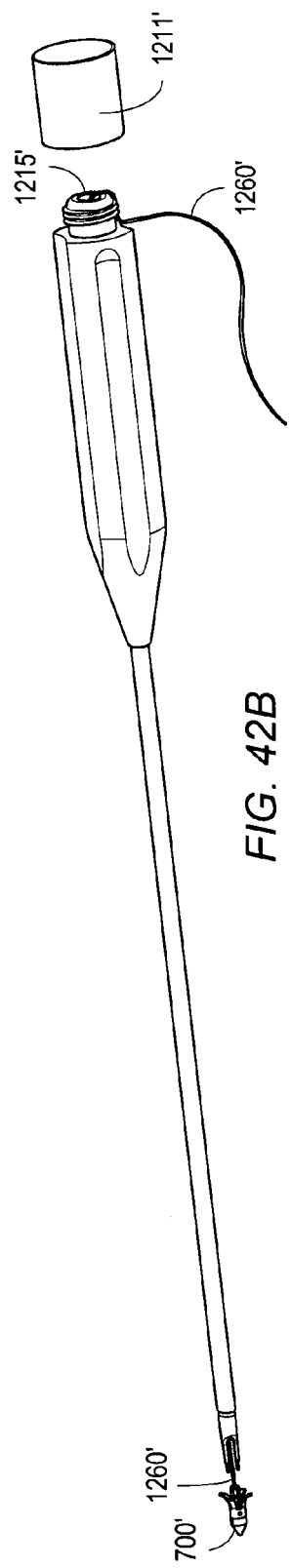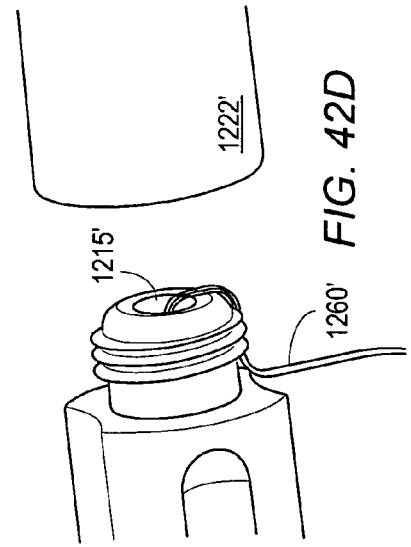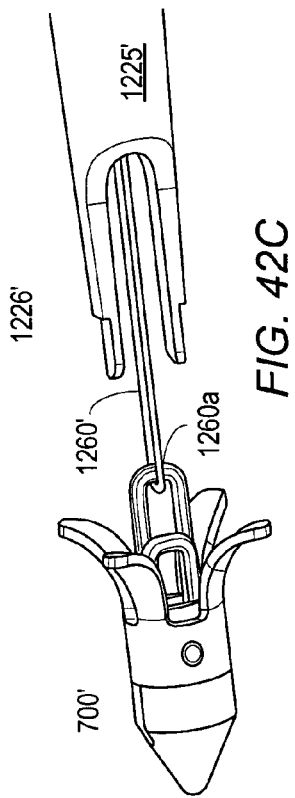
FIG. 42A
FIG. 42B
FIG. 42C
FIG. 42D

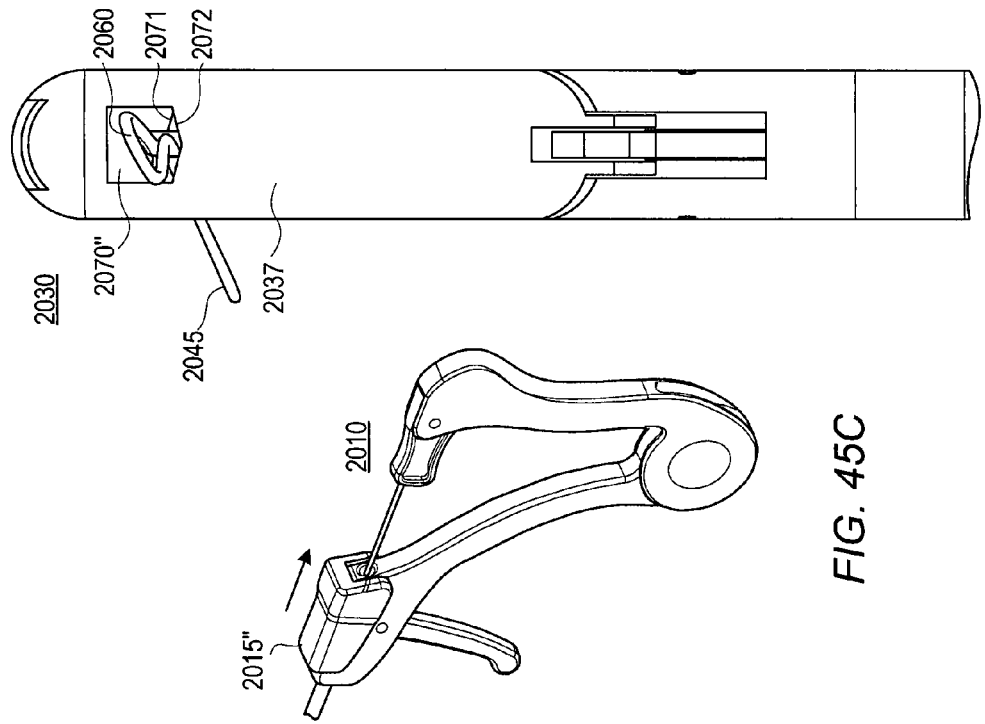

BONE ANCHOR INSTALLER AND METHOD OF USE

CROSS REFERENCE TO RELATED APPLICATIONS

The present application claims the right of priority under 35 U.S.C. §119 to U.S. provisional application No. 60/784,679, filed Mar. 22, 2006. The prior application is commonly owned with the present application and the entire contents thereof are hereby expressly incorporated by reference in its entirety as though fully set forth herein.

BACKGROUND

1. Field of the Invention

The present invention relates to systems, methods and apparatus for securing tissue to bone. More particularly, the invention relates to apparatus and methods for facilitating the attachment of tissue to bone using a bone anchoring system. The present invention further relates to a suture passer instruments for retrieving a suture loop.

2. Description of the Related Art

Many attempts have been made to provide devices that allow the arthroscopic securing of torn tissue to a human bone. For example, numerous devices have been designed to allow a torn rotator cuff to be secured to a humeral head of the shoulder.

Typically, in a first step, a hole is drilled into the bone under arthroscopic visualization. A length of a suture length is threaded through a portion of a tissue, and then coupled to a bone anchor configured. One or more sutures may be manipulated outside of the arthroscopic site.

Once the suture is coupled between the tissue and the bone anchor, the bone anchor may be inserted into the hole. The bone anchor may be configured to lock itself within the hole in the bone upon deployment therein. Several means for securing the bone anchor within the hole of a bone are known in the art.

Once the bone anchor is secured within the hole in the bone, one or both ends of the suture may be tensioned to approximate the positioning of the tissue with respect to the bone. Once the tissue is positioned as desired, the suture may be locked in place to maintain the tension in the suture. The free end or ends of the suture may be clipped under arthroscopic visualization to complete the procedure.

An example of a previously known method and apparatus for attaching tissue to bone is described in U.S. Pat. No. 6,585,730 to Foerster, which is incorporated by reference herein. Foerster describes devices and methods for securing sutures to a bone anchor without the requirement of knot tying. In Foerster, suture legs, after having been placed into soft tissues to be anchored to bone, are threaded through the anchor and then through a floating wedge block located at the distal end of the anchor. The wedge block is configured such that it has a hollow lumen through the center, and a conically tapered outer surface. The sutures are passed back around the outside of the wedge block such that they rest on the conical surface. They are then re-threaded in the opposite direction back through the anchor, exiting the anchor at the proximal end thereof. The anchor is then inserted into the bone, and secured. When tension is placed on the legs of the suture passing back out of the anchor, the suture is drawn through the hollow center lumen, around the distal end of the wedge block, and back out of the anchor. This tension tends to cause the wedge block to force its way back up into the anchor body, and a means to prevent this may be employed. Such means may include any structure that selectively holds the wedge block separate from the anchor body.

At this juncture, by pulling on the suture legs, any slack in the sutures is removed, and the soft tissues are drawn toward the anchor. When the soft tissues are in the desired orientation, relative to the bone to which they are to be attached, the structure holding the wedge block is removed, and the back tension on the sutures pulls the wedge block into the matching taper in the anchor body, maintaining the compressive force on the suture legs.

Another previously known knotless suture anchor is described in U.S. Pat. No. 6,692,516 to West et al. ("West"), which is incorporated by reference herein. West describes a knotless suture anchor and method for knotlessly securing. The suture anchor has a deformable portion for engaging with a wall of a borehole in a first tissue member, a shaft for providing a force to the deformable portion to deform the deformable portion to cause the deformable portion to engage the wall of the borehole, a suture retaining portion in at least one of the deformable portion and the shaft for retaining two suture portions in the retaining portion with a loop formed between the two suture portions. The loop is adapted to traverse a second tissue member to be attached to the first tissue member. Application of the force to deform the deformable portion causes engagement of the deformable portion with the borehole to secure the suture anchor to the first tissue and clamping of at least one of the two suture portions in the suture retaining portion thereby to secure the suture forming the loop in the suture retaining portion and secure the second tissue to the suture anchor.

Systems, apparatus and methods are desired for securing tissue to bone that allow direct tactile feedback of the tension in the suture between the tissue and bone. During securing tissue to bone, it is desired to be able to adjust positioning of the tissue with respect to the bone. In securing the tissue to bone, the suture may be locked in place without tying a knot.

Endoscopic suturing techniques and instruments have been developed to facilitate the suturing of tissue during endoscopic surgical procedures. Access to a surgical work site within a patient's body is normally provided through one or more portals formed directly in the patient's body or through one or more cannulas inserted into the patient's body through small incisions. A chosen surgical procedure is carried out by a surgeon through the use of elongated instruments inserted through these cannulas and it often becomes necessary to suture selected tissue at the surgical work site.

The arthroscopic work site is typically accessible only through a small portal or cannula. Since it is very difficult to tie sutures within the body, various devices and techniques have been developed to enable the surgeon to tie sutures endoscopically. For example, some procedures enable the surgeon to pass a suture through the target tissue and form a surgical knot extracorporeally and then move the knot with a knot pusher through the portal or cannula into position adjacent the desired tissue to be sutured. Formation of the knot requires the surgeon to manually retrieve and tie a knot on the suture after the suture is threaded through the tissue(s). This procedure is often tedious and time-consuming. The procedure further requires that a mechanical means of retrieving the suture be provided. Most devices require the use of a separate tool to grab onto and retrieve the suture, thereby further reducing the working space and adding risk of contamination, or leading to a tendency for the suture to deform or collapse suture is manually retrieved. In addition, tying the knot in this manner is particularly difficult during endoscopic surgeries, where the visual field for the surgeon is severely limited by the narrow surgical area. As a result of these setbacks, there is a need for an improved method of retrieving a suture, as well as for surgical devices that will facilitate such method.

SUMMARY OF THE INVENTION

In some embodiments, a bone anchor installer system includes an installer tool. The installer tool may include a handle portion coupled to a loader portion. The loader portion may be configured such that a bone anchor is couplable to at least a portion thereof.

In an embodiment, a bone anchor installer system may include a bone anchor coupled to the distal end of the installer tool. The system may further include a means of tethering a bone anchor coupled to the distal end of the installer tool. The tethering means may be accessible to a surgeon during use.

In an embodiment, a bone anchor installer system may include an anchor holder removably coupled to the distal end of the loader portion. The anchor holder may include a first portion coupled to a second portion, said first and second portions defining a cavity sized to accept the distal end of the loader portion having a bone anchor is coupled thereto. An anchor holder may further include a means of uncoupling the anchor holder from the distal end of the installer tool.

In an embodiment, a bone anchor installer system may include a suture puller coupled to the anchor holder such that coupling a suture to a bone anchor during use is facilitated. A suture puller may include a proximal end configured to allow an operator to pull the suture puller through the anchor holder. A suture puller may include a central portion. The central portion may be engaged with the anchor holder and a bone anchor residing therein such that pulling the proximal end of the suture holder couples one or more suture ends to the bone anchor. A suture puller may include a distal end. The distal end of a suture puller may be couplable to one or more sutures.

In an embodiment, an installer system may include a cannula configured such that at least a portion of the installer having a bone anchor coupled thereto is deliverable to a surgical site during use.

In some embodiments, an installer system may include an installer tool that includes a handle portion and a loader portion. The loader portion may have a proximal end and a distal end. The proximal end may be coupled to the handle portion. The distal end may be configured such that a bone anchor is couplable thereto. A channel may extend from the handle portion to the distal end of the loader portion.

In an embodiment, an installer system may include a means of tethering a bone anchor to the distal end of the loader portion. The tethering means may be positioned within the channel of the installer tool. At least a portion of the tethering means may be accessible to a surgeon during use.

BRIEF DESCRIPTION OF THE DRAWINGS

Other objects and advantages of the invention will become apparent upon reading the following detailed description and upon reference to the accompanying drawings in which:

FIG. 13A is a cross-sectional view of an embodiment of a bone anchor that includes a bone anchor member and a plug portion;

FIGS. 13B and 13C are illustrations of usage of the bone anchor depicted in FIG. 13A;

FIG. 14 is a cross-sectional view of an embodiment of an apparatus that includes a bone anchor member with a spring element;

FIGS. 17A and 17B are cross-sectional views of embodiments of a bone anchor in an unlocked state and a locked state, respectively;

FIGS. 18A and 18B are cross-sectional views of embodiments of a bone anchor in an unlocked state and a locked state, respectively;

FIGS. 19A and 19B are cross-sectional views of an alternative embodiment of the bone anchor depicted in FIGS. 17A and 17B;

FIGS. 20A and 20B are, respectively, a cross-sectional view and a perspective side view of an embodiment of an unlocked state of a bone anchor that includes a bone anchor member and a plug portion;

FIGS. 21A and 21B are, respectively, a cross-sectional view and a perspective side view depicted in FIGS. 20A and 20B in a locked state;

FIG. 22A is a cross-sectional view of an embodiment of a bone anchor that includes a bone anchor member and a plug portion;

FIG. 22B is a cross-sectional view of the plug portion inserted in the bone anchor member depicted in FIG. 22A;

FIG. 23A is a cross-sectional view of an embodiment of the plug depicted in FIGS. 22A and 22B;

FIG. 23B is a perspective side view of the plug depicted in FIG. 23A;

FIG. 23C is a perspective bottom view of the plug depicted in FIG. 23A;

FIG. 24A is a cross-sectional view of an embodiment of a bone anchor that includes a bone anchor member and a plug portion;

FIG. 24B is a cross-sectional view of a plug portion inserted into the bone anchor member depicted in FIG. 24A;

FIGS. 25A and 25B are illustrations of the bone anchor depicted in FIGS. 24A and 24B employing two sutures;

FIG. 29A depicts an embodiment of a bone anchor having a cam with a suture positioned between the cam and a surface at the distal end of the bone anchor;

FIG. 29B is a cross-sectional view of the embodiment depicted in FIG. 29A;

FIG. 29C is a perspective front view of the bone anchor depicted in FIG. 29A;

FIG. 31A depicts an alternate embodiment of a bone anchor having a suture locking assembly;

FIG. 31B is a cross-sectional view of the bone anchor depicted in FIG. 31A;

FIG. 31C is an exploded view of the bone anchor depicted in FIG. 31A;

FIG. 32A depicts a further alternate embodiment of a bone anchor having a suture locking assembly;

FIG. 32B depicts a cross sectional view of the bone anchor of FIG. 32A;

FIG. 32C depicts an exploded view of the bone anchor of FIG. 32A;

FIG. 35A-FIG. 35G depict a variety of alternate bone anchor embodiments;

FIG. 41A depicts an anchor installer according to alternate embodiment;

FIG. 41B shows the distal end of the anchor installer depicted in FIG. 461 with one half of the anchor holder removed;

FIG. 42A shows the component forming the anchor loader portion of the installer shown in FIG. 41A;

FIG. 42B shows the anchor loader FIG. 42A in its assembled state with a bone anchor coupled to the distal end thereof by a tethering means;

FIG. 42C is an enlarged view of the distal end of the loader and bone anchor tethered thereto depicted in FIG. 42B;

FIG. 42D is an enlarged view of the proximal end of the loader and tethering means shown in FIG. 42B;

FIGS. 45A through 45D are schematic depictions of the proximal and distal ends of the suture passer depicted in FIG. 43 in the retracted (FIG. 45A and FIG. 45B) and engaged (FIG. 45C and FIG. 45D) states, respectively.

Figure 1:
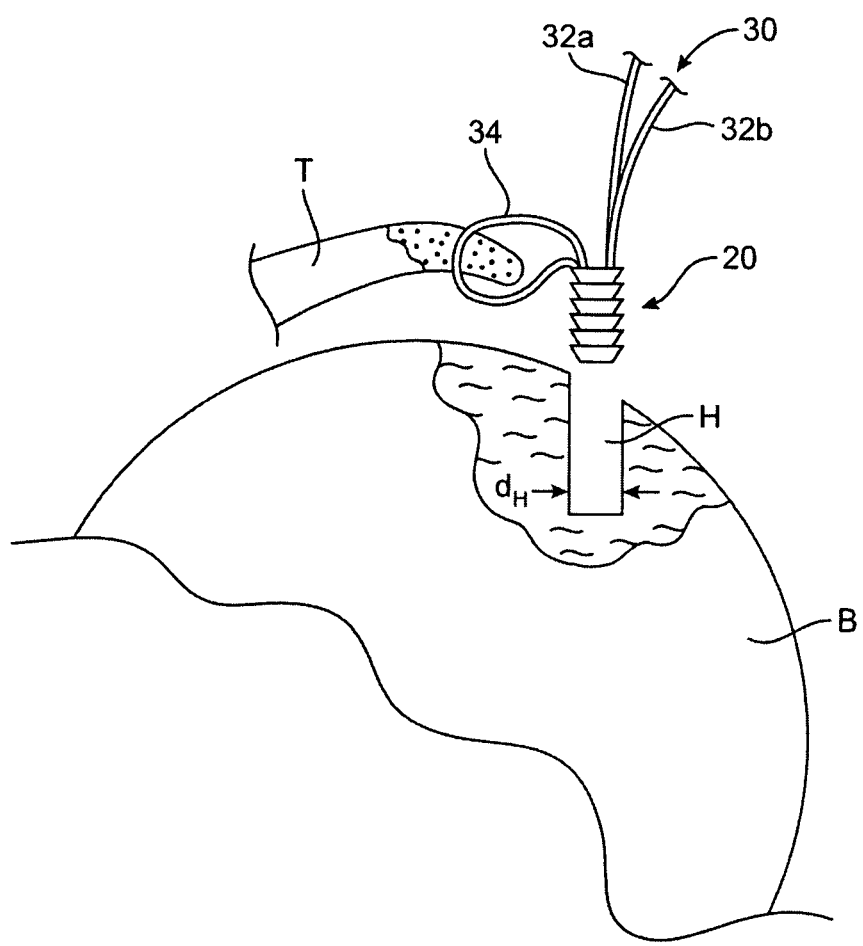
FIG. 1 is a schematic of a bone and tissue interface.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

FIG. 1 is an illustrative schematic of a bone and tissue interface. Tissue T has a torn end and it is desirable to secure the torn end to a section of bone B. In a first step, hole H having diameter $d_H$ may be drilled in bone B, as depicted, using generally known bone drilling techniques.

Bone anchor member 20 may secure tissue T to bone B. Bone anchor member 20 may be used in conjunction with a length of suture 30. Suture 30 has first end 32a and second end 32b. Ends 32a, 32b may be coupled to bone anchor member 20. A central region of suture 30 forms loop 34. Loop 34 may be threaded through a section of tissue T near the torn end of the tissue using generally known threading techniques. In embodiments described herein tissue, hole, and bone refer to T, H, and B, respectively, as described in FIG. 1.

Figure 2A:
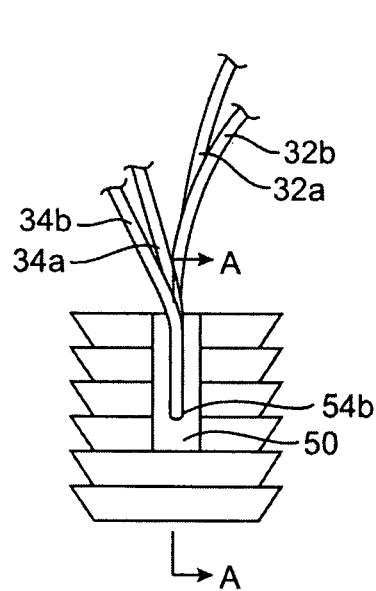
FIG. 2A is a perspective front view of an embodiment of a bone anchor.
Figure 2B:
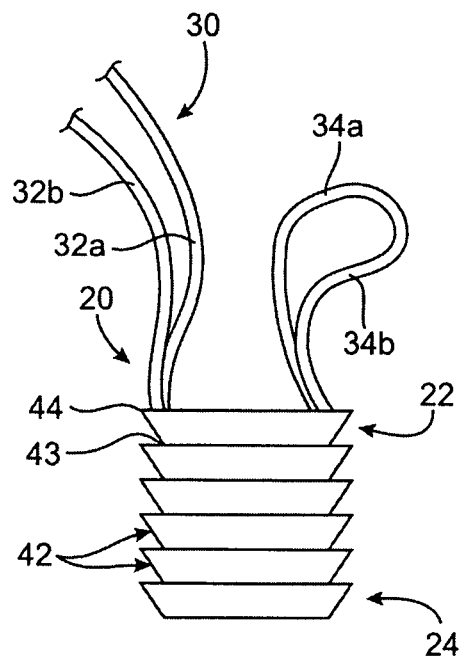
FIG. 2B is a perspective side view of the bone anchor along line A-A of FIG. 2A.
Figure 2C:
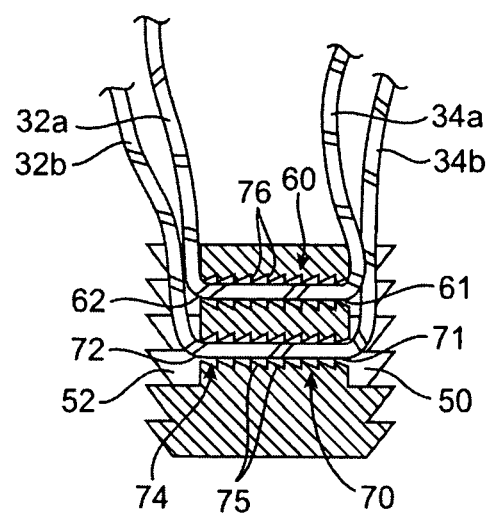
FIG. 2C is a cross-sectional view of the bond anchor depicted in FIG. 2A.

FIG. 2A is a perspective front view of an embodiment of a bone anchor. FIG. 2B is a perspective side view of the bone anchor along line A-A shown in FIG. 2A. FIG. 2C is a cross-sectional view of the bond anchor depicted in FIG. 2A. Bone anchor member 20 has proximal region 22 and distal region 24, as depicted in FIG. 2A. Bone anchor member 20 includes a plurality of cleated members 42. Cleated members 42 may be formed on or attached to an exterior surface of bone anchor member 20. Cleated members 42 may secure bone anchor member 20 within a hole of a bone. In some embodiments, bone anchor member 20 may include radially expandable members. Radially expandable members may embed into bone to secure the bone anchor member to the bone. In some embodiments, bone anchor member 20 may include threaded exterior members. Threaded exterior members may screw into surrounding bone to secure the bone anchor member to the bone.

Referring to FIGS. 2B-2C, bone anchor member 20 includes first guide channel 50 and second guide channel 52. Guide channels 50, 52 are formed within opposing surfaces of bone anchor member 20. Guide channels 50, 52 are configured to accommodate regions of suture 30, so that the suture regions do not extend outside of the confines of the guide channels when in use.

Bone anchor member 20 includes first passage 60 and second passage 70. Passages 60, 70 extend laterally through a main body of bone anchor member 20, as depicted in FIG. 2C. Passage 60 communicates with first guide channel 50 via opening 61, and further communicates with guide channel 52 via opening 62. Similarly, passage 70 communicates with guide channel 50 via opening 71, and further communicates with guide channel 52 via opening 72.

Passage 60 is shown disposed proximal to second passage 70, i.e., the passage 60 is closer to proximal region 22 of bone anchor member 20. However, as will be apparent to one skilled in the art, the passages also may be disposed adjacent one another, or otherwise positioned, to achieve the objects of the present invention.

Passages 60, 70 include at least one cleated member 74. Cleated member 74 includes angled sections 75 and substantially orthogonal sections 76. Orthogonal sections 76 are disposed adjacent one another, thereby forming a cleated shape, as shown in FIG. 2C. Angled sections 75 are angled towards opening 62 of passage 60 and opening 72 of passage 70, as shown in FIG. 2C. In some embodiments, cleated passages 60, 70 are configured to permit one-way movement of first suture end 32a and second suture end 32b. For example, when suture end 32a is pulled in a proximal direction, angled sections 75 allow movement of the suture end in the proximal direction, while inhibiting distally advancement of suture end 32a within passage 60.

In certain embodiments, an outer diameter of suture 30 may be slightly larger than an inner diameter of cleated passages 60 and 70. Therefore, suture ends 32a and 32b can pass through cleated passages 60 and 70 in a proximal direction with relatively little resistance while the suture holds significantly greater force in the distal direction.

In one embodiment, a method for coupling suture 30 between tissue T and bone anchor member 20, a central region of suture 30 can be looped through tissue T first, such that free ends 32a and 32b extend from the tissue. Free end 32a is then threaded through one-way cleated passage 60 in a proximal direction, while free end 32b is threaded through one-way cleated passage 70, also in a proximal direction.

As will be apparent to one skilled in the art, suture 30 may be coupled between tissue T and bone anchor member 20 using other threading techniques, so long as the suture ultimately is situated in a manner depicted in FIG. 2C.

First end 32a of suture 30 is disposed through first passage 60, then transitioned into loop portion 34a. Loop portion 34a transitions into loop portion 34b, forming loop 34 therebetween, which is coupled to tissue T. Loop portion 34b transitions into second end 32b, which is disposed through passage 70, as shown in FIG. 2C. Accordingly, first and second ends 32a, 32b of suture 30 may be independently manipulated for purposes described herein below.

After suture 30 is coupled to bone anchor member 20 and a tissue, bone anchor member 20 is distally advanced into a hole of a bone under arthroscopic guidance. Exterior cleated members 42 of bone anchor member 20 allow the bone anchor member to be advanced distally within the bone hole when an appropriate force is applied, but exterior cleated members 42 inhibit proximal movement of bone anchor member 20 to provide a secure anchor within the bone.

Pulling one or both of suture ends 32a and 32b proximally through cleated passages 60 and 70 may approximate the positioning of the tissue with respect to the bone. The use of two separate passages allows the surgeon to tension each end of the suture independently, which is often desirable when tissue is torn irregularly.

Further, the use of a plurality of cleated passages 60 70 permits incremental tensioning of first and second suture ends 32a, 32b. This allows incremental adjustment during positioning of the tissue, using tactile feedback as a guide. Once a desired tension is achieved, retraction of the suture ends is stopped, and the suture is automatically locked in place. Thus, there is no need to tie a knot.

In some embodiments, guide channels 50 and 52 permit the retraction of suture ends 32a, 32b when bone anchor member 20 is secured within a hole of the bone by providing a clearance between the bone anchor member and the bone itself.

Alternatively, suture 30 may be coupled to bone anchor member 20 using techniques described herein below with respect to FIGS. 3A-3E or FIGS. 6-8. These techniques allow the suture to be coupled to bone anchor member 20 without the need to thread free ends 32a and 32b through passages 60 and 70.

FIGS. 3A-3E shows a further embodiment of bone anchor 20'. Bone anchor 20' includes a first mating portion 22a and a second mating portion 22b. In some embodiments, mating portions 22a, 22b are substantially symmetrical, except as noted below.

Figure 3A:
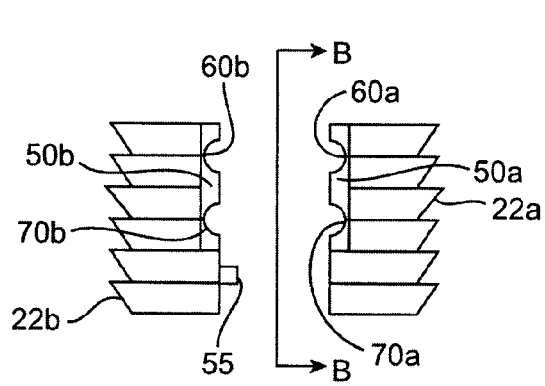
FIG. 3A is a perspective side view of bone anchor.
Figure 3B:
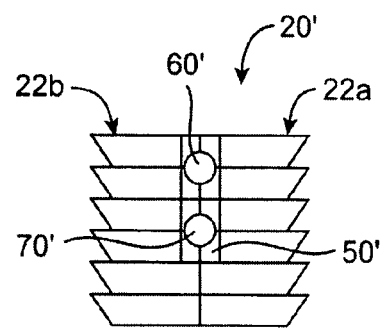
FIG. 3B is exploded side view along line B-B of FIG. 3A.

Turning to FIG. 3B, mating portion 22a includes cleated passage portion 60a and cleated passage portion 70a. Mating portion 22b includes cleated passage portion 60b and cleated passage portion 70b. When assembled state as shown in FIG. 3A, cleated passage portion 60a and cleated passage portion 60b form cleated passage 60', while cleated passage portions 70a and cleated passage portion 70b form cleated passage 70'.

Figure 3C:
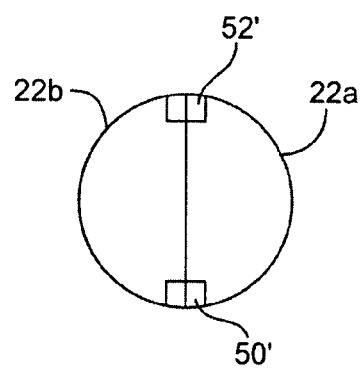
FIG. 3C is perspective top view of the bone anchor depicted in 3A.

Guide channel portions 50a of mating portion 22a and guide channel 50b of mating portion 22b form guide channel 50' in the assembled state as depicted in FIGS. 3A and 3C. Guide channel portion 52a of mating portion 22a and guide channel portion 52b of mating portion 52b form guide channel 52' in the assembled state as depicted in FIG. 3D.

Figure 3D:
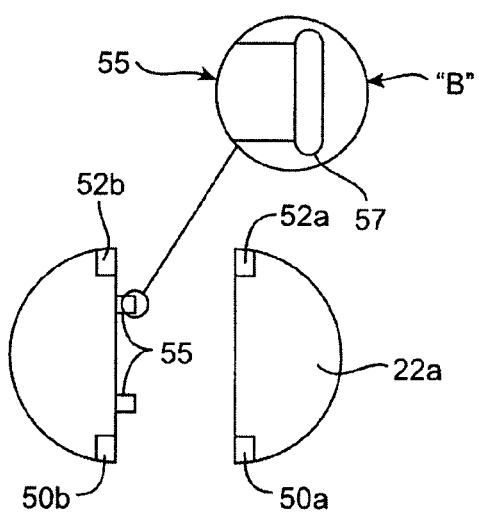
FIG. 3D is a perspective view of the top of the bond anchor depicted in 3C in an open state.
Figure 3E:
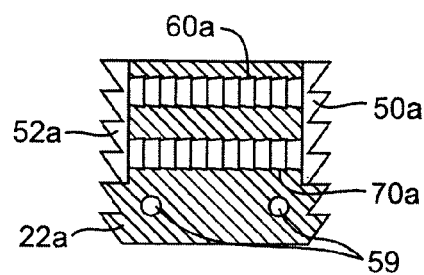
FIG. 3E is a cross-sectional view of the bone anchor depicted in FIG. 3A.

Mating portion 22a includes at least one mating pocket 59, as depicted in FIG. 3E. Mating portion 22b includes at least one protrusion 55, which is configured to securely engage a corresponding pocket 59 in the assembled state of FIGS. 3A and 3C.

In a preferred embodiment, protrusion 55 includes ledge 57, as shown in detail "B" of FIG. 3D. Optionally, mating pocket 59 may include a complementary recess having a slightly larger diameter (not shown), which is configured to receive ledge 57. In this manner, ledge 57 of protrusion 55 may snap into engagement with the larger diameter recess of pocket 59, thereby securing mating portions 22a, 22b.

During use, a first suture end may be positioned in cleated passage portion 60a, and a second suture end positioned in cleated passage portion 70a of FIG. 3E. Next, mating portion 22b is secured to mating portion 22a, (e.g., using a snap-lock engagement described above between protrusion 55 and pocket 59).

The first and second suture ends are disposed through cleated passages 60, 70. Using the bone anchor describe in FIGS. 3A-3E, threading the suture ends through cleated passages 60 and 70 is not necessary, thereby increasing the speed and ease of use of the device.

Figures 4A, 4B, 4C:
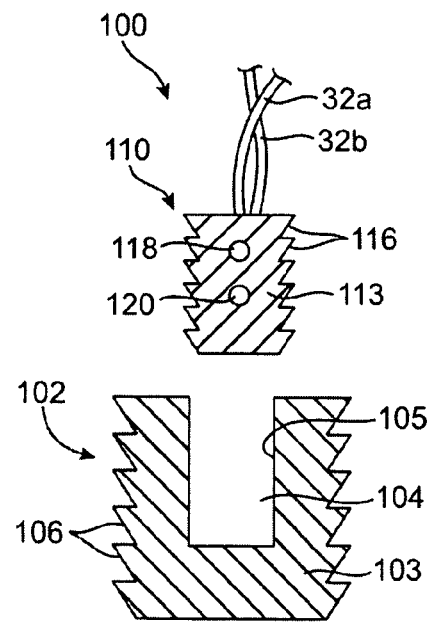
FIG. 4A is a cross-sectional view of an embodiment of an apparatus that includes bone anchor member and a plug portion.
FIG. 4B is a perspective side view of the plug portion depicted in FIG. 4A.
FIG. 4C is a perspective side view of an opposing side of the plug portion depicted in FIG. 4A.

An alternate embodiment of bone anchor 100 is described in FIGS. 4A-4C. FIG. 4A is a cross-sectional view of an embodiment of a bone anchor that includes bone anchor member and a plug portion. FIG. 4B is a side view of the plug portion depicted in FIG. 4A. FIG. 4C is a side view of an opposing side of the plug portion depicted in FIG. 4A.

Referring to FIG. 4A, bone anchor 100 includes bone anchor member 102 and plug portion 110. Bone anchor member 102 includes main body 103 having bore 104 disposed therein. Main body 103 may include cleated members 106 disposed on the outer surface thereof. The shape and dimensions of cleated members 106 is not limited to that depicted in FIG. 4A. For example, cleated members 106 may be shaped substantially similar to the cleated members 42 of bone anchor member 20. Cleated members 106 are configured to insert into a hole of a bone using a frictional force fit.

During use, after bone anchor member 102 is secured in the hole, plug portion 110 may be inserted into bore 104 of bone anchor member 102. Plug portion 110 may include cleated members 116 on the outer surface thereof. Cleated members 116 may be configured to permit the advancement of plug portion into bore 104 and allow plug portion 110 to engage and frictionally grip inner wall 105, thereby securing the plug portion 100 to bone anchor member 102.

Referring to FIGS. 4B and 4C, plug portion 110 includes first and second passages 118 and 120. First and second suture ends 32a and 32b may be coupled to plug portion 110 of apparatus 100 in a manner similar to that described in FIG. 2C. First end 32a of suture 30 is disposed through first passage 118. After exiting through first passage 118, first end 32a then transitions into loop portion 34a, forms loop 34, and transitions into loop portion 34b (e.g., as shown in FIGS. 2A-2C). Loop portion 34b transitions into second end 32b, which extends through second passage 120.

Alternatively, suture 30 may be coupled to plug portion 110 using techniques described hereinbelow with respect to FIGS. 6-8. These techniques allow the suture to be coupled to plug portion 110 without the need to thread free ends 32a and 32b through passages 118 and 120, as set forth below.

If desired, passages 118 and 120 of FIGS. 4A-4C may include cleated members 74, as described hereinabove with respect to FIG. 2C. If cleated members 74 are employed, then tissue may be secured to a bone (e.g., see FIG. 1) by individually tensioning first and second ends 32a, 32b of suture 30, as described hereinabove.

Plug portion 110 preferably includes one or more guide channels 125 disposed in a lateral surface of plug body 113. Guide channel 125 preferably is substantially similar to guide channels 50 and 52 of FIG. 2C. In FIG. 4C, guide channel 125 is configured to permit retraction of first and second suture ends 32a and 32b when plug portion 110 is secured within bore 104 by providing a clearance between the plug portion and the bone anchor member.

Alternatively, passages 118 and 120 may be substantially smooth passages, such that cleated members 74 are not employed. In this case, passages 118 and 120 permit substantially unimpeded movement of suture 30 through the passages. In operation, suture ends 32a and 32b may be individually tensioned prior to insertion of plug portion 110 into bone anchor member 102. When the tissue has been appropriately secured to the bone, plug portion 110 is then forced into bore 104 of bone anchor member 102. This causes suture ends 32a and 32b to be sandwiched between plug portion 110 and bone anchor member 102 when guide channels 125 are not present. Accordingly, the suture is secured between the two portions using a force fit.

Figures 5A, 5B, 5C:
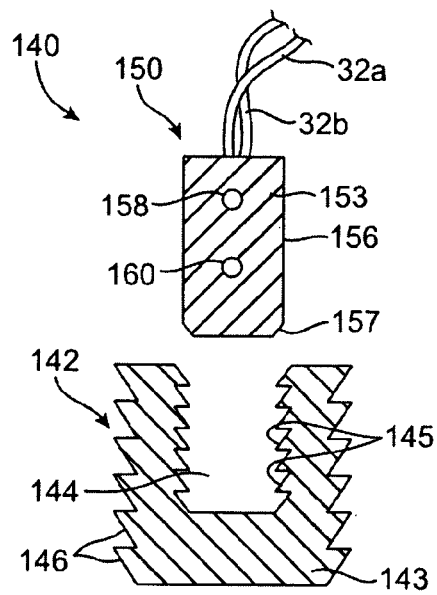
FIG. 5A is a cross-sectional view of an embodiment of a bone anchor that includes bone anchor member and a plug portion.
FIG. 5B is a perspective side view of the plug portion depicted in FIG. 5A.
FIG. 5C is a perspective side view of an opposing side of the plug portion depicted in FIG. 5A.

FIGS. 5A-5C show a further embodiment of a bone anchor apparatus. Bone anchor 140 may include bone anchor member 142 and plug portion a 150 as shown in FIG. 5A. FIG. 5B is a side view of the plug portion depicted in FIG. 5A. FIG. 5C is a side view of an opposing side of the plug portion depicted in FIG. 5A.

Referring to FIG. 5A, apparatus 140 includes bone anchor member 142 and plug portion 150. Bone anchor member 142 includes main body 143 having bore 144 disposed therein. Main body 143 may include exterior cleated members 146 and interior cleated members 145 disposed on the inner surface of bore 144. Exterior cleated members 146 are configured to insert into a hole of a bone (e.g., see FIG. 1) using a force fit, as described in earlier embodiments above.

Plug portion 150 includes main body 153. In an embodiment, main body 153 may be substantially cylindrical in shape. In an embodiment, the exterior surface 156 of main body 153 may be substantially smooth. Main body 153 may include taper 157 at the distal end thereof.

Suture 30 having first and second ends 32a, 32b is coupled to plug portion 150. A method of coupling is described hereinbelow with respect to FIGS. 6-8.

In operation, bone anchor member 142 is advanced into a hole of a bone (e.g., see FIG. 1). Exterior cleated members 146 of bone anchor member 142 permit one-way movement of the bone anchor member into the hole.

Plug portion 150 may be inserted into bore 144 of bone anchor member 142. An outer diameter of exterior surface 156 of plug portion 150 may be slightly larger than an inner diameter of bore 144. Accordingly, when plug portion 150 is urged distally, a force fit is achieved to secure plug portion 150 within the bore of bone anchor member 142.

Taper 157 of plug portion 150 facilitates the distal advancement of the plug portion with respect to bone anchor member 142. Interior cleated members 145 are configured to permit advancement of plug portion 110 into bore 144 in a distal direction only.

First and second suture ends 32a and 32b may be coupled to plug portion 150 in a manner described hereinabove with respect to FIGS. 4A-4C. Specifically, first end 32a of suture 30 is disposed through first passage 158, and forms a loop that is threaded through a tissue. Second end 32b of suture 30 extends through second passage 160.

First and second passages 158, 160 may include cleated members 74 (see FIG. 2C). If cleated members 74 are employed, then tissue may be secured to the bone by individually tensioning first and second ends 32a, 32b of suture 30. Cleated members 74 permit incremental tensioning of each suture end, and serve to lock the suture ends within their respective passages 158 and 160, as generally set forth hereinabove with respect to FIG. 2C.

Plug portion 150 includes one or more guide channels 165 disposed in a lateral surface of plug body 153, as shown in FIG. 5C. Guide channel 165 is configured to permit retraction of first and second suture ends 32a, 32b when plug portion 150 is secured within bore 144. In some embodiments guide channel 165 is substantially similar to guide channel 50 of FIG. 2C.

Alternatively, passages 158, 160 may be smooth passages, such that cleated members 74 are not employed and guide channels 165 are not present. In some embodiments, passages 158,160 may be substantially smooth. During use, suture ends 32a, 32b may be individually tensioned prior to insertion of plug portion 150 into bone anchor member 142. When tissue is appropriately secured to the bone, then plug portion 150 is forced into bore 144 of bone anchor member 142. This causes suture ends 32a, 32b to be sandwiched between plug portion 150 and bone anchor member 142. Accordingly, the suture is secured between the two portions using a force fit.

Figure 6A:
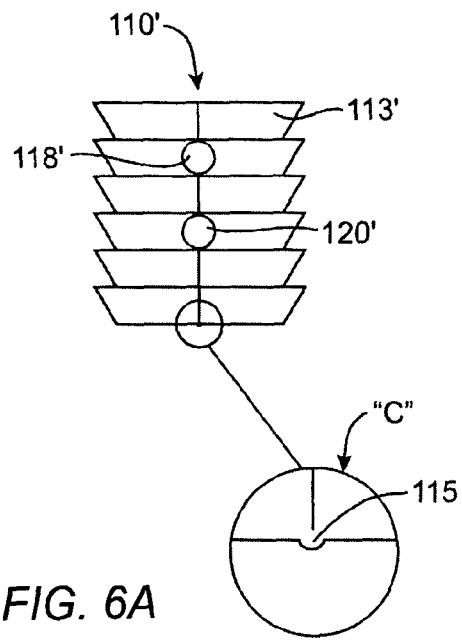
FIG. 6A is a perspective side view of an embodiment of plug portion in a closed state.
Figure 6B:
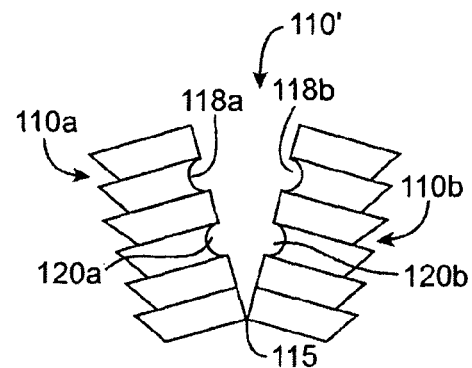
FIG. 6B is a perspective side view of the plug portion depicted in FIG. 6A in a partially open state.
Figure 6C:
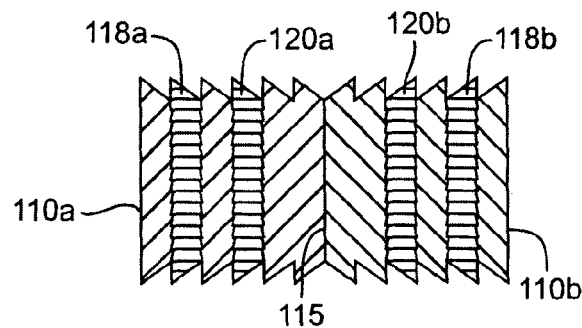
FIG. 6C is perspective a top view of the plug portion depicted in FIG. 6B.

Further embodiments of a plug portion are described in FIGS. 6A-6C. The plug portion may be used in bone anchors depicted in FIG. 4A-4C. FIG. 6A is a side view of an embodiment of plug portion in a closed state. FIG. 6B is a side view of the plug portion depicted in FIG. 6A in a partially open state. FIG. 6C is a top view of the plug portion depicted in FIG. 6B.

Plug portion 110' includes first and second plug portions 110a, 110b, which are coupled together using hinge member 115. Hinge member 115 may be integral to first and second plug portions 110a, 110b, or the hinge member may be a third element that couples two distinct portions together.

Hinge member 115 permits plug portion 110' to transition between a closed state, as shown in FIG. 6A, and a partially or fully open state, as depicted in FIGS. 6B-6C, respectively. In the open states of FIGS. 6B-6C, a first suture end may be positioned (e.g., quickly positioned by a physician) in passage 118a and a second suture end positioned in passage 120a. Alternatively, the positioning of the suture ends may be reversed (e.g., first and second suture ends may be placed in passages 120b and 1118b, respectively).

With the suture ends in place, plug portion 110' may be transformed into a closed state, depicted in FIG. 6A, by rotating first and second plug portions 110a, 110b together. In the closed state, first and second plug portions 110a, 110b form first and second passages 118', 120'. With the sutures ends disposed in their respective passages, the apparatus may be actuated to secure tissue to bone.

As will be apparent to one skilled in the art, hinge member 115 serves to ensure proper alignment of first and second plug portions 110a, 110b in the closed state. If desired, a securing means, such as protrusion 55 and pocket 59 of FIGS. 3A-3E, may be employed to secure plug portions 110a and 110b. Further, as will be apparent to one skilled in the art, the securing means may be reversible, such that plug portions may be separated, as shown in FIGS. 6B-6C, to reposition the suture ends.

Figure 7:
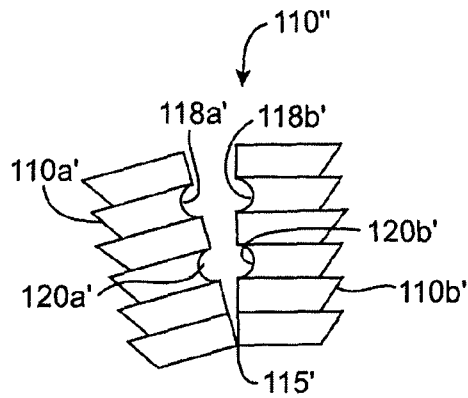
FIG. 7 is perspective side view of an embodiment of a plug portion in a partially open state.

FIG. 7 depicts a perspective view of a plug in a partially opened state. Plug portion 110" includes first and second plug portions 110a', 110b', which have different sizes. Hinge member 115 is offset from the center of plug portion 110". Further, passage portions 118a' and 120a' of plug portion 110a' are each less than 180 degrees. By contrast, passage portions 118b' and 120b' of plug portion 110b' are each greater than 180 degrees.

During use, a first suture end may be positioned in passage portion 118b', and then a second suture end is placed in passage portion 120b'. Since these passage portions are each greater than 180, the suture ends may be pressed into the passage portions. Using such a method the suture ends remain at least partially in place. With the suture ends in place, plug portion 110" is transformed to a closed state. In the closed state, passage portions 118a', 118b' form a first one-way, 360-degree passage through which the first suture end may pass. The second passage portions 120a', 120b' form a second one-way, 360-degree passage through which the second suture end may pass.

Figure 8A:
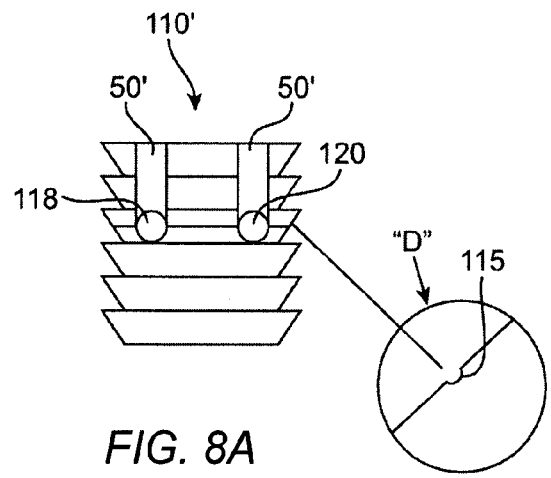
FIG. 8A is a perspective side view of an embodiment of a plug.
Figure 8B:
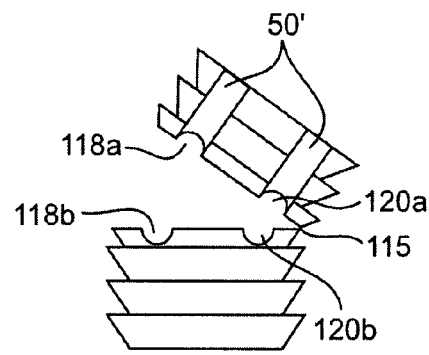
FIG. 8B is a perspective side view of the plug depicted in FIG. 8A in a partially open state.
Figure 8C:
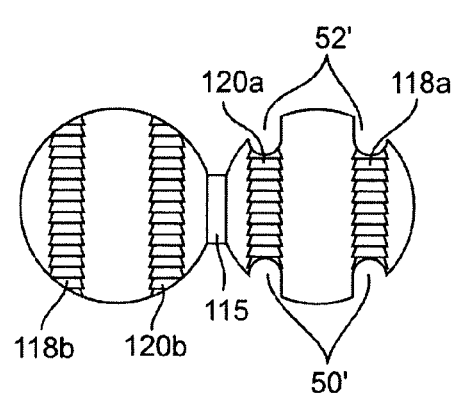
FIG. 8C is a perspective top view plug depicted in FIG. 8A in a fully open state.

Referring to FIGS. 8A-8C, yet another embodiment of a plug is described. FIG. 8A is a side view of an embodiment of a plug. FIG. 8B is a side view of the plug depicted in FIG. 8A in a partially open state. FIG. 8C is a top view plug depicted in FIG. 8A in a fully open state.

Hinge member 115 is located on a lateral surface of plug portion 110''', as opposed to on the distal end of the plug portion, as shown in detail "D". Like the embodiment of FIGS. 6A-6C, the embodiment of FIGS. 8A-8C facilitates coupling of the suture to the plug portion. During use, threading of the suture through passages 118 and 120 of the plug portion is not required.

As will be apparent to one skilled in the art, passage portions 118a and 120a may be larger than passage portions 118b and 120b, respectively, as described with respect to FIG. 7 hereinabove.

Figure 9:
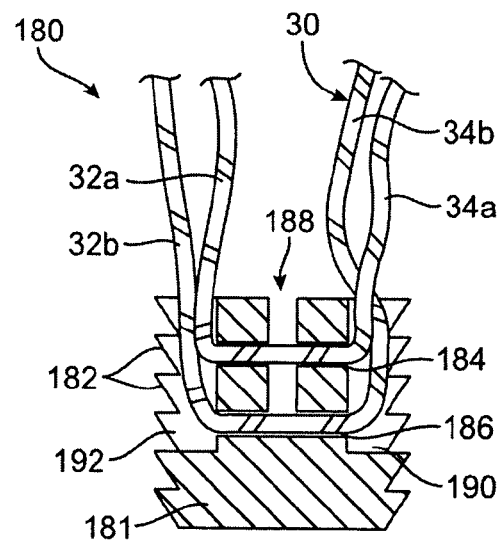
FIG. 9 is a cross-sectional view of an embodiment of a bond anchor having at least one adhesive delivery channel.

Referring to FIG. 9, an embodiment of a bone anchor is described. Bone anchor member 180 is similar to bone anchor member 20 of FIGS. 2A-2C, except as noted hereinbelow. Cleated members 182 of bone anchor member 180 are similar to cleated members 42 of bone anchor member 20, as described hereinabove, and facilitate anchoring of bone anchor member 180 within a hole of a bone. Further, guide channels 190 and 192 are similar to guide channels 50 and 52 of FIGS. 2A-2C.

Unlike the embodiments described hereinabove, bone anchor member 180 includes at least one adhesive delivery channel 188, which is provided within main body 181. Adhesive delivery channel 188 may be formed by drilling a hole into an upper surface of main body 181, such that the hole extends through first passage 184 and second passage 186. As will be apparent to one skilled in the art, however, channel 188 may be formed using other known techniques.

First and second passages 184 and 186 may include cleated members 74 of FIG. 2C, thereby permitting one-way movement of suture ends 32a and 32b through the passages. Alternatively, passages 184 and 186 may include substantially smooth inner surfaces that permit movement of suture 30 through the passages in either direction.

After bone anchor member 180 is secured in a hole the bone, the position of tissue relative to the bone may be approximated by individually tensioning first and second ends 32a, 32b of suture 30, as described extensively above an incorporated herein. When the tissue has the desired placement, an adhesive may be delivered to adhesive delivery channel 188. The delivery of an adhesive to channel 188 may be facilitated using a needle-like tube (not shown) disposed within a working cannula. The needle-like tube has a distal opening that may be placed in close proximity to, or within, adhesive delivery channel 188 to deliver an adhesive thereto.

The adhesive is allowed to flow distally through adhesive delivery channel 188 and into portions of first and second passages 184 and 186. The adhesive may contact at least a portion of suture 30 positioned in corresponding regions of first and second passages 184 and 186, thereby locking the suture in place. As will be apparent to one skilled in the art, although one adhesive delivery channel 188 is depicted in FIG. 9, multiple adhesive delivery channels may be employed to secure the suture, irrespective of whether cleated members 74 are employed.

Figure 10A:
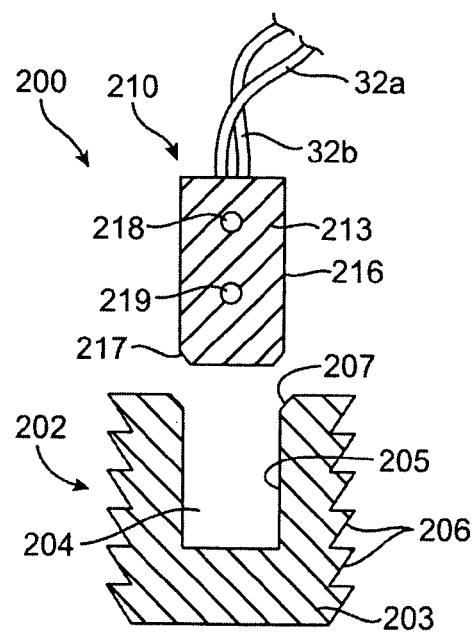
FIG. 10A is a cross-sectional view of a bone anchor that includes a bone anchor member and a plug portion.

Referring to FIG. 10A, apparatus 200 includes bone anchor member 202 and plug portion 210. Apparatus 200 is similar to apparatus 140 of FIGS. 5A-5C, except as noted below.

Bone anchor member 202 includes main body 203 having bore 204 disposed therein. Main body 203 of bone anchor member 202 includes exterior cleated members 206, which are configured to be inserted into a hole of a bone (e.g., see FIG. 1) using a force fit, as described hereinabove.

Plug portion 210 may be substantially cylindrical in shape and includes main body 213. Main body 213 has smooth exterior surface 216 and taper 217. Optionally, taper 217 may be formed at the distal end of main body 213.

Suture 30 having first and second ends 32a, 32b is coupled to plug portion 210, preferably in a manner described hereinabove with respect to FIGS. 6-8.

The outer diameter of main body 213 may be sized slightly larger than an inner diameter of bore 204. The size of diameter is selected to allow main body 213 of plug portion 210 to be distally advanced into bore 204 when forced. Taper 207 of bone anchor member 202 is facilitates advancement of plug portion 210 into bore 204.

Figure 10B:
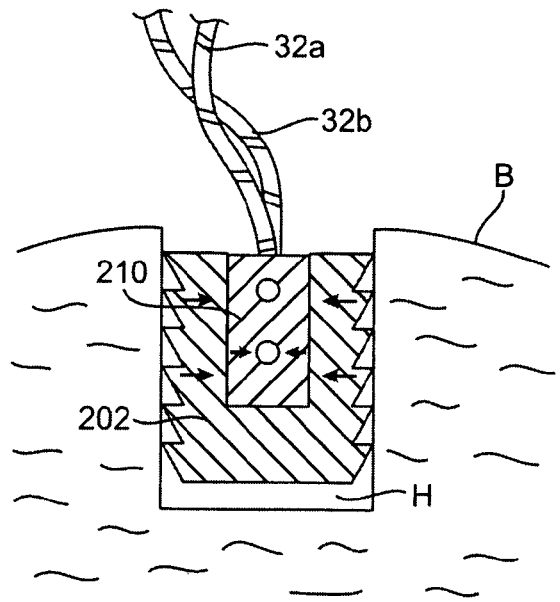
FIG. 10B is a perspective view of the bone anchor of FIG. 10A positioned in a hole of a bone.

In operation, bone anchor member 202 is secured within a hole of a bone when the bone anchor member is distally advanced into the hole, as depicted in FIG. 10B. Exterior cleated members 206 of bone anchor member 202 permit one-way movement of the bone anchor member into the hole.

Plug portion 210 is advanced distally into bore 204 of bone anchor member 202 and secured therein using a force fit, as described hereinabove. At this time, surrounding regions of the bone may apply a compressive force upon bone anchor member 202, as indicated by the larger directional arrows in FIG. 10B. This compressive force upon bone anchor member 202 in turn causes compression upon plug portion 210, as indicated by the smaller directional arrows in FIG. 10B, thereby securely retaining the plug portion within bore 204.

In some embodiments, passages 218 and 219 may include cleated members 74 as described hereinabove with respect to FIG. 2C. Alternatively, passages 218 and 219 may include substantially smooth interior surfaces that permit advancement of suture 30 in either direction.

In certain embodiments, the position of the tissue relative to the bone may be approximated by individually tensioning suture ends 32a and 32b prior to insertion of plug portion 210 into bone anchor member 202. In some embodiments, the tissue position is approximated when passage 219 is disposed just above bore 204. Once the desired positioning of the tissue is achieved, plug portion 210 is advanced distally into bore 204, thereby locking the suture. Specifically, the suture will be sandwiched between exterior surface 216 of plug portion 210 and inner wall 205 of bone anchor member 202.

Figure 11:
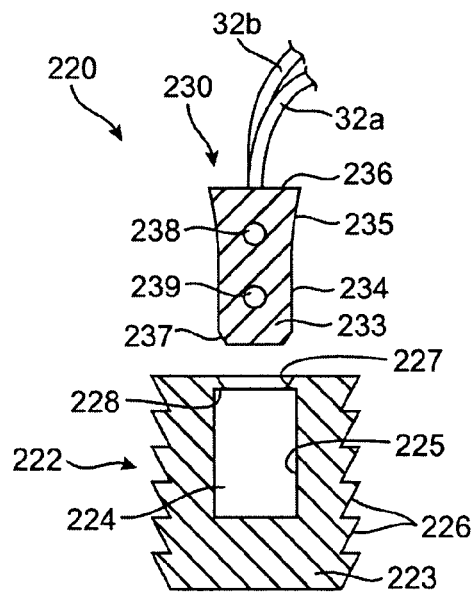
FIG. 11 is a cross-sectional view of an embodiment of a bone anchor that includes a bone anchor member and a plug portion.

Referring to FIG. 11, apparatus 220 may include a bone anchor member 222 and a plug portion 230. Apparatus 220 is similar to apparatus 200 of FIGS. 10A-10B, except as noted below.

Bone anchor member 222 includes main body 223 having bore 224 disposed therein, as depicted in FIG. 11. Further, main body 223 includes exterior cleated members 226, which are configured to be inserted into a hole of a bone (e.g., see FIG. 1) using a force fit, as described hereinabove. Bone anchor member 222 includes a proximal protrusion having inward taper 227. Proximal stop 228 is formed between inward taper 227 and inner wall 225 of bone anchor member 222.

Plug portion 230 includes main body 233 having proximal region 235, central region 234 and tapered distal region 237. Tapered distal region 237 is sized to pass through taper 227 of bone anchor member 222 when a distally directed force is applied to plug portion 230. When further force is applied, central region 234 of plug portion 230 is advanced into bore 224 via taper 227. When further force is applied to plug portion 230, proximal region 235 is advanced past taper 227. Once proximal region 235 is fully inserted into bore 224, proximal stop 228 is configured to abut proximal edge 236 of plug portion 230, thereby securing the plug portion within bone anchor member 222.

As will be apparent to one skilled in the art, apparatus 220 may further include any of the other features described above with respect to the embodiments of FIGS. 2-10. For example, passages 238 and 239 may include cleated members 74 of FIG. 2C, or alternatively may include substantially smooth interior surfaces. Further, the operation of apparatus 220 preferably is substantially similar to the methods described hereinabove with respect to the embodiments of FIGS. 2-10.

Figure 12:
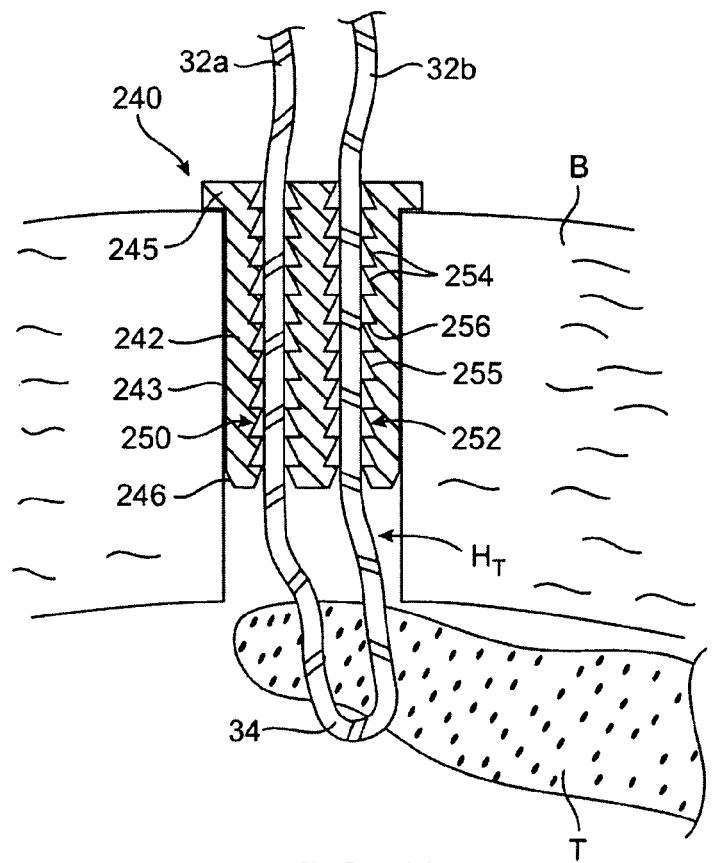
FIG. 12 is perspective side view of an embodiment of a bone anchor positioned in a bone with two openings.

In some embodiments, a bone anchor may be positioned in bone through hole $H_T$, which has two openings to the surface of the bone. Referring to FIG. 12, bone anchor 240 is similar to bone anchor member 20 of FIGS. 1-2, but is configured for use in applications where through hole $H_T$ is employed.

Bone anchor 240 includes main body 242 having proximal and distal ends. Flange 245 disposed at the proximal end and taper 246 formed at the distal end of main body 242. Main body 242 includes exterior surface 243 disposed between flange 245 and taper 246.

Bone anchor 240 includes first and second passages 250 and 252, each having a plurality of cleated members 254. Each of the cleated members includes angled sections 255 and substantially orthogonal sections 256, which are disposed adjacent one another thereby forming a cleated shape, as described hereinabove with respect to cleated members 74 of FIG. 2C.

During use, a loop of suture 30 may be coupled through tissue T first, with free ends 32a and 32b extending from the tissue. Free end 32a then is threaded through first passage 250 in a proximal direction. Free end 32b is threaded through second passage 252, also in a proximal direction. The suture may be threaded through passages 250, 252 and tissue T by arthroscopically operating on one or both sides of bone B.

As will be apparent to one skilled in the art, suture 30 may be coupled between tissue T and bone anchor 240 using other arthroscopic threading techniques, so long as the suture ultimately is situated in a manner depicted in FIG. 12.

Once the suture is threaded as shown in FIG. 12, first and second suture ends 32a and 32b may be proximally retracted, one at a time, to approximate the position of tissue T with respect to bone B. As the suture ends are tensioned, flange 245, which has an outer diameter larger than the diameter of through hole $H_T$, abuts bone B. The system becomes tensioned because flange 245 and tissue T are drawn against the bone from opposing directions.

In accordance with one aspect of the present invention, cleated passages 250 and 252 are configured to permit one-way movement of first and second suture ends 32a and 32b, respectively. For example, when first end 32a is pulled in a proximal direction, angled sections 255 permit movement of the suture end in the proximal direction. However, suture end 32a is inhibited from distally advancing within passage 250. The use of two separate passages allows each end of the suture to be separately tensioned, which is often desirable when tissue T is torn irregularly.

As will be apparent to one skilled in the art, the methods described in FIG. 12 may be accomplished using a separate bone anchor member and plug portion. For example, the principles of the embodiments in FIGS. 4-5 and FIGS. 10-11, in which separate bone anchor and plug portions are employed, may be implemented in lieu of one-piece bone anchor 240.

Further, the suture securing methods described in FIG. 12 may be accomplished using substantially smooth passages 250 and 252. Where substantially smooth passages are employed, an interference fit or an adhesive may be employed in lieu of the cleated passages to facilitate securing of the suture. The interference fit or adhesive may be used, for example, as described hereinabove with respect to the embodiments of FIGS. 4-5 and FIGS. 10-11.

FIG. 13A is a cross-sectional view of an embodiment of an apparatus that includes a bone anchor member and a plug portion. As shown in FIG. 13A, apparatus 270 includes bone anchor member 272 and plug portion 280. Bone anchor member 272 includes main body 273 having bore 274 disposed therein. Main body 273 includes exterior cleated members 276, which are configured to be inserted into a hole of a bone (e.g., see FIG. 1) using a force fit, as described hereinabove. Bone anchor member 272 includes a proximal protrusion having inward taper 277. Proximal stop 278 is formed between inward taper 277 and an inner wall of bone anchor member 272.

Bone anchor member 272 includes first and second spring elements 292a and 292b, which are disposed at a distal region of bore 274. First and second spring members 292a and 292b may be integrally formed with bone anchor body 273, or may be separate elements coupled to body 273. First and second spring elements 292a and 292b may be deformed to accommodate plug portion 280 within bore 274, and also to enable locking and unlocking of a suture (not shown in FIGS. 13A-13C) used in conjunction with apparatus 270. As will be apparent to one skilled in the art, one or more spring elements may be employed.

First and second passages 298 and 299 extend laterally through main body 273 of bone anchor member 272. First and second passages 298 and 299 are configured to selectively align with first and second passages 288 and 289 of plug portion 280, for the purposes described hereinafter.

Plug portion 280 of apparatus 270 includes main body 283 having proximal and distal ends. The proximal end includes flange 284. Taper 286 is disposed between flange 284 and main body 283. Distal taper 287 is disposed at the distal end of plug portion 280.

Plug portion 280 includes first and second passages 288 and 289, which extend laterally through main body 283. In some embodiments, first and second passages 288 and 289 include substantially smooth interior surfaces.

FIG. 13B illustrates use of apparatus 270. First, plug portion 280 is inserted into bore 274 of bone anchor member 272, using insertion tool 294. When an appropriate force is applied to plug portion 280, tapered distal end 287 passes through taper 277 of bone anchor member 272. When further force is applied, a central region of plug portion 280 is advanced into bore 274 via taper 277. When further force is applied to plug portion 280, the proximal region having taper 286 and flange 284 is then advanced past taper 277.

When plug portion 280 is fully inserted into bore 274, first and second spring elements 292a and 292b are inclined to urge plug portion 280 in a proximal direction, to allow flange 284 to abut proximal stop 278 (see FIG. 13C). However, when a sufficient distally directed force is applied to plug portion 280, (e.g., using insertion tool 294) first and second spring elements may be deformed distally (see FIG. 13B).

Insertion tool 294 may be a rod or other substantially rigid member configured to transfer a distally directed force from a physician to plug portion 290. In some embodiments, insertion tool 294 is engages mating slot 295, as shown in FIG. 13B.

The provision of distally directed force acting on plug portion 280 causes first and second passages 288 and 289 to become substantially aligned with first and second passages 298 and 299 of bone anchor member 27, respectively, as shown in FIG. 13B. At this time, a suture may be threaded through aligned first passages 288 and 298. The suture may be threaded through a tissue, as described hereinabove, and then threaded back through aligned second passages 289 and 299. First suture end 32a extends through first passages 288 and 298, while second suture end 32b extends through second passages 289 and 299.

Once the suture is coupled to apparatus 270, apparatus 270 is inserted into a hole of a bone under arthroscopic guidance. Cleated members 276 secure apparatus 270 within the hole, as described hereinabove. At this time, first and second suture ends 32a and 32b will extend outside of the arthroscopic field of vision.

First and second suture ends 32a and 32b may be selectively tensioned to approximate the positioning of the tissue with respect to the bone when first and second passages 288 and 289 are aligned with first and second passages 298 and 299, respectively. During tensioning of the suture ends, insertion tool 294 urges plug portion distally to cause the passages to align, as shown in FIG. 13B.

When a desired positioning of the tissue is achieved, the force applied to plug portion 280 is removed (e.g., by proximally retracting insertion tool 294, as shown in FIG. 13C). At this time, first and second spring elements 292a and 292b are inclined to bias proximally, thereby urging flange 284 of plug portion 280 against proximal stop 278 of bone anchor member 272. This movement of plug portion 280 with respect to bone anchor member 272 causes a misalignment between first passage 288 of plug portion 280 and first passage 298 of bone anchor member 272. Also, a misalignment occurs between second passages 289 and 299. Accordingly, the misalignments cause first suture end 32a to become pinched between first passages 288 and 298, while second suture end 32b is pinched between second passages 289 and 299. These misalignments lock the suture in place.

If it becomes necessary to adjust the positioning of the tissue with respect to a bone during use, then insertion tool 294 may be inserted into mating slot 295, as shown in FIG. 13B, to urge plug portion 280 distally. As described hereinabove, when first and second passages of plug portion 280 and bone anchor member 272 are aligned (see FIG. 13B), suture ends 32a and 32b may be manipulated to adjust the positioning of the tissue.

FIG. 14 is a perspective cross-sectional view of an embodiment of an apparatus that includes a bone anchor member and a plug portion. The apparatus is similar to the apparatus described in FIG. 13, except as described. Bone anchor member 272' includes spring element 292' disposed at a distal end of main body 273. Spring element 292' includes a distally concave configuration having a central region 293.

Bone anchor member 272' is used in conjunction with plug portion 280 in a manner similar to that described hereinabove with respect to FIGS. 13A-13C. Specifically, after plug portion 280 is inserted into bore 274, the provision of a further distally-directed force acting on plug portion 280 causes central region 293 of spring element 292' to be deformed in a distal direction. When the central region of spring element 292' is deformed distally, first and second passages 288 and 289 of plug portion 280 are substantially aligned with first and second passages 298 and 299 of bone anchor member 272', respectively. In this state, first suture end 32a may move substantially unimpeded through aligned first passages 288 and 298, while second suture end 32b may move through aligned second passages 289 and 299, respectively, as described hereinabove with respect to FIG. 13B.

When a desired positioning of tissue is achieved, the force imposed upon plug portion 280 is removed (e.g., by proximally retracting insertion tool 294, as described in FIG. 13C) and central region 293 of spring elements 292' returns in a proximal direction to its preferred orientation. This causes flange 284 of plug portion 280 to be urged against proximal stop 278 of bone anchor member 272'. As described hereinabove, the movement of plug portion 280 with respect to bone anchor member 272' causes a misalignment between first passages 288 and 298, and also a misalignment between second passages 289 and 299. These misalignments pinch suture ends 32a and 32b to lock the suture in place.

Figure 15A:
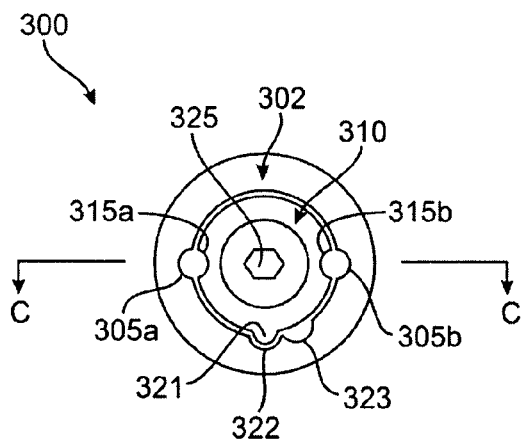
FIG. 15A is perspective top view of top view of an embodiment of a bone anchor that includes a bone anchor and a plug portion.
Figure 15B:
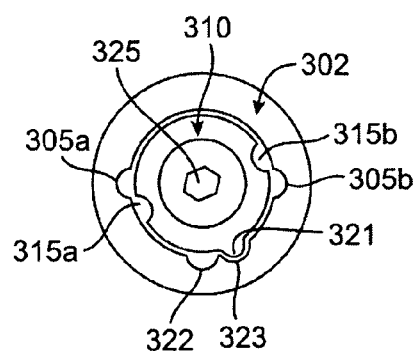
FIG. 15B is a cross-sectional view of the bone anchor depicted in FIG. 15A along line 15C-15C.
Figure 15C:
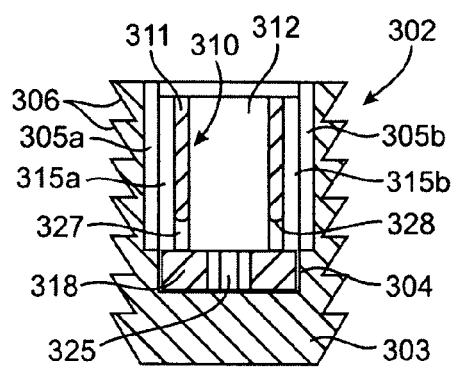
FIG. 15C is perspective top view of the bone anchor of FIG. 15A in a locked state.

Referring to FIG. 15, an embodiment of an apparatus that includes a bone anchor member and a plug portion is described. FIG. 15A is top view of top view of an embodiment of an apparatus that includes a bone anchor and a plug portion. FIG. 15B is a cross-sectional view of the bone anchor depicted in FIG. 15 A along line 15C-15C. FIG. 15C is top view of the bone anchor depicted in FIG. 15A in a locked state.

Apparatus 300 includes bone anchor member 302 and plug portion 310. Bone anchor member 302 is similar to the bone anchor members described hereinabove and includes main body 303 having plurality of cleated members 306, which are configured to anchor plug portion 302 within a hole of a bone (e.g., see FIG. 1). Bone anchor member 302 includes central bore 304, which is configured to receive plug portion 310.

Plug portion 310 of apparatus 300 includes main body 311 having distal region 318 and central bore 312, as shown in FIG. 15B. Main body 311 has an outer diameter that is slightly smaller than an inner diameter of bore 304. Accordingly, plug portion 310 is configured for circumferential rotation within bore 304 of bone anchor member 302.

Bone anchor member 302 includes first and second semi-circular channels 305a and 305b, which are formed at diametrically opposing surfaces of main body 303, as shown in FIGS. 15A and 15B. Further, plug portion 310 includes first and second semi-circular channels 315a and 315b, which are formed at diametrically opposing surfaces on main body 311, as shown in FIGS. 15A and 15B.

Apparatus 300 also includes actuation knob 321, which is disposed on an outer surface of plug portion 310, as shown in FIG. 15A. Actuation knob 321 is configured to be disposed within first recess 322 of bone anchor member 302 in an unlocked state, and disposed within second recess 323 in a locked state.

When actuation knob 321 is disposed within first recess 322, first and second semi-circular channels 305a and 305b of bone anchor member 302 are aligned with first and second semi-circular channels 315a and 315b of plug portion 310, respectively, thereby forming first and second circular channels, as shown in FIGS. 15A and 15B.

When actuation knob 321 is disposed within second recess 323, first and second semi-circular channels 305a and 305b of bone anchor member 302 are not aligned with corresponding channels 315a and 315b of plug portion 310, as shown in FIG. 15C.

Figure 16:
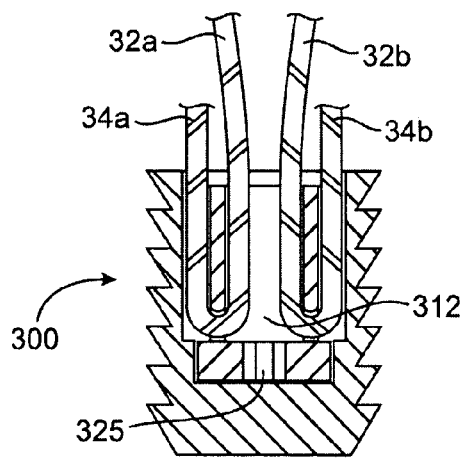
FIG. 16 is a perspective view illustrating use of a suture in connection with the bone anchor depicted in FIGS. 15A-15C.

During use, suture 30 is coupled to apparatus 300 in a manner shown in FIG. 16. Specifically, first suture end 32a extends through central bore 312 of plug portion 310. First suture end 32a passes through aperture 327 in plug portion 310 (see FIG. 15B) and transitions into loop portion 34a. Loop portion 34a is threaded through the first circular channel formed by semi-circular channels 305a and 315a.

Loop portion 34a then is threaded through a tissue and transitions into loop portion 34b. Loop portion 34b is threaded through the second circular channel formed by semi-circular channels 305b and 315b. Loop portion 34b passes through a second aperture 327 and transitions into second suture end 32b. Second suture end 32b extends through central bore 312 of plug portion 310.

During use, first and second suture ends 32a and 32b may be selectively tensioned when actuation knob 322 is disposed within first recess 322, as shown in FIGS. 15A-15B. This is because first and second semi-circular channels 305a and 305b of bone anchor member 302 are aligned with first and second semi-circular channels 315a and 315b of plug portion 310, respectively, to form the first and second circular channels through which the suture can freely pass.

It should be noted that, as first and second ends 32a and 32b are individually tensioned, rounded edges 328 of plug portion 310 (see FIG. 15B) serve to reduce the shear stresses imposed upon the suture ends as they pass through apertures 327.

To lock the suture in place, plug portion 310 is rotated with respect to bone anchor member 302 to cause actuation knob 321 to be advanced into second recess 323. The rotation of plug portion 310 may be achieved by inserting an actuation tool such as a hexagonal key (not shown) into mating slot 325. Once knob 321 is secured within second recess 323, as shown in FIG. 15C, the suture will be locked in place because the misaligned semi-circular channels pinch the first and second ends of the suture.

The positioning of tissue may be optimized (e.g., tweaked) with respect to bone after the suture has been locked, the actuation tool may be inserted into mating slot 325 and force applied to cause knob 322 to rotate in an opposing direction into first recess 322. As described above, this forms two fully circular channels through which the suture may be advanced or retracted to facilitate positioning of the tissue with respect to the bone.

FIGS. 17A and 17B depict cross-sectional views of embodiments of a bone anchor in unlocked and locked states, respectively. Referring to FIG. 17A, bone anchor member 340 includes main body 343 having proximal and distal regions. Bone anchor member 340 includes a plurality of cleated members 346, and opposing guide channels 348 and 349. In some embodiments, guide channels 348 and 349 are similar to guide channels 50 and 52 of FIG. 2C.

Bone anchor member 340 includes at least one passage 352 and flexible member 350. Passage 352 extends laterally through main body 343. Flexible member 350 is disposed proximal to passage 352. Flexible member 350 has a relaxed configuration in which it assumes a convex shape (e.g., bowed away from passage 352). In the relaxed configuration, shown in FIG. 17A, there is sufficient clearance between flexible member 350 and passage 352 to permit suture 30 to move substantially unimpeded through the passage.

In use, before bone anchor member 340 is inserted into a hole of a bone, first suture end 32a is passed through passage 352. The first suture end then becomes loop portion 34a, which is threaded through the tissue, as described hereinabove. Loop portion 34a extends through the tissue to become loop portion 34b. Loop portion 34b passes back through passage 352 and becomes second suture end 32b. First and second suture ends 32a and 32b extend outside of the arthroscopic site and may be individually tensioned during use.

After suture 30 is coupled to apparatus 340 and the tissue, bone anchor member 340 is advanced distally into a hole of a bone (e.g., see FIG. 1), whereby cleated members 346 serve to anchor the device in the hole. As described above, first and second suture ends 32a and 32b may be individually tensioned to approximate the positioning of the tissue with respect to the bone. During this time, no external forces are applied to flexible member 350, thereby permitting movement of the suture within passage 352.

Once a desired tissue positioning is achieved, the suture may be locked in place by apply a distally directed force upon flexible member 350, as depicted in FIG. 17B. Flexible member 350 preferably assumes a concave shape in which distal knob 354 is urged towards corresponding pocket 355 in bone anchor member 342. The distally directed force locks the suture in place by pinching the suture and inhibiting its movement within passage 352.

As will be apparent to one skilled in the art, any number of mechanisms may be employed to apply a distally directed force upon flexible member 350, and further, to lock the flexible member in the concave position depicted in FIG. 17B. For example, a plug may be inserted into bore 358, and then wedged against flexible member 350 to hold the flexible member in place. Alternatively, bone anchor member 340 may include taper 277 and proximal stop 278 (see FIG. 17A) to allow the plug to remain in place within bore 358. In either case, the plug serves to apply a compressive force to hold the suture in the locked state.

Alternatively, the flexible member may be "bi-stable," such that the flexible member has only two stable states. In the first state, the flexible member is positioned as shown in FIG. 17A. When a sufficient distally directed force is applied, the flexible member is configured to "snap" from the first state into a second state, as shown in FIG. 17B. There are no stable positions between the first and second state. Accordingly, the flexible member is either provided in a locked or unlocked state. Means for applying a proximally-directed force to the flexible member may be used to cause the flexible member to snap from the second state, shown in FIG. 17B, to the first state, shown in FIG. 17A, thereby unlocking the device.

In some embodiments, a threaded member may be used to hold the suture in a locked state. As shown in FIGS. 18A-18B, threaded cap 360 has exterior thread 361, which is adapted to engage grooved interior section 371 of bore 358'. In certain embodiments, threaded cap 360 includes a proximal region having mating slot 365 and a distal region having distal protrusion 362.

In an unlocked state, threaded cap 360 is situated proximally within bore 358', as shown in FIG. 18A. To lock the suture in place, locking tool 375 may be inserted into mating slot 365 and then rotated clockwise to advance threaded cap in a distal direction (e.g., in a manner similar to tightening a screw). This causes a distal region of threaded cap 360, and distal protrusion 362, to urge flexible member 350 distally, thereby impinging upon a suture length disposed through passage 352. This locks the suture in place.

If re-adjustment of the suture, then locking tool 375 may be rotated counterclockwise within mating slot 365 to proximally retract the threaded cap. This will remove the forces imposed upon the suture, as depicted in FIG. 18A.

In some embodiments, flexible member 350 is omitted entirely. In this case, threaded cap 360 may directly pinch the suture in passage 352 to lock the suture in place.

Referring now to FIGS. 19A-19B, an alternative embodiment of the bone anchor of FIGS. 17A-17B is described. Operation of bone anchor member 340" is substantially the same as that of bone anchor 340, with the main exception that locking member 380 is provided in lieu of flexible member 350.

Locking member 380 includes cylindrical body 381, which is configured to be confined within recess 391 of main body 343", as shown in FIG. 19A. Locking member 380 includes distal protrusion 382, which is configured to extend at least partially through aperture 390 of main body 343".

First and second support members 383a and 383b are disposed beneath cylindrical body 381, and may be formed integrally with locking member 380. As shown in FIG. 19A, the first and second support members 383a and 383b rest on support ledge 395 of main body 343", thereby elevating locking member 380 within recess 391.

During use, suture 30 is secured to a tissue and disposed through passage 352", as described hereinabove with respect to FIGS. 17A-17B. Bone anchor member 340" then is advanced distally into a hole of a bone (e.g., see FIG. 1), such that cleated members 346 anchor the device in the hole.

When locking member 380 is elevated within recess 391, distal protrusion 382 may not substantially extend into passage 352", thereby permitting movement of the suture within passage 352". At this time, first and second suture ends 32a and 32b may be individually tensioned to approximate the positioning of the tissue with respect to the bone.

Once a desired positioning is achieved, the suture may be locked in place by any number of techniques that cause first and second support members 383a and 383b to be lowered or eliminated, thereby lowering cylindrical body 381 within recess 391 and urging distal protrusion 382 towards corresponding pocket 355", as depicted in FIG. 19B. The distally directed force applied by distal protrusion 382 secures the suture in place.

In certain embodiments, first and second support members 383a and 383b may be fused with support ledge 395 of main body 343". In some embodiments, ultrasonic energy is delivered to a proximal surface of locking member 380, via bore 358", using techniques that are known in the art. The provision of ultrasonic energy causes first and second support members 383a and 383b to fuse with support ledge 395, thereby lowering locking device 380 and locking the suture disposed within passage 352" in place.

In the embodiments of FIGS. 17-19, while only one passage 352 is depicted, it will be apparent to one skilled in the art that a second passage may be provided, (e.g., disposed adjacent to the first passage). If two adjacent passages 352 are provided, then the suture can be threaded through the first passage, through the tissue, and threaded back through the second passage.

Further, it will be apparent to one skilled in the art that an adhesive, for example, cyanoacrylate, epoxy, bone cement and so forth, may be employed in conjunction with any of the embodiments described in FIGS. 17-19. Such an adhesive may be used in conjunction with apparatus including, but not limited to, flexible member 350, threaded cap 360, locking member 380, and any associated components.

FIGS. 20A and 20B are, respectively, a top-sectional view and a side view of embodiments of a locked state of an apparatus that includes a bone anchor and a plug portion. FIGS. 21A and 21B are, respectively, a top-sectional view and a side view depicted in FIGS. 20A-20B in a locked state. Apparatus 400 (see FIG. 20A) includes bone anchor member 402 and plug portion 410.

Bone anchor member 402 includes main body 403 having cleated members 406, which are configured to secure bone anchor member 402 in a hole of a bone, as described hereinabove. Bone anchor member 402 also includes first and second passages 408 and 412, which extend laterally through main body 403.

Bone anchor member 402 further includes guide channels 409a, 409b, 413a and 413b, which are disposed in exterior surfaces of main body 403. The guide channels preferably are similar to guide channels 50 and 52 of FIGS. 2A-2C, except that four guide channels are employed in the present embodiment.

In use, first suture end 32a passes through guide channel 409a, through passage 408 and through guide channel 409b. The first suture end then transitions into loop 34, which is threaded through a tissue. Loop 34 of suture 30 then transitions into second suture end 32b. Second suture end 32b passes through guide channel 413b, through passage 412, and through guide channel 413a. Accordingly, the suture is coupled between the tissue and apparatus 400.

Plug portion 410 having main body 411 is configured to be disposed within a central bore of bone anchor member 402. Plug portion 410 includes actuation knob 422, which is configured to be disposed in first recess 423 of bone anchor member 402 in an unlocked state, and disposed within second recess 424 in a locked state.

In the unlocked state, (e.g., when knob 422 is disposed within first recess 423) plug portion 410 is oriented such that main body 411 does not substantially overlap with first and second passages 408 and 412 of bone anchor member 410.

In some embodiments, first and second ends 32a and 32b of suture 30 are selectively tensioned when knob 422 is disposed within first recess 423. This is because first and second passages 408 and 412 provide a substantially unimpeded circular channel within which the suture can pass.

To lock the suture in place, plug portion 410 is rotated to cause knob 422 to be advanced into second recess 424. The rotation of plug portion 410 with respect to bone anchor member 402 may be achieved by inserting an actuation tool (e.g., a rectangular key) into mating slot 427. Once knob 422 is secured within second recess 424, the suture is locked in place because main body 411 of plug portion 410 impinges upon passages 408 and 412.

To adjust (e.g., tweak) the positioning of the tissue with respect to the bone after the suture is in the locked state, the actuation tool may be inserted into mating slot 427 to cause knob 422 to rotate back into first recess 423 (see FIGS. 20A-20B). This removes the compressive forces imposed upon the suture, to allow the first and second ends of the suture to be individually tensioned, thus facilitating re-positioning of the tissue.

FIGS. 22A and 22B are cross-sectional views of an embodiment of an apparatus that includes a bone anchor member and a plug portion.

Referring to FIG. 22A apparatus 440 includes bone anchor member 442 and plug portion 450. Bone anchor member 442 includes main body 443 having cleated members 446, which are configured to secure bone anchor member 442 in a hole of a bone (e.g., see FIG. 1). Further, bone anchor member 442 includes central bore 444 and circumferential protrusion 449, which is disposed near a distal end of bore 444.

Plug portion 450 has main body 451 having proximal and distal regions. The proximal region includes first and second guide channels 456 and 457, which are recessed in opposing lateral surfaces of main body 451. The distal region of main body 451 includes circumferential recess 453 and distal taper 454. Plug portion 410 also has a central region having passage 448 disposed laterally therethrough.

Before plug portion 450 is inserted into bore 444, first suture end 32a is passed through passage 448. The first suture end then becomes loop portion 34a, which is threaded through a tissue. Loop portion 34a extends through the tissue to become loop portion 34b. Loop portion 34b passes back through passage 448 and becomes second suture end 32b. First and second suture ends 32a and 32b may be manipulated during use.

Alternatively, as described hereinabove, a central region of suture 30 may be threaded through the tissue, and the free ends of the suture then may be passed through passage 448 in a proximal direction to achieve the depicted position of the suture.

In some embodiments, bone anchor member 442 is inserted into a hole of the bone before plug portion 450 is inserted into bore 444. Once bone anchor member 442 is securely disposed within the hole, plug portion 450 is positioned slightly above bone anchor member 442, so that passage 448 is proximal to bore 444. At this time, first and second suture ends 32a and 32b may be individually tensioned to approximate the positioning of the tissue with respect to the bone (e.g., see FIG. 1).

Once the desired positioning is achieved, plug portion 450 may be advanced distally into bore 444 of bone anchor member 442. An insertion tool, such as insertion tool 294 of FIGS. 13A-13C, may be inserted into mating slot 458 to advance plug portion 450 distally. The provision of a sufficient distally directed force urges taper 454 over circumferential protrusion 449, thereby locking the plug portion within the bone anchor member, as shown in FIG. 22B.

At this time, first and second suture ends 32a and 32b are compressed within guide channel 456, while suture loop portions 34a and 34b are compressed within guide channel 457. Guide channels 456 and 457 may be sized to ensure that the suture is completely locked in place when plug portion 450 is inserted into bore 444 (see FIG. 22A). Alternatively, guide channels 456 and 457 may be sized to permit incremental adjustments of the suture, such that applying a sufficient tension to free ends 32a and 32b will overcome the frictional forces between the suture, plug portion 450 and bone anchor member 442.

Referring to FIGS. 23A-23C, an embodiment of the 450 of FIGS. 22A-22B is described. FIG. 23A is a cross-sectional view of an embodiment of the plug depicted in FIGS. 22A and 22B. FIG. 23B is a perspective side view of the plug depicted in FIG. 23A. FIG. 23C is a bottom view of the plug depicted in FIG. 23A.

In FIG. 23A, plug portion 450' includes distal passage 466, in lieu of passage 448 of FIGS. 22A-22B. Distal passage 466 is formed as a slot recessed in the distal end of main body 451. Distal passage 466 may communicate with opposing guide channels 456 and 457.

The operation of a bone anchor system using plug portion 450' is substantially similar to the steps described in FIGS. 22A-22B, with the exception that first and second suture ends 32a and 32b are disposed within distal passage 466. Specifically, during use, suture ends 32a, 32b can be looped around the distal end of plug portion 450', and need not be inserted by threading through central passage 448. Once the suture ends are looped around the distal end of plug portion 450' and confined within passage 466, then the suture may be held in place while inserting plug portion 450' into bone anchor member 442. Once the plug portion is locked into place via circumferential protrusion 449 (e.g., as described in FIG. 22B), then the suture is compressed between plug portion 450' and bone anchor member 442.

Referring to FIG. 24A, an apparatus includes alternative bone anchor member 442" and alternative plug portion 450". Bone anchor member 442" and alternative plug portion 450" are similar to bone anchor member 442 and plug portion 450 of FIGS. 22A-22B, except as noted below.

Plug portion 450" includes main body 451' having first suture clearance channel 456' formed in a first lateral surface of the body, and second suture clearance channel 457' formed in an opposing lateral surface of the body. Plug portion 450" also includes clearance recess 455 on a distal region of main body 451', along with suture channel 466'.

Main body 451' includes a plurality of cleated members 459a, which are formed adjacent to suture channel 466'. Also, bone anchor portion 442" includes a plurality of cleated members 459b formed in bore 444. Cleated members 459b are configured to oppose cleated members 459a when plug portion 450" is disposed in bore 444 of bone anchor member 442", as shown in FIG. 24B.

During use, suture length 30a is coupled to bone anchor member 442" by first forming loop 470 between regions 35a and 35b of the suture. A central portion of suture 30a then is looped around suture channel 466' of plug portion 450". At this time, proximal suture ends 33a and 33b are proximate clearance channel 456', while suture regions 35a and 35b are in the vicinity of clearance channel 457'. Plug portion 450" then is lowered into bore 444 of bone anchor member 442", as depicted in FIG. 24B.

When an appropriate force is applied, distal taper 454 of plug portion 450" passes over protrusion 449 of bone anchor member 442". At this time, protrusion 449 is confined within recess 453, as shown in FIG. 24B, to substantially inhibit movement of plug portion 450" with respect to bone anchor member 442". Proximal suture ends 33a and 33b are disposed within clearance channel 456', while suture regions 35a and 35b are disposed within clearance channel 457'.

In certain embodiments, suture loop 470 may be coupled directly to a tissue, as generally set forth hereinabove. Tensioning of suture ends 33a and 33b may directly effect positioning of the tissue. Further, as set forth above, cleated members 459a and 459b may form a one-way channel that facilitates tensioning of the suture ends, and locks the suture ends in place.

In some embodiments, a second suture length may be employed to anchor a tissue to a bone. FIGS. 25A-25B are illustrations of the bone anchor depicted in FIGS. 24A and 24B employing two sutures.

In FIG. 25A, second suture length 30b has loop 471, which is coupled directly to tissue T. Loop 471 is formed between suture portions 34a and 34b. Proximal to suture portions 34a and 34b, second suture 30b includes proximal ends 32a and 32b, which are configured to be manipulated during use.

Second suture 30b is coupled to first suture 30a by pulling proximal ends 32a and 32b through loop 470. At this time, four proximal suture ends will extend proximally from an access cannula (not shown). Specifically, proximal ends 32a and 32b of second suture 30b, along with proximal ends 33a and 33b of first suture 30a, all extend from the access cannula. Each of the four suture ends may be individually tensioned during use.

As each of the four suture ends 32a, 32b, 33a and 33b are selectively tensioned, loop 470 and suture regions 35a and 35b are urged towards clearance channel 457', as shown in FIG. 25B. When loop 470 is drawn towards clearance channel 457', second suture 30b also is drawn towards the clearance channel (i.e., because proximal ends 32a and 32b of the second suture have been previously pulled through loop 470).

At this time, the various suture regions that are drawn towards clearance channel 457' become inserted within the clearance channel to effectively lock the sutures in place. In effect, as tension is applied to the four suture ends 32a, 32b, 33a and 33b, tissue T is approximated to bone, and ultimately, the sutures are locked in place.

The use of the described method may save considerable time and effort during a surgical procedure. For example, bone anchor member 442", plug portion 450" and first suture 30a (including loop 470) may be provided in an already assembled state, as shown in FIG. 24B. These components need not be assembled during the surgical procedure.

At an appropriate time, second suture 30b is coupled to tissue T via loop 471. Using this method, it is not necessary to thread proximal suture ends 32a and 32b through plug portion 450" or bone anchor member 442" after suture 30b is coupled to tissue T. Rather, suture ends 32a and 32b are pulled through loop 470 of first suture 30a. In short, first suture 30a is coupled to tissue T, and then proximal ends 32a and 32b are guided through previously provided loop 470, thereby saving operating time and effort.

Figure 26A:
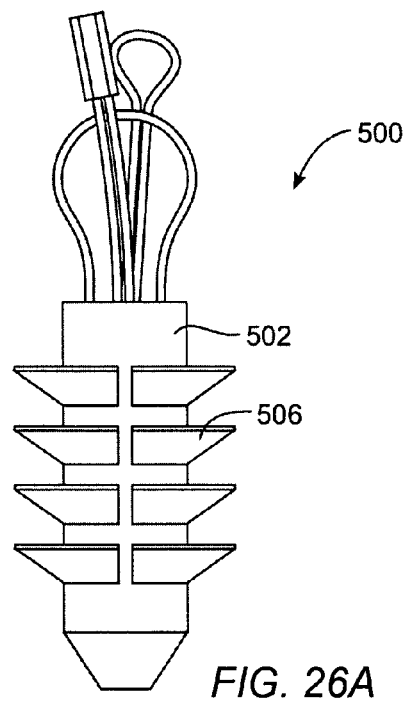
FIG. 26A depicts an embodiment of a bone anchor.
Figure 26B:
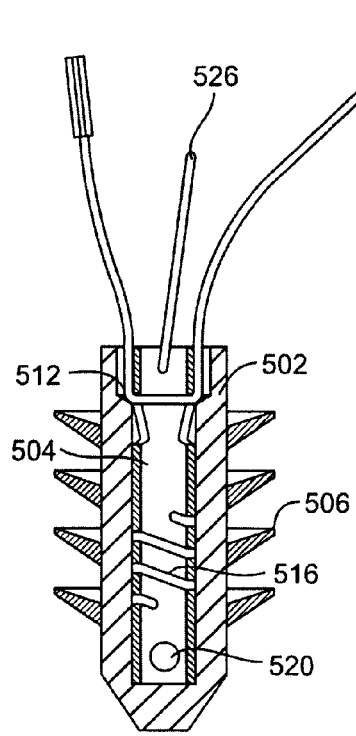
FIG. 26B is a cross-sectional view depicting a suture locking mechanism of the bone anchor depicted in FIG. 26A in a closed position.
Figure 26C:
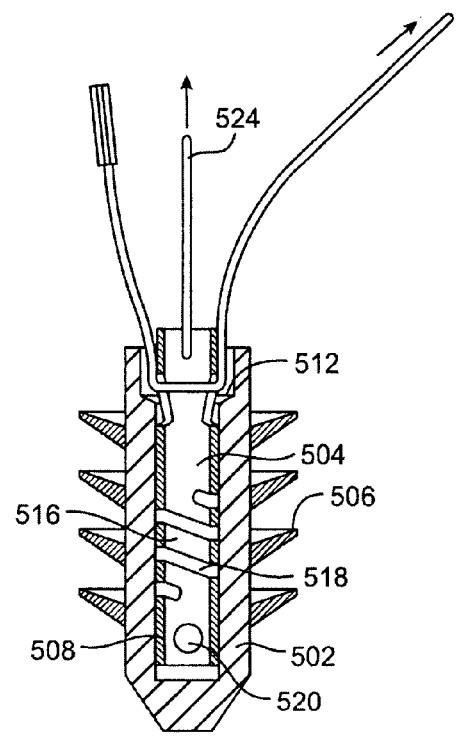
FIG. 26C is a cross-sectional view depicting the suture locking mechanism depicted in FIG. 26B in an open position.
Figure 26D:
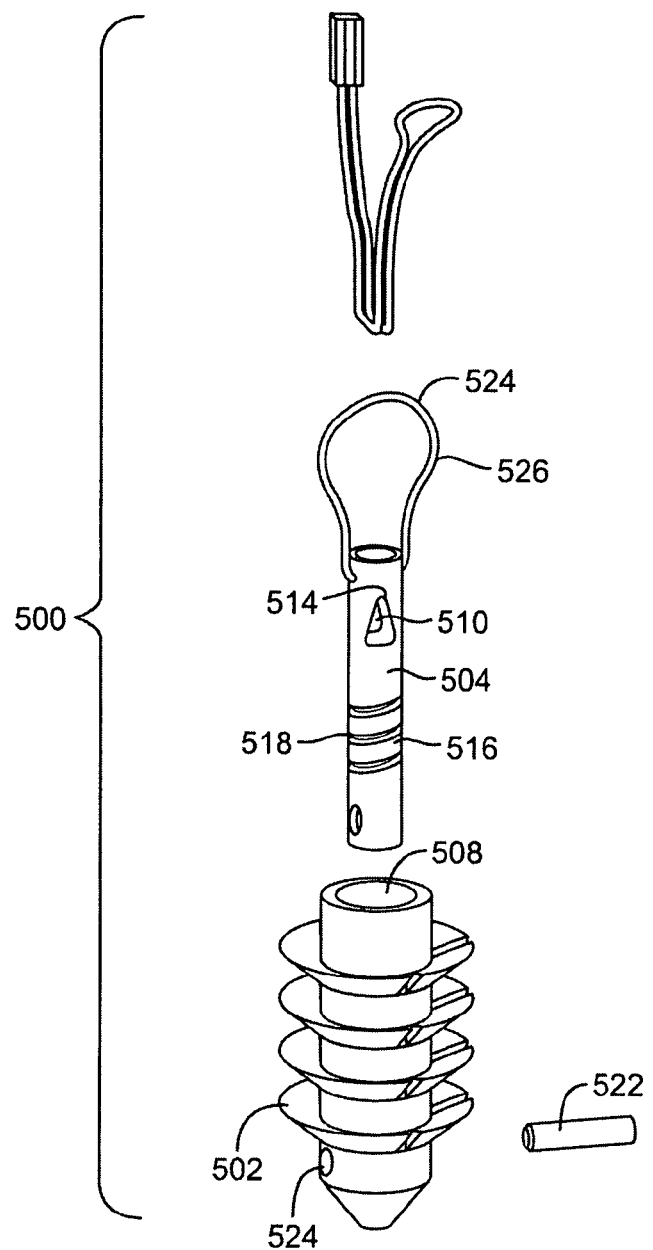
FIG. 26D is an exploded view of the bone anchor depicted in FIG. 26A.

Referring to FIGS. 26A-26D, an apparatus that includes a bone anchor is described. FIG. 26A depicts an embodiment of bone anchor 500. FIG. 26B is a cross-sectional view depicting a suture locking mechanism of the bone anchor depicted in FIG. 26B in a locked position. FIG. 26C is a cross-sectional view depicting the suture locking mechanism depicted in FIG. 26B in an unlocked position. FIG. 26D is an exploded view of the bone anchor of depicted in FIG. 26A.

Bone anchor 500 includes main body 502 and insert 504. Main body 502 has cleats 506, which are used to secure the bone anchor 500 to bone as discussed above. Main body 502 may have any other suitable feature to secure the anchor 500 to bone, such as an expandable portion, without departing from the scope of the invention.

Insert 504 is positioned in recess 508 in main body 502. The suture enters apparatus 500 through the proximal end of recess 508 and extends through a space between main body 502 and insert 504. The suture then passes hole 510 in insert 504. Hole 510 is, in some embodiments, triangular shaped to accommodate different size suture as shown in FIG. 26D.

Insert 504 is movable between the closed position of FIG. 26B and the open position of FIG. 26C. Recess 508 has beveled surface 512 on each side facing the hole 510 in the insert 504. The suture is captured between beveled surface 512 and upper end 514 of hole 510 when insert 504 is in the closed position of FIG. 26B. Insert 504 may be biased toward the closed position by spring portion 516 on insert 504. Spring portion 516 is formed by spiral cut 518 in insert 504. Insert 504 also has pinned connection 520 with main body 502 near the distal end. Pin 522 extends through hole 524 in insert 504 to provide pinned connection 520. Although spring portion 516 is formed integral with insert 504 a separate spring may also be provided similar to other embodiments described herein.

Insert 504 may be moved to the unlocked position of FIG. 26C by pulling on insert manipulator 524. Manipulator 524 may simply be flexible tether 526, which is pulled to move insert 504 to the unlocked position. When the procedure is completed, tether 526 may be cut and removed. Manipulator 524 provides the user with the ability to adjust suture tension as needed. Bone anchor 500 is used in the same or similar manner as the other apparatuses described herein.

Figure 27A:
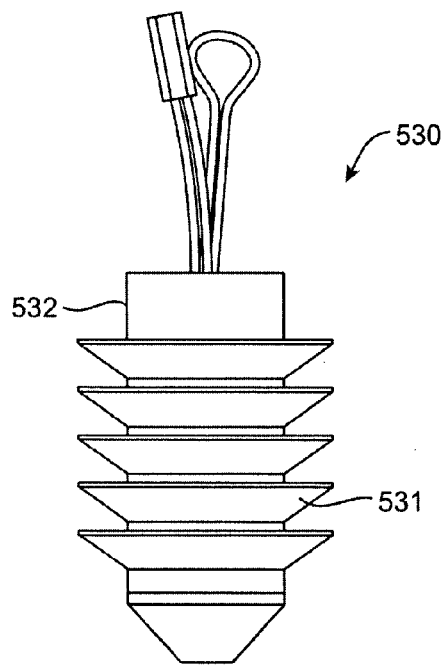
FIG. 27A is a perspective view of an embodiment of a bone anchor.
Figure 27C:
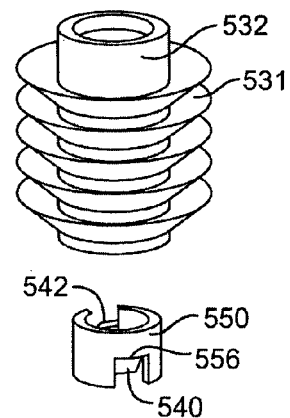
FIG. 27C is an exploded view of the bone anchor depicted in FIG. 27A.
Figure 27C:
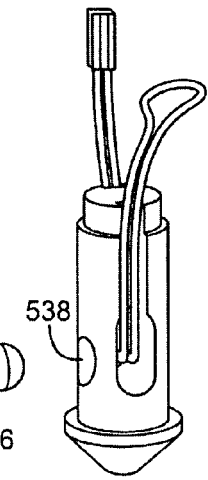
Figure 27B:
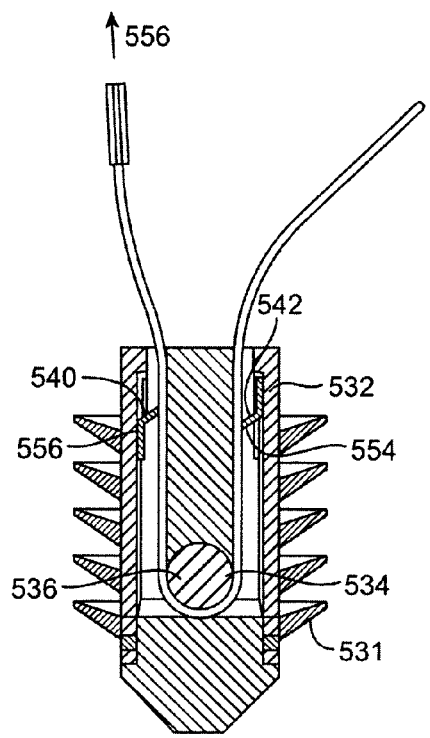
FIG. 27B is a cross-sectional view of the bone anchor depicted in FIG. 27A.

Referring to FIGS. 27A-27B, bone anchor 530 is described. FIG. 27A is a perspective view of an embodiment of a bone anchor. FIG. 27B is a cross-sectional view of the bone anchor depicted in FIG. 27A. FIG. 27C is an exploded view of the bone anchor depicted in FIG. 27A.

Bone anchor 530 has main body 532 with cleats 531 used to secure the bone anchor to bone although any other feature may be provided to secure bone anchor 530 to bone. The suture is locked with a suture lock 533. Suture lock 533 permits the suture to be advanced in the direction of arrow 556, but prevents movement in the other direction. The suture extends around bearing surface 534. Bearing surface 534 may be roller 536 although a non-rotating member may also be used. Roller 536 is mounted within hole 538. Suture lock 533 has first locking portion 540 and second locking portion 542, but may include any number of locking portions.

The first and second locking portions 540, 542 are integrally formed as ring clip 550. Ring clip 550 seats within annular recess 552 in main body 532. Suture locks 540, 542 include suture engaging portion 554 extending from ring clip 550. Locks 540, 542 may include an integrally formed living hinge 556. Living hinge 556 may permit the suture engaging portion 554 to deflect inwardly when suture is pulled in the direction of arrow 556. Suture lock 533 permits the suture to be pulled in the direction of arrow 556 and prevents the suture from being moved in the opposite direction. Bone anchor 530 is used in the same manner as bone anchors described herein.

Figure 28A:
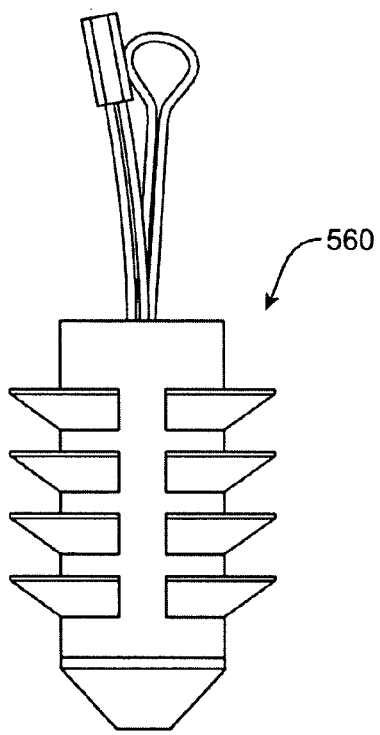
FIG. 28A is a perspective view of an embodiment of a bone anchor.
Figure 28B:
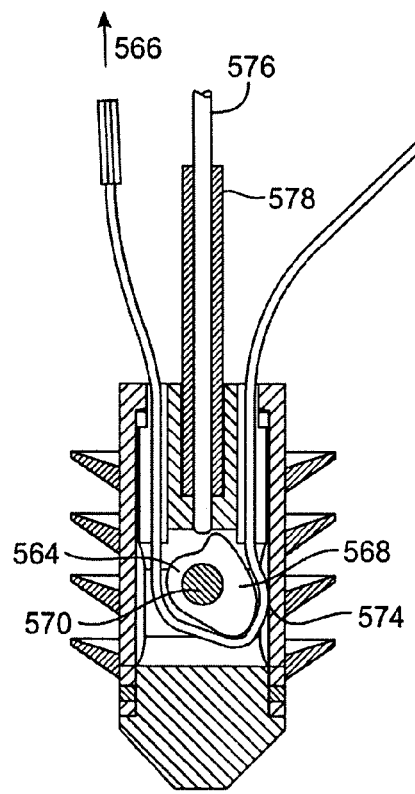
FIGS. 28B and 28C are cross-sectional views of the bone anchor depicted in FIG. 28A with release elements in the locked and unlocked positions, respectively.
Figure 28C:
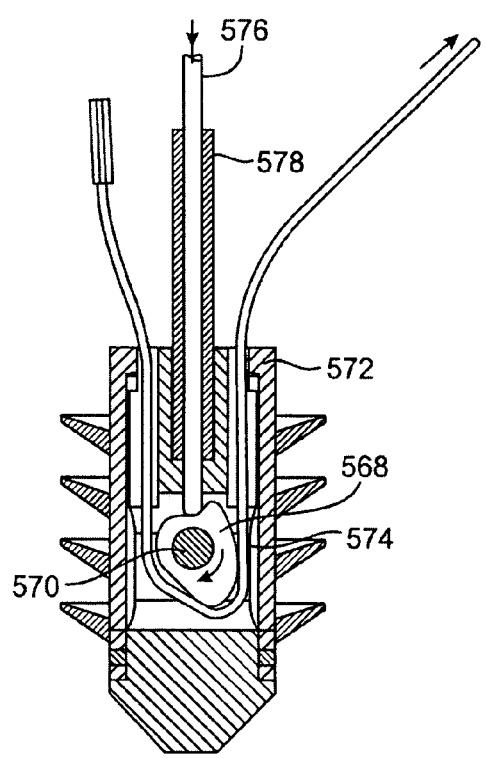
Figure 28D:
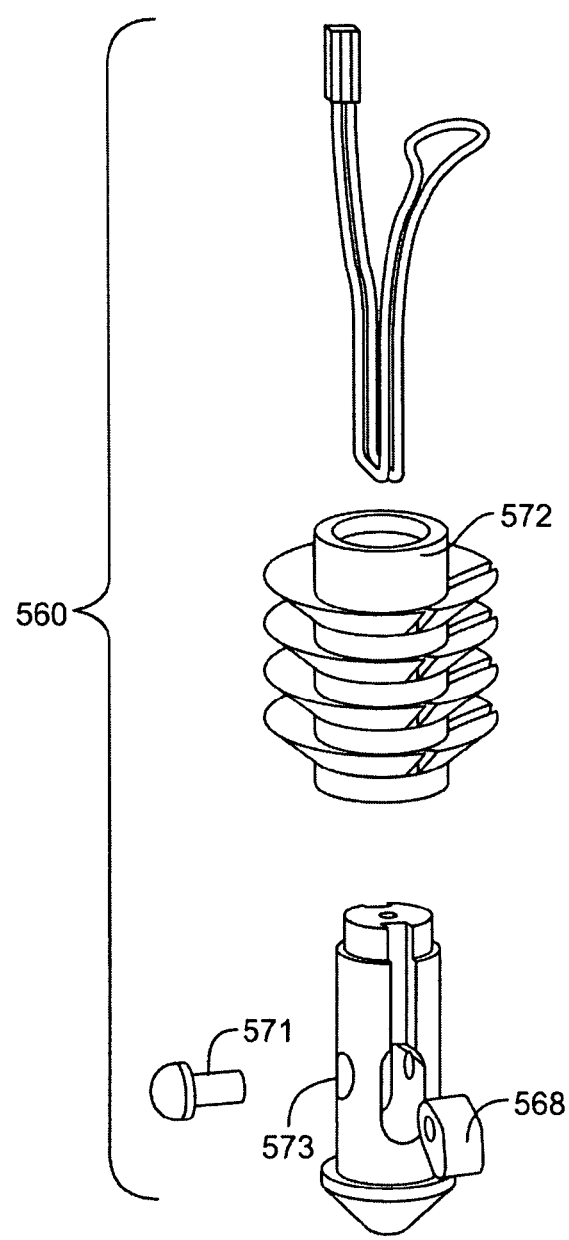
FIG. 28D is an exploded view of the bone anchor depicted in FIG. 28A.

Referring to FIGS. 28A-28D, bone anchor 560 is described. FIG. 28A is a perspective view of an embodiment of bone anchor 560. FIGS. 28B and 28C are cross-sectional views illustrating the use of a release element in conjunction with the bone anchor depicted in FIG. 28A. FIG. 28D is an exploded view of the bone anchor depicted in FIG. 28A. Bone anchor 560 is used in the same manner or similar manner as other bone anchors described herein.

Bone anchor 560 includes suture lock 564. Suture lock 564 allows a suture to be pulled in the direction of arrow 566, and prevents movement in the other direction. Suture lock 564 includes cam 568 having pinned connection 570 formed by pin 571 rotatable within hole 573 (see FIG. 28D). The suture is locked when the suture is trapped between cam 568 and inner surface 574 of main body 572.

Bone anchor 560 includes release element 576 for releasing suture lock 564. Release element 576 may be part of introducer 578. Introducer 578 may be used when advancing bone anchor 560 into bone. Release element 576 extends through a channel of introducer 578. Release element 576 and main body 572 may be configured (e.g., threaded) to allow the release element to be rotated and advanced to a desired position (e.g., as depicted in FIG. 28B). Release element 576 contacts upper portion of cam 568 and pivots the cam (e.g., as depicted in FIG. 28C). Pivoting the cam permits manipulation of the suture in one or more desired directions.

Further Improvements

Figure 29D:
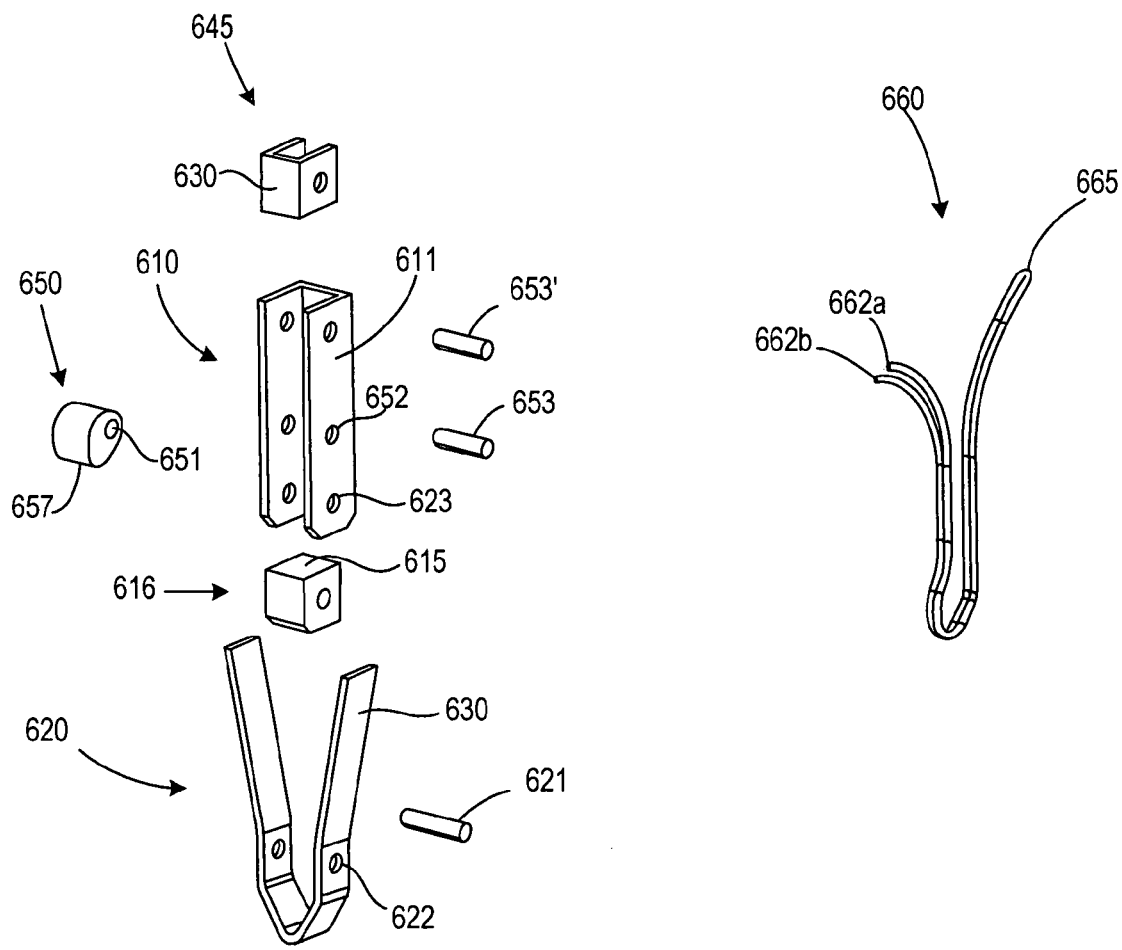
FIG. 29D is an exploded view of the bone anchor and suture depicted in FIG. 29A.

Referring to FIG. 29, an alternate non-limiting embodiment of a bone anchor 600 is shown. FIG. 29A depicts an embodiment of a bone anchor having a cam with a suture positioned between the cam and a surface at the distal end of the bone anchor. FIG. 29B is a cross-sectional view of the embodiment depicted in FIG. 29A. FIG. 29C is a frontal view of the bone anchor depicted in FIG. 29A. FIG. 29D is an exploded view of the bone anchor and suture depicted in FIG. 29A.

It will be apparent to practitioners of ordinary skill in the art that, while the non-limiting embodiment of bone anchor 600 depicted in FIG. 29A-29D has a substantially flattened profile, such a configuration is merely meant to be illustrative of the many alternate shapes that the presently described bone anchors may take. In different embodiments, bone anchor 600 may be configured to have cross sectional shapes and/or dimensions different from that depicted here, without departing from the spirit or scope of the embodiments set forth herein.

Bone anchor 600 may include main body 610 with sides 611. Sides 611 may form cavity 612. Sides 611 may entirely or at least partially enclose cavity 612. The cavity may extend distally along the entire length of the main body, or may optionally extend along only a portion of the length of the main body. Cavity 612 extends to the proximal end of the main body to form opening 613.

Main body 610 has inner surface 615 positioned at the distal end of end of cavity 612. Inner surface 615 may be formed from the main body at the time of its manufacture, or may be formed by coupling block 616 to the distal end of main body 610 (see FIG. 29D).

In some embodiments, opening 613 may be fully surrounded at the proximal end of main body 610. In certain embodiments, side surfaces 640 are coupled to main body 610 to enclose opening 613. Side surfaces 640 may be formed from the main body at the time of its manufacture, or may be formed by coupling retainer 645 to the proximal end of main body 610, as depicted in FIG. 29D.

Referring to FIG. 29A, bone anchor 600 may include cam 650 pivotally positioned in cavity 612. Cam 650 is pivotally coupled to main body 610 using, without limitation, any suitable art-recognized means of forming a rotatable connection. (e.g., a pin). In one non-limiting embodiment, cam 650 may be positioned in cavity 612 such that hole 651 is aligned with holes 652 on opposite sides 611, as depicted in FIG. 29D. Pin 653 may be inserted through the aligned holes to couple cam 650 to main body 610. This connection enables cam 650 to rotate (e.g., pivot) about the axis of pin 653, as shown in FIG. 29B.

In some embodiments, cam 650 may be configured to have an irregular cross sectional shape. FIGS. 29A-D depicts an embodiment where the cross sectional shape of cam 650 is substantially ovoid (e.g., see particularly FIG. 29B and FIG. 29D). It will apparent to a practitioner of ordinary skill in the art however, that the configuration of the cam presently described embodiment is exemplary only and serves to illustrate one of the many configurations of cams suitable for use with the subject bone anchors. It will be apparent to ordinary practitioners of the art that cams configured with any cross sectional shape may be substituted for that described herein without departing from the scope of the presently described embodiments.

Coupling cam 650 to main body 610 as described above allows the cam to freely pivot in cavity 612. In an embodiment, cam 650 may pivot in a first direction (e.g. downward) until outer cam surface 667 comes into contact with inner surface 615 (e.g., as depicted in FIG. 29B). After contact, further rotation of cam 650 in the first direction is blocked. Cam 650 may, however still pivot in the opposite direction (e.g. upward).

In some embodiments, cam 650 may be configured such that cam surface 667 is biased toward inner surface 615. Any suitable art-recognized means may be used to bias cam surface 667 toward inner surface 615. Examples of methods to bias a cam include, but are not limited to, coupling the cam to a spring bias assembly, or by forming at least a portion of cam and/or inner surface of the main body from a magnetized material.

Referring to FIG. 29A, one or more coupling members 630 may be disposed on the exterior surface of main body 610. Coupling members may be used to secure bone anchor 600 to an opening in a bone in which the bone anchor is positioned. Main body 610 may include any other suitable feature to secure the bone anchor 600 to bone, such as an expandable portion, without departing from the scope of the invention.

In an embodiment, coupling members 630 may extend radially from the main body. In an embodiment, coupling members 630 may be configured to reversibly engage a bone surface. Typically, coupling members may be formed, at least in part, of a substantially rigid or deformable material. In an embodiment, the coupling members are formed from the main body during the time of its manufacture. In some embodiments, coupling members may be manufactured separately and coupled to the exterior surface of the main body. In some embodiments, the main body may be coupled to the coupling members at the in a point of care setting. The main body may be configured to fit to a variety of coupling members, each having unique features suited to particular applications. A choice of coupling members may be provided to the physician at the point of care and coupled to the main body. Such a system allows the physician to choose the coupling member(s) best suited to a particular patient and application (e.g., size, depth and/or width of the bone hole), without having to interrupt and prolong the procedure underway in order to choose an alternate bone anchor and prepare it for implantation. The coupling of a main body to coupling members may be by any suitable means generally known in the art. By way of non-limiting examples, a main body may be coupled to coupling members using a snap-locks, screws, adhesives, or any other suitable means described above or generally known in the art. A non-limiting example is depicted in FIG. 29A. A physician may choose clip 620, which includes one or more radially extendable coupling members 630. After the choice is made, the bone anchor is readied for use by coupling clip 620 to main body 610. In an embodiment, a pinned connection may be formed by aligning hole 623 with hole 622 and inserting pin 621 through the aligned holes, as depicted in FIG. 29D. Coupling members 630 extend radially from main body 610.

In an embodiment, a bone anchor may be positioned in an opening in a bone by first retracting the coupling members. Retraction may be accomplished using a device (e.g., an inserter) that is capable of grasping the coupling members and compressing them toward the main body. When the bone anchor is suitably positioned in the bone opening, the inserter releases coupling members, allowing them to move radially outward and engage the surface of the bone opening. Alternatively, the bone anchor may be inserted into a bone opening without retracting the coupling members, and allowing the coupling members to grip the surface of the opening in which the bone anchor is placed.

Suture 660 may be positioned in bone anchor 600 to allow tensioning one or both ends of the suture to optimize positioning of the tissue relative to the bone. Suture 660 includes distal loop portion 665, which is coupled to the tissue, and suture end portions 662a, 662b, which are coupled to bone anchor 600. During use, suture end portions 662a and 662b may be tensioned so that the tissue is drawn toward the bone anchor.

Suture end portions 662a, 662b may be coupled to bone anchor 600 by entering through opening 613. Suture end portions 662a, 662b extend toward the distal end of main body 610. To engage cam 650, suture end portions 662a, 662b may be wrapped around at least a portion of outer surface of cam surface 650. Optionally, cam 650 may be textured on at least a portion of its outer surface. The texturing may allow the cam surface to frictionally grip the suture. The sutures may be wrapped around cam 650 such that the suture contacts at least about 30%, at least about 40%, at least about 50%, at least about 60%, or at least about 70% of the outer surface of cam 650. In an embodiment, suture end portions 662a, 662b may be wrapped around cam 650 in a hairpin configuration as shown in FIGS. 29A and 29B. By wrapping suture end portions 662a, 662b around the lower surface of the cam, the suture ends are positioned in space 666 between outer cam surface 667 and inner surface 615. Wrapping the suture around the cam in a hairpin configuration may maximize contact between the suture length and the outer surface of the cam. Thus, traction between the cam surface and the suture length is enhanced. After being coupled to cam 650, suture end portions 662 and 663 may extend toward the proximal end of main body 610 and exit through opening 613. In an embodiment, side surface 640 may hold suture end portions 662 and 663 in place at opening 613 (See FIG. 29B), allowingthe physician greater access to the suture and ease of manipulation of the suture during use.

In an embodiment, a suture puller (not shown) may facilitate threading of the suture ends through the bone anchor described above and shown in FIGS. 29A-D. The suture puller may be similar in shape and size to the suture coupled to the tissue. In some embodiments, the suture puller is substantially S-shaped.

The suture puller may be threaded through the bone anchor in the same manner as the suture, prior to the positioning of the anchor in a bone opening. The distal end of the suture puller couples to ends of the suture. During use, a loop of suture may pass through a tissue of interest. The end portions of the suture may couple to the distal end of the suture puller. Pulling a proximal end of the suture puller passes the suture puller through the main body of the bone anchor and threads a portion of the suture end through the opening in the main body, around the cam, between the outer cam surface and the inner surface of the main body, and out through the opening in the cavity.

When the suture is coupled to tissue and appropriately threaded through bone anchor 600, the sutured tissue may be drawn toward the bone by individually, or together, tensioning suture end portions 662 and 663 in the direction indicated by arrow 690 shown in FIG. 29B. Tensioning the suture causes cam surface 667 to move (e.g., pivot) away from inner surface 615, allowing movement of suture end portions 662 and 663 in the direction indicated by arrow 690. It will noted however that, due to the configuration of cam surface 667 relative to inner surface 615, after the tension applied to suture end portions 662 and 663 is released, cam surface 667 returns to its position adjacent to inner surface 615. Tension applied to suture end portions 662 and 663 in the direction indicated by arrow 695 locks the suture in place by compressing end portions 662 and 663 between cam surface 667 and inner surface 615. Thus, movement of a tissue coupled to a suture is allowed only in a desired direction, while slippage or movement of the tissue back to its original position is substantially prevented.

Figure 30A:
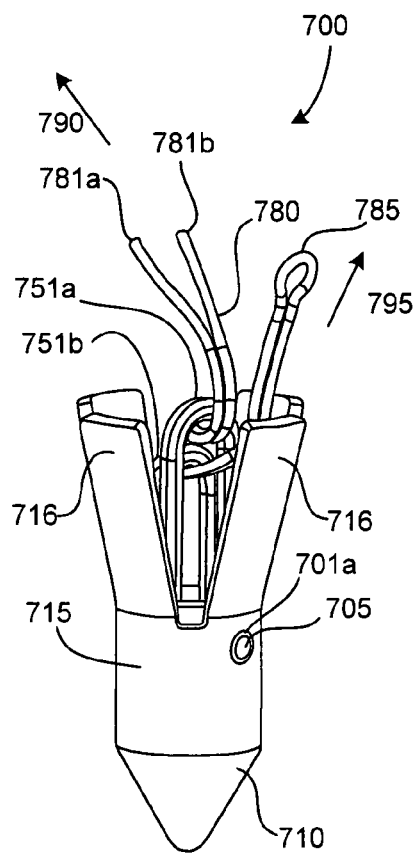
FIG. 30A depicts an embodiment of a bone anchor having a suture locking assembly.
Figure 30B:
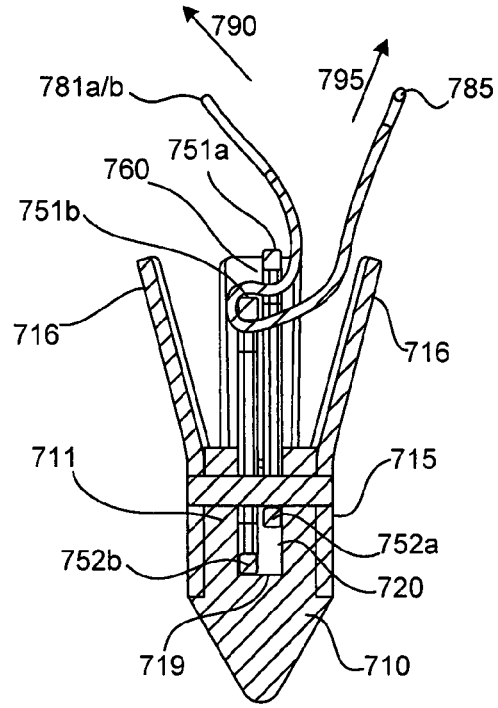
FIG. 30B is a cross-sectional view of the bone anchor depicted in FIG. 30A.
Figure 30C:
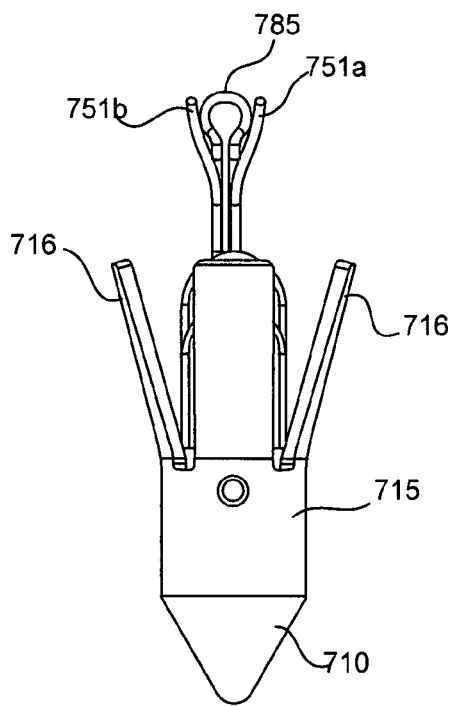
FIG. 30C is a perspective side view of the bone anchor depicted in FIG. 30A.
Figure 30D:
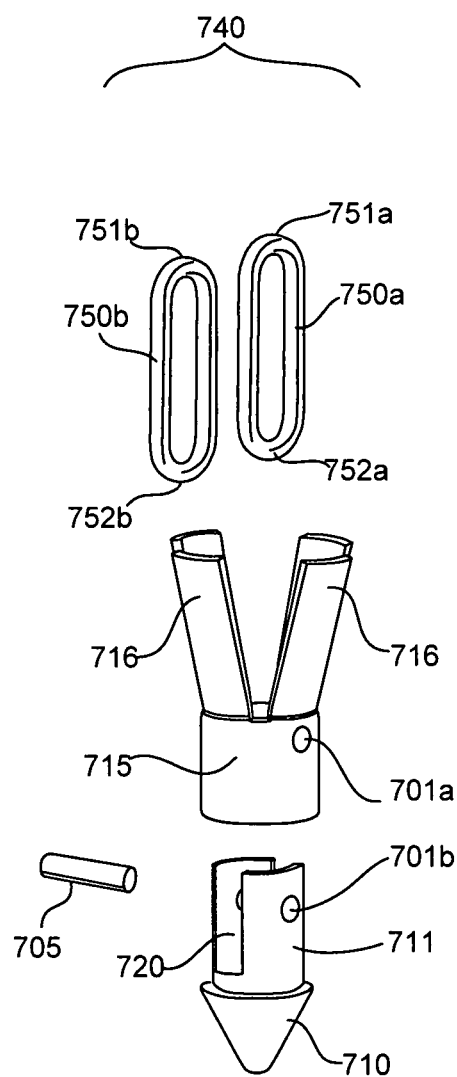
FIG. 30D is an exploded view of the bone anchor depicted in FIG. 30A.

FIGS. 30A-D describe bone anchor 700. FIG. 30A depicts an embodiment of the bone anchor having a suture locking assembly. FIG. 30B is a cross-sectional view of the bone anchor depicted in FIG. 30A. FIG. 30C is a side view of the bone anchor depicted in FIG. 30A. FIG. 30D is an exploded view of the bone anchor depicted in FIG. 30A.

Bone anchor 700 includes insert 710 and main body 715. Insert 710 includes one or more (e.g., a plurality) of flange members 711 (see FIG. 30D). Flange members 711 may extend proximally from insert 710. Cavity 720 is formed between flange members 711. Distal end of cavity 720 includes inner surface 719 (see FIG. 30B).

In some embodiments, main body 715 may be configured to couple to insert 710. As depicted in FIG. 30B, main body 715 is configured to accept and encircle flange members 711 and cavity 720. Main body 715 may couple to insert 710 by aligning hole 701a in main body 715 with holes 701b in flange members 711 (see FIG. 30D). Pin 705 may then be inserted though the aligned holes. Any alternate configurations of insert 710 and main body 715 that allow coupling thereof are possible and their means of coupling, without departing from the spirit and scope of the embodiments provided herein may be used.

Main body 715 may optionally include a plurality of radial coupling members 716. Radial coupling members 716 may secure bone anchor 700 to bone as described herein. Main body 700 may employ any art-recognized means for securing the anchor 700 to bone including, but not limited to, cleats.

Bone anchor 700 may also include locking assembly 740. Locking assembly 740 includes a plurality of locking elements 750. In FIG. 30D, locking elements 750 are depicted as locking rings 750a and 750b. Locking rings 750a and 750b include upper bar 751a and 751b and lower bar 752a and 752b, respectively. Locking rings 750a and 750b are sized to allow, when the locking rings are positioned parallel to each other, lower bars 752a and 752b to enter cavity 720 as depicted in FIG. 30B. Locking rings 750a and 750b may be positioned parallel to each other when lower bars 752a and 752b are disposed in cavity 720. In some embodiments, the locking rings are substantially parallel to each other. Lower bars 750a and 750b may be individually disposed at various positions or at the same position relative to inner surface 719 of cavity 720. In FIG. 30B, lower bar 752b is positioned adjacent to or in contact with inner surface 719. In some embodiments, lower bar 752a is positioned substantially adjacent to or in direct contact with inner surface 719. In contrast, lower bar 752a is positioned along the longitudinal axis of cavity 720, at a distance further from inner surface 719 than lower bar 752b. Similarly, upper bar 751b is closer to the opening of cavity 720 than upper bar 751a. Suture gap 760 lies between upper bars 751a and 751b and is sized to accommodate the thickness of a suture. The locking assembly described above may be referred to in some embodiments as a "two bar locking assembly."

In one embodiment, one or more of locking elements 750 may be axially movable in cavity 720. Moving locking element 750 in an axial direction may, in some embodiments, allow the locking elements to interact with each other to either lock or release a suture length positioned in gap 760 by compressing the suture length between upper bars 751a and 751b. In some embodiments, locking element 750 may be moved axially after desired positioning of a sutured tissue (e.g., after fine-tuning placement of the tissue), in order to reversibly lock the suture in place. Axial movement of locking elements 750 may be accomplished using any art-recognized means, including those described in detail above.

Suture 780 is positioned in bone anchor 700 to allow optimal positioning of a tissue relative to the bone by individually tensioning the ends of the suture, while substantially inhibiting movement of the suture and tissue coupled thereto in the opposite direction.

In some embodiments, suture 780 is configured to have a distal loop portion 785 and proximal suture end portions 781a and 781b. Distal loop portion 785 couples to tissue. Suture end portions 781a and 781b may be treaded through the locking assembly of bone anchor 700, and when tensioned in the direction indicated by arrow 790, draw the tissue toward the bone anchor. In some embodiments, suture end portions 781a and 781b may be threaded through a two bar locking assembly as depicted in FIGS. 30A and 30B. Loop portion 785 is positioned distally to bone anchor 700, at the tissue. Suture end portions 781a and 781b may couple to locking assembly 740 by passing the suture end portions through the opening of ring 750a and under upper bar 75 1b. Suture end portions 781a and 781b are wrapped upward around upper bar 751b, passed though suture gap 760 and wrapped upward around upper bar 751a. Suture end portions 781a and 781b are then available for facilitation of positioning of the sutured tissue (see FIG. 30B).

In certain embodiments, a suture puller may facilitate threading of the suture ends through the two bar locking assembly as described above. The suture puller may be similar in shape and size to the suture coupled to the tissue, and may be threaded through the bone anchor in the same manner as the suture, prior to the positioning of the anchor in a bone opening. The distal end of the suture puller couples to suture end portions 781a and 781b. During use, a loop of suture passes through a tissue. The end portions of the suture are coupled to the distal end of the suture puller. Pulling the proximal end of the suture puller in a desired direction (e.g., direction 790) passes the suture puller through the locking assembly and threads suture end portions 781a and 781b through ring 750a, under and around upper bar 751b, passed though suture gap 760 and finally wrapped around upper bar 751a.

When the suture is coupled to tissue and appropriately threaded through the locking assembly of the bone anchor, the sutured tissue may be drawn toward the bone by individually or together tensioning suture end portions 781a and 781b in the direction indicated by arrow 790 shown in FIG. 30B. Tensioning the suture ends thus allows the threaded suture to move through the locking assembly in direction 790, thus drawing tissue toward the bone. It will noted however that, due to the configuration of the two bar locking assembly relative to the threaded suture, movement or slippage of the tissue in an opposite direction is substantially inhibited. Tensioning the suture distally, in the direction indicated by arrow 795, causes the suture to apply an upward force to upper bar 751b, causing upper bar 751b and 751a to interact such that the suture length positioned in gap 760 is compressed between the upper bars, thus substantially locking the suture in place.

Turning now to FIG. 31, an alternate view of a bone anchor 800 is shown. FIG. 31A shows bone anchor 800 in which upper bars 851a/b of two bar locking assembly 840 are configured to be substantially straight. FIG. 31B shows a cross sectional view of bone anchor 800. FIG. 31C shows an exploded view of bone anchor 800, including two bar locking assembly 840 having locking elements 850*a/b* with straight upper bars 851*a/b*.

The bone anchor embodiments depicted in FIGS. 30 and 31 may be preferred for applications in which the bone anchor is to be inserted in soft bone. For example, radial coupling members 716 and 816 may be preferable when bone anchors 700 and 800 are to be inserted into a bone tunnel in soft bone. It will be understood by an ordinary practitioner of the art however, that other means of engaging the bone of a bone tunnel may be used in applications in which the bone anchor is to be inserted in harder bone, without departing from the spirit and scope of the presently described embodiments. It will further be understood that the material from which the above-described locking assemblies are made is not limited to any preferred material. However, in certain embodiments, locking rings may be made from an appropriate biocompatible memory material, such as nitinol.

FIG. 32 shows an alternate embodiment of that depicted in FIG. 31. FIG. 32A shows an embodiment of a bone anchor assembly 900 in which radial coupling members 816 are replaced by one or more cleated members 946. Cleated members 946 may facilitate the insertion of bone anchor assembly 900 into a bone tunnel in hard bone, and aid in the engagement thereof with bone on the surface of the tunnel. FIG. 32B shows a cross sectional view of bone anchor 900. FIG. 32C shows an exploded view of bone anchor 900, including two bar locking assembly 940 having locking elements 950*a/b* with straight upper bars 951*a/b*.

Figure 33:
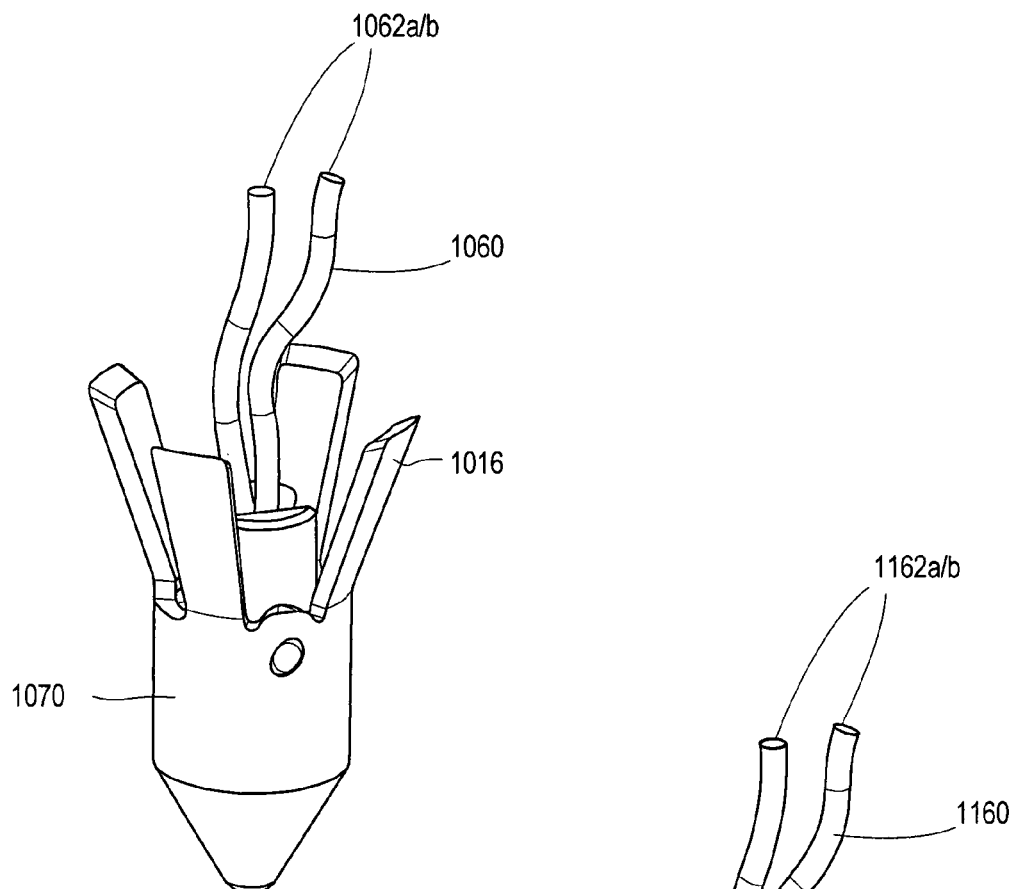
FIG. 33 depicts an alternate embodiment of a bone anchor having a fixed suture coupling.
Figure 34:
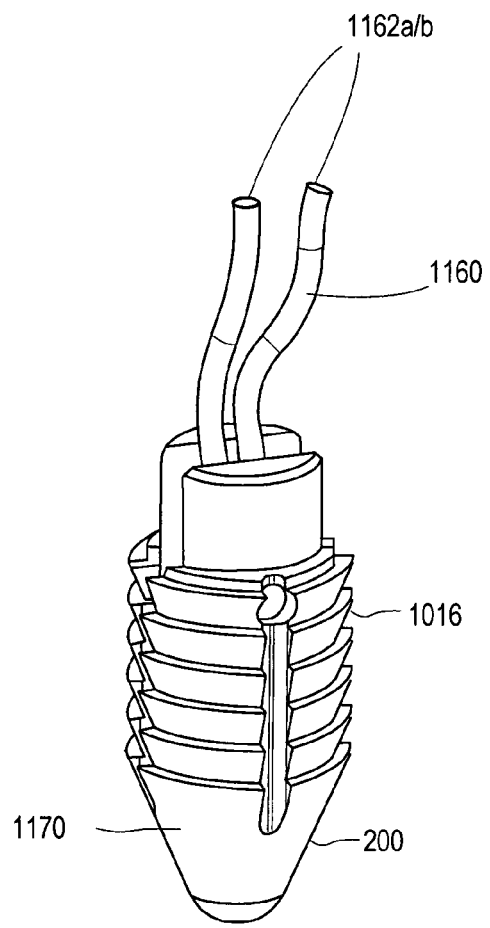
FIG. 34 is an alternate embodiment of that shown in FIG. 33.

FIGS. 33 and 34 show further alternate embodiments of bone anchor assemblies 1000 and 1100 in which suture 1060 is coupled to bone anchors 1000 and 1100, respectively, in a fixed position rather than being coupled thereto using a two bar locking assembly. In the non-limiting embodiments depicted in FIGS. 33 and 34, a middle portion of suture 1060 is coupled to body 1070 or 1170, and suture ends 1062*a/b* extend distally therefrom toward the surgeon.

FIG. 35A-35G show various alternate embodiments of bone anchors suitable for use with the presently described systems and methods.

Modular Design

Bone anchor 600 described certain embodiments where the main body is configured to be used with a variety of different coupling members, each having features suited to particular applications. It will be readily appreciated by ordinary practitioners of the art however, that this feature is not limited to the embodiments of bone anchor 600. Neither is this feature meant to be limited to the coupling of an internal portion to an external portion. In the contrary, components of the bone anchor assemblies described above are designed with the feature of modularity in mind. The ability to mix-and-match different features of an internal portion of a bone anchor assembly with a wide variety of features of external portions of the bone anchor is intended to be applied, without limitation, to all the embodiments described herein.

Incorporating the feature of modularity into the bone anchor assembly design parameters provides the following advantages: (a) maximized versatility in surgical applications without having to redesign bone anchor suited to such applications; (b) maintaining flexibility of the surgical procedure at the point-of-care; (c) full interchangeability of any component with any other component; (d) adjustability of each bone anchor component independent of the choice or position of other bone anchor components being used in a single surgical application; (e) allows the surgeon to tailor the assembly to the individual anatomy of the patient even in the face of a revision of the surgical procedure that might otherwise damage the bone or tissue; and (f) the use of all styles and sizes of interior and exterior components. The feature of modularity allows the physician to dedicate his or her full attention the procedure at hand, improving the prognosis and healing of the patient.

Securing a bone anchor member within a hole of a bone may be employed as previously described or using generally known bone securing techniques. For example, cleated members 42 of FIG. 2A, may be used means for securing the bone anchors. Other alternative means for securing may be used in conjunction with the apparatus and methods of the present invention. As an example, the bone anchor member may employ one or more radially expandable members that extend into the surrounding bone.

Further, while some of the embodiments of the present invention describe use of a bone anchor member only, and other embodiments describe use of a bone anchor member and a plug portion, many of these features may be interchanged. It will be apparent to one skilled in the art that many embodiments depicting a bone anchor member only may be performed using a bone anchor member and plug portion, and vice versa.

Also, for those embodiments described above having a bone anchor member and a plug portion, it will be apparent to those skilled in the art that the suture ends may be tensioned either before or after the plug portion is inserted into the bore of the bone anchor member.

It will also be apparent to one skilled in the art that the plug portion may be securely disposed within the bore of the bone anchor member using various means not specifically disclosed herein. For example, after the plug portion is inserted into the bore of the bone anchor member, an adhesive, for example, cyanoacrylate, epoxy, bone cement and so forth, may be delivered to affix the plug portion to the bone anchor member. Alternatively, an exterior surface of the plug portion may be coated with a biocompatible adhesive that affixes to the bone anchor member after the plug portion is inserted into the bore of the bone anchor member. In some embodiments, heat may be applied to fuse the plug portion to the bone anchor member. It will be apparent to one skilled in the art that still further means for securing the plug portion to the bone anchor member may be employed.

It should be understood that multiple bone anchor members, or multiple bone anchor members coupled to respective plug portions may be used. One or more sutures may be coupled between a desired tissue region and the bone anchor member or plug portion. If multiple sutures and bone anchor members are employed, enhanced sequential tensioning of the tissue may be achieved.

Finally, while the above-described embodiments reference use of apparatus and methods for facilitating attachment of tissue to bone, it will be apparent to one skilled in the art that such apparatus and methods may also be used to secure tissue-to-tissue and bone-to-bone.

Bone Anchor Inserter Systems And The Uses Thereof

The presently described embodiments may optionally be provided in combination with an installer system adapted for use in deploying the presently described bone anchors to the operative site.

Figure 36:
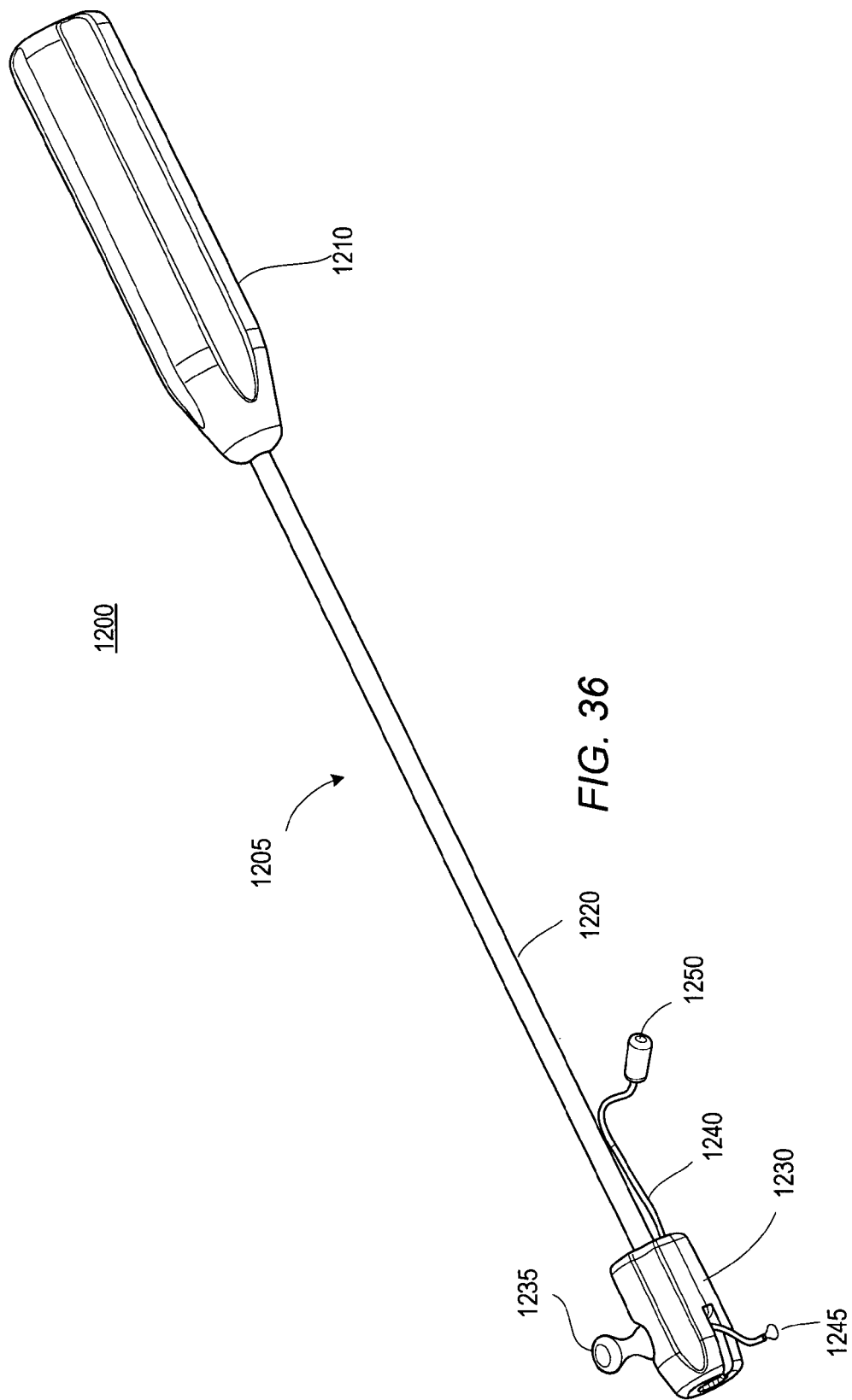
FIG. 36 depicts an embodiment of a bone anchor installer for use in a bone anchor system.

A system for deploying a bone anchor to an operative site may include a bone anchor installer device. FIG. 36 shows a bone anchor installer device 1200 according to a first non-limiting embodiment. Bone anchor installer 1200 may include anchor loading tool 1205 having a proximal handle portion 1210 and an elongated anchor loading portion 1220 extending distally therefrom. In an embodiment, a bone anchor installer may further include an anchor holder 1230 coupled to the distal end of anchor loading portion 1220. Anchor holder 1230 may be configured to hold a bone anchor in place at the distal end of the installer prior to the deployment thereof in a bole prepared in bone. In an embodiment, anchor holder 1230 may include pin 1235 detachably coupled thereto. During use, a bone anchor loaded to installer 1200 may be deployed by detaching pin 1235 from anchor holder 1230. Detaching pin 1235 in this way may allow the uncoupling of anchor housing 1230 from the distal end of installer loading portion 1220, and exposing the bone anchor loaded on the distal end thereof (described below). In an embodiment, a system for deploying a bone anchor may optionally include suture puller 1240 pre-loaded through the bone anchor in the anchor holder. Suture puller 1240 may be pre-loaded to the installer device in such a way as to facilitate the threading of one or more suture ends through a two bar locking assembly, as described above. Suture puller 1240 may include grasping portion 1250, which extends proximally from anchor holder and is readily accessible to the surgeon during use. Suture puller 1240 may further include loop portion 1245 at its distal end. Loop portion 1245 may be configured to hold suture ends while they are being pulled through anchor holder 1230 and loaded to the bone anchor residing therein as described in greater detail below.

Turing to FIG. 37, anchor holder 1230 is shown in greater detail. In an embodiment, an anchor holder coupled to the distal end of an installer may include a first holder portion 1231 and a second holder portion 1232 configured to be reversibly coupled to each other so as to define anchor holder 1230. First and second holder portions 1231 and 1232 may define channel 1234 along the longitudinal axis of the anchor holder. Channel 1234 may be sized to accept bone anchor 700 and the distal end of loading portion 1220 of anchor loading tool 1205.

Figure 37A:
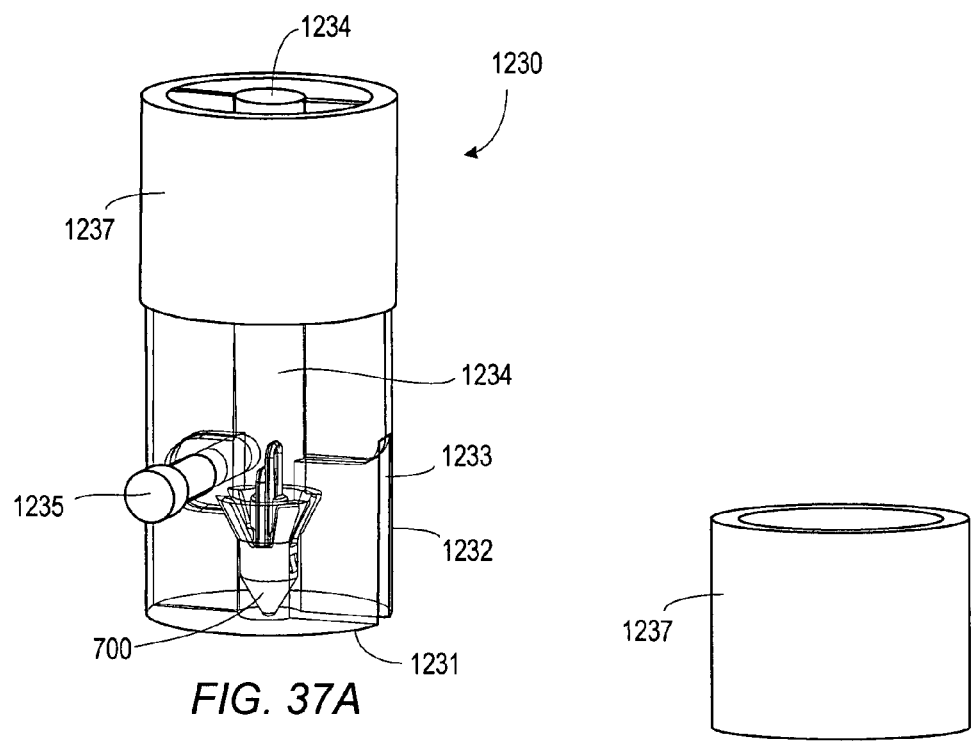
FIG. 37A is a schematic representation of an anchor holder according to an embodiment of a bone anchor installer.
Figure 37B:
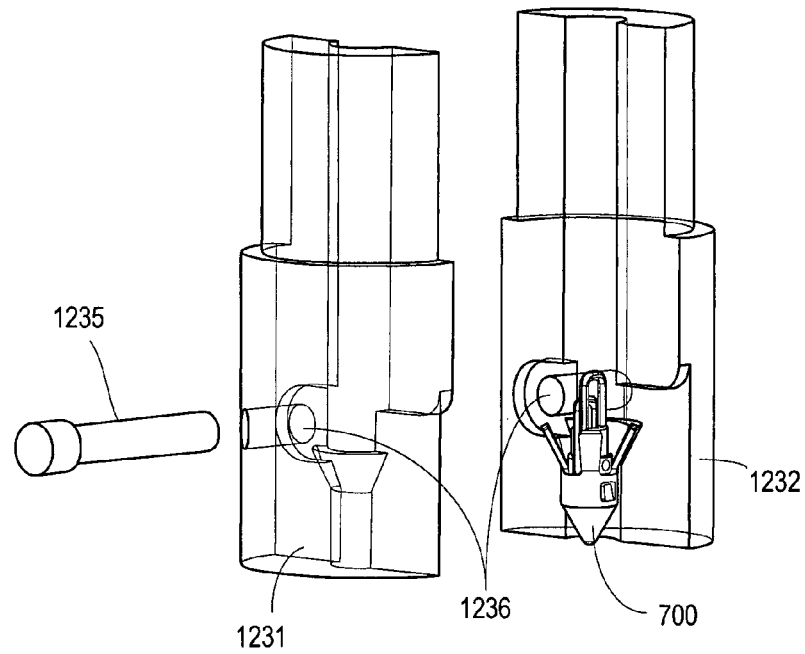
FIG. 37B is an exploded view of the anchor holder depicted in FIG. 37A.

In an embodiment, first and second holder portions 1231 and 1232 may be coupled to each other by way of pin 1235 as depicted in FIG. 37A. In an alternate embodiment, first and second holder portions 1231 and 1232 may be held together through slideable ring 1236, when engaged encompasses the holder portions. Pin 1235 and ring 1236 may be used as a means of keeping anchor holder 1230 assembled. Pin 1235 and ring 1236 may be used either alone or in combination. First and second holder portions 1231 and 1232 may be configured to define canal 1234 when they are coupled, as shown in FIG. 37A. Canal 1234 extends substantially along the longitudinal axis of anchor holder 1230. The diameter of canal 1234 is sized to accept bone anchor 700, or any of the previously disclosed alternate bone anchor embodiments. Though not shown here, the diameter of canal 1243 is also sized to accept the distal end of anchor loading portion 1220.

As discussed above, first and second holder portions 1231 and 1232 may be coupled by way of pin 1235. Pin 1235 may reside in a channel defined by bore 1236 (FIG. 37B), which extends through at least a portion of the body of anchor holder 1230, at an axis substantially perpendicular to that of canal 1234. To uncouple first and second holder portions 1231 and 1232, pin 1235 may be removed from bore 1236. Alternatively, slidable ring 1236 may be moved in such a way (e.g., FIG. 37B) that first and second holder portions 1231 and 1232 are no longer coupled together.

Figure 38A:
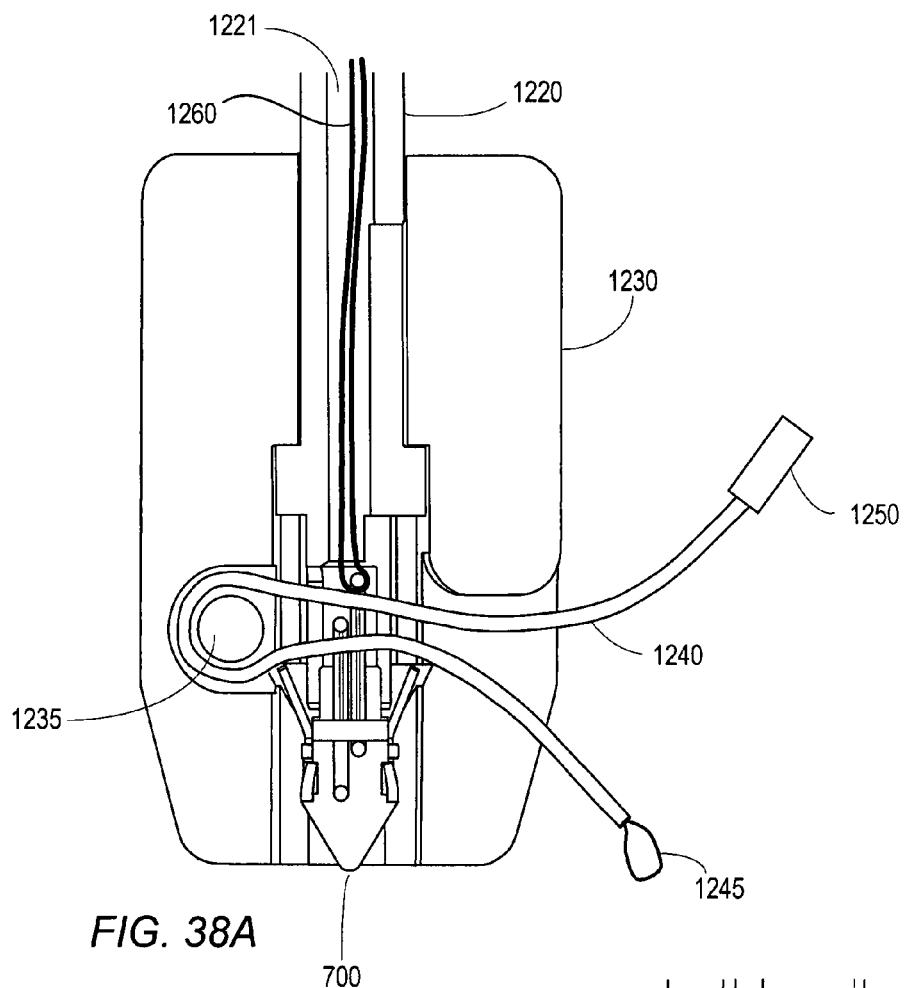
FIG. 38A is a side sectional view of an anchor holder according to an embodiment.

FIG. 38A shows an enlarged cross sectional view of the distal end of bone anchor installer device 1200 according to an embodiment, where a portion of anchor holder 1230 is removed. Bone anchor 700 may be loaded to the distal end of anchor loading portion 1220 and help in place by anchor holder 1230. Optionally, anchor 700 may be tethered to the proximal end of anchor loading tool 1205 by way of tether 1260 located in lumen 1221, which may extend along the longitudinal axis of anchor loading portion 1220 and optionally as far as handle portion 1210. In an embodiment, one end of tether 1260 may be coupled to a portion of the bone anchor (e.g., to one of the two rings defining the two bar locking mechanism) and the other end may extend to the proximal end of the anchor loading tool. In an embodiment, tether 1260 may be accessible to the surgeon during use. In an embodiment, the tension of tether 1260 may be varied so as to keep bone anchor 700 loaded on the anchor loading tool after anchor holder 1230 has been removed.

In an embodiment, a bone anchor installer system may also include suture puller 1240 pre-loaded through the bone anchor in the anchor holder. Suture puller 1240 may be pre-loaded to the installer device in such a way as to facilitate the threading of one or more suture ends through a two bar locking mechanism of a bone anchor, at the time of its deployment. In an embodiment, suture puller 1240 may include grasping portion 1250 at one end. Grasping potion 1250 may be exterior to anchor holder 1230 and be readily accessible to the surgeon during use. Suture puller 1240 may further include loop portion 1245 at the other end. Loop portion may also be exterior to the anchor holder, such that it is accessible for coupling to suture ends. In an embodiment, the central portion of suture passer 1240 may be substantially disposed in anchor holder 1230, and threaded through at least the two bar locking mechanism of a bone anchor in such a way to enable the suture ends to be properly loaded thereto. As shown in FIG. 38A, a portion of suture puller 1240 closer to loop portion 1245 may pass under the lower bar of the locking assembly, and a portion of suture puller 1240 closer to grasping portion 1250 may pass between the two bars of the locking assembly. Optionally, the intervening portion of the suture puller may be looped around pin 1235.

Figure 38B:
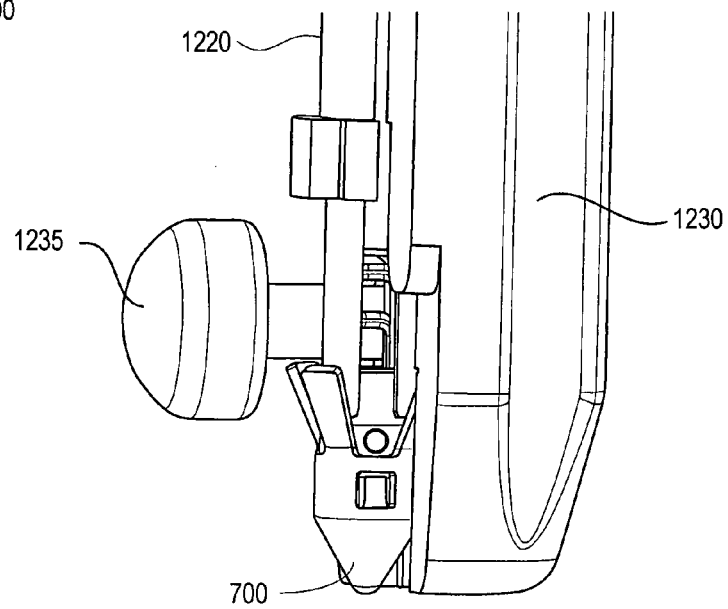
FIG. 38B is an oblique view of the anchor holder depicted in FIG. 38A.

FIG. 38B is a side sectional view of the device shown in FIG. 38A, in which the arrangement of bone anchor 700 and anchor loading portion 1220 relative to each other and to anchor holder 1230 is shown. In this view, suture puller 1240 is not shown.

Figure 39B:
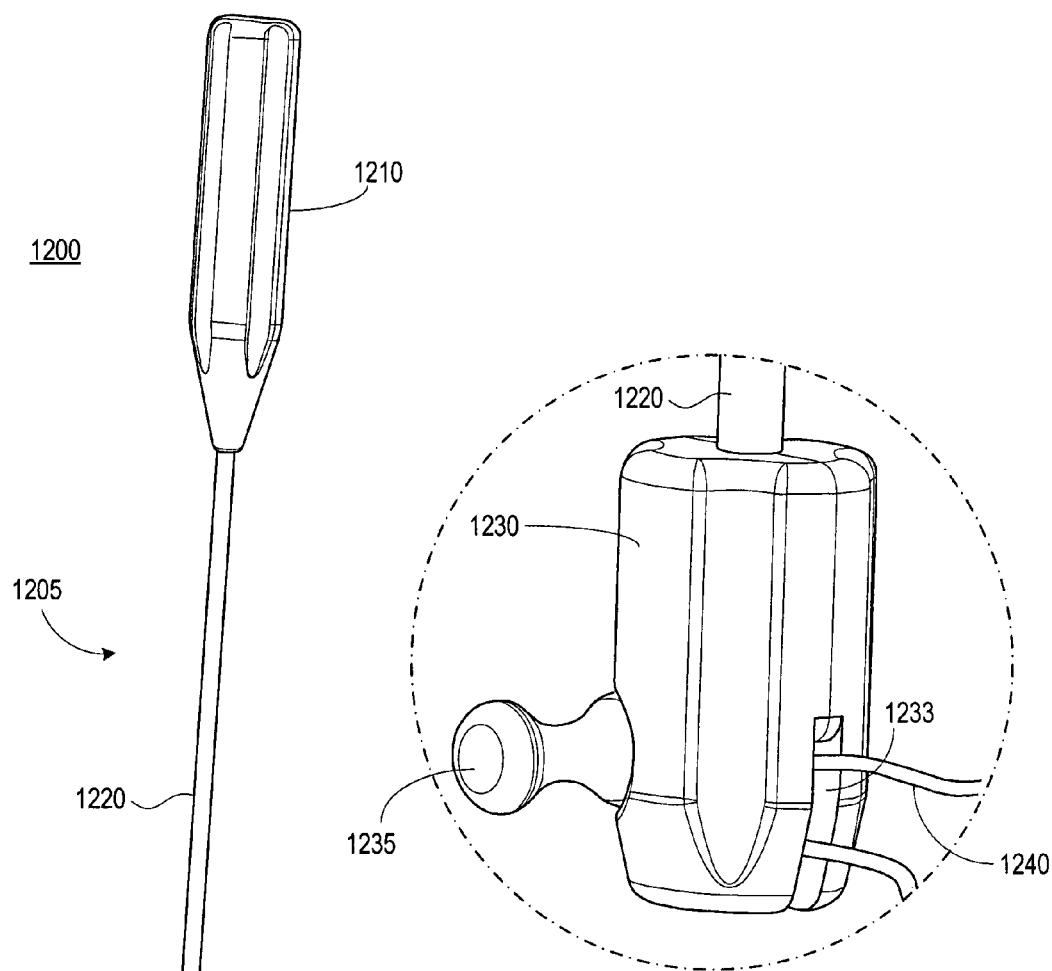
FIG. 39B is an enlarged view showing the anchor holder at the distal end of the bone anchor installer depicted in FIG. 39A.
Figure 39A:
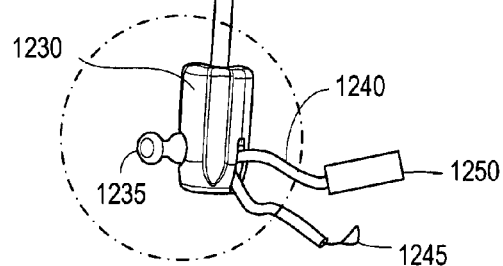
FIG. 39A is a depiction of a bone anchor installer according to an embodiment.
Figure 40A:
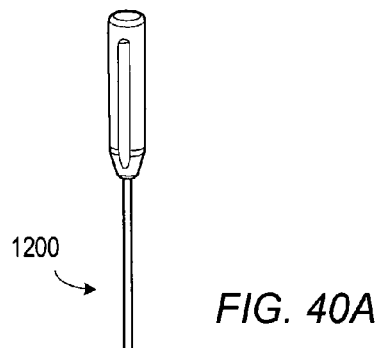
FIG. 40A-40F depict a sequence of steps to use the bone anchor installer depicted in FIG. 39A.
Figure 40B:
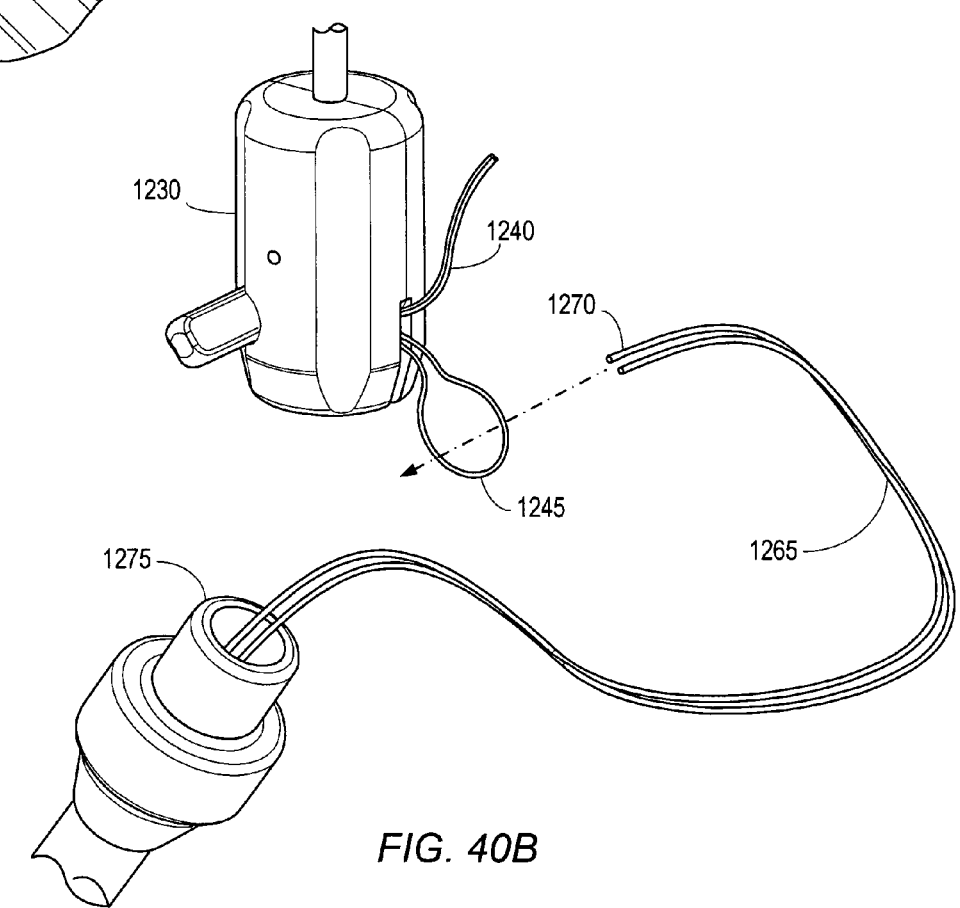
Figure 40C:
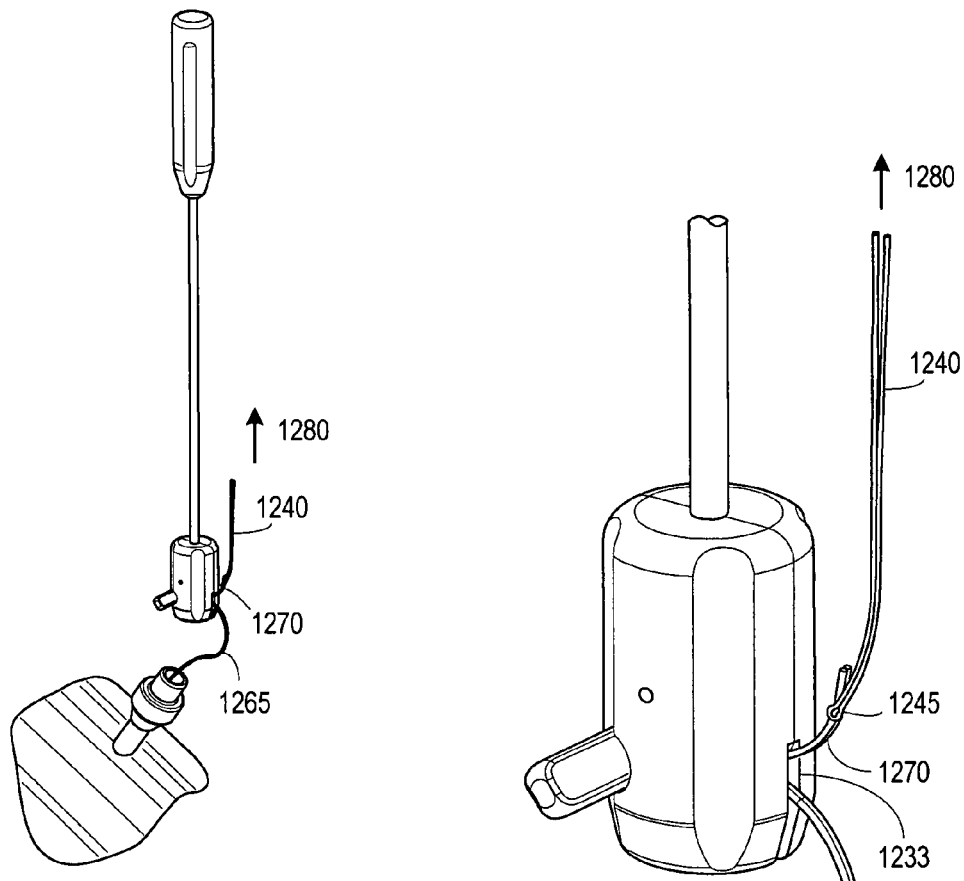
Figure 40D:
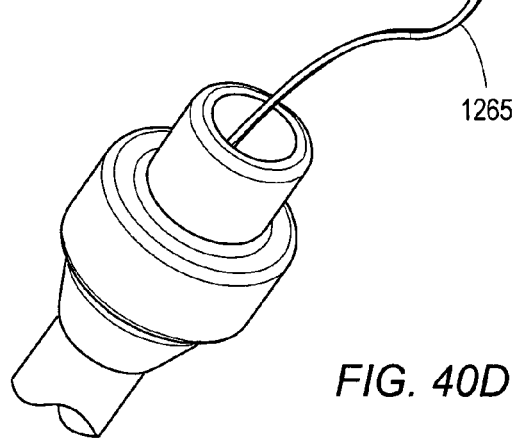
Figures 40E, 40F:
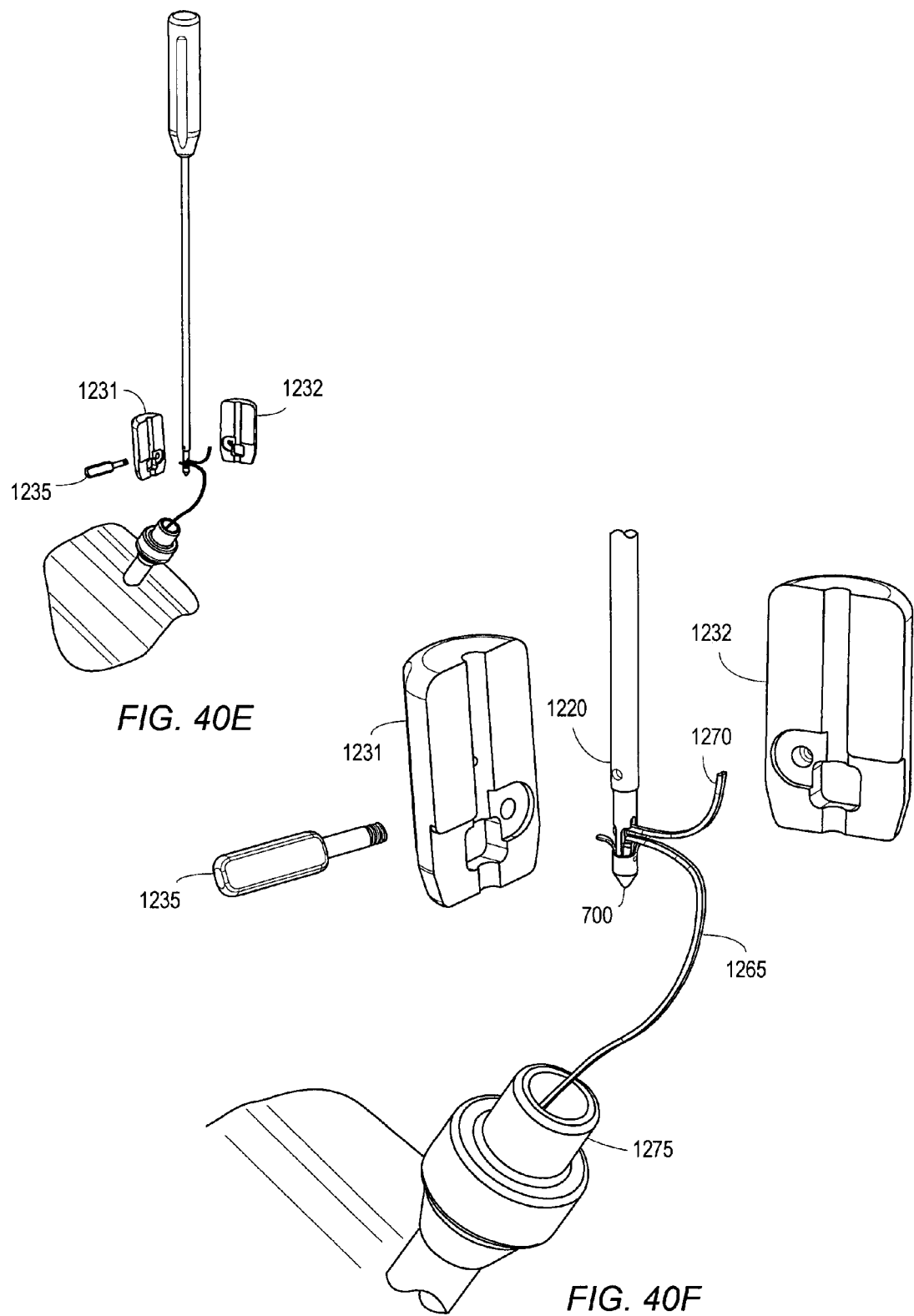

FIG. 39 shows bone anchor installer device 1200 prior to deployment. FIG. 39B shows an enlarged view of the distal end of the installer, including suture puller 1240 threaded through bone anchor 700 (not seen) as described above. In an embodiment, anchor holder 1230 may include slit 1233, through which loop portion 1245 and grasping portion 1250 may pass.

FIG. 40 depicts a procedure for deploying a bone anchor using a bone anchor installer device according to an embodiment. Turning to FIG. 40A, cannula 1260 may be placed in tissue 1275 so as to make accessible the site into which a bone anchor will be installed. Cannula 1260 will be sized such that the distal end of anchor loading portion 1220 with the bone anchor loaded to the end thereof may be readily passed through the cannula to the site of bone anchor implantation. In an embodiment, suture 1265, which will be used to couple tissue to the bone anchor, may be coupled to the appropriate tissue. Suture ends 1270 may then be passed through the cannula where they will be accessible to the surgeon. In an embodiment, a suture passer device as described below may be used to suture the tissue and to retrieve and pass suture ends 1270 through cannula 1275 as depicted in FIG. 40A. FIG. 40B shows an enlarged view of the distal end of bone anchor installer device 1200 and cannula 1260 with suture ends 1270. To thread suture 1265 through a bone anchor, suture ends 1270 may be passed through loop portion 1245 of the suture puller. Next, the surgeon pulls suture puller 1240 out of anchor holder 1230 in the direction of arrow 1280 in FIGS. 40C and D, thereby threading the suture ends that are coupled to loop portion 1240 through the locking assembly of the bone anchor. In a final step shown in FIG. 40, the surgeon removes pin 1235 from anchor holder 1230, thereby releasing first and second holder portions 1231 and 1232 from the distal end of anchor loader portion 1220 and exposing the threaded bone anchor ready for installation in a bone hole. As described above, bone anchor 700 remains tethered to the distal end of anchor loading portion 1120 by tether 1260, as described above. The threaded anchor shown in FIG. 40F then be passed through the cannula 1275 and installed at the operative site.

FIG. 41 depicts a bone anchor installer 1200' according to an alternate embodiment. Bone anchor installer 1200' may be substantially similar the bone anchor installer 1200 already described, with the following differences. In an embodiment, proximal handle portion 1210' of anchor loading tool 1205' may be configured such that the proximal end of tether 1260' is made accessible to the surgeon. In an embodiment, this may be accomplished by forming, for example, a bore (not seen here) through the length of handle portion 1210', along its longitudinal axis. The bore may start at the proximal tip of handle portion 1210' and extend to handle portion tip 1212,' which couples handle portion 1210' to the proximal end of anchor loading portion 1220'. At tip 1212' the bore may form a continuous passage with lumen 1221' extending along anchor loading portion 1220, through which the free end of tether 1260' is passed, as shown in FIG. 41A. End cap 1211' may be reversibly couplable to the proximal end of handle portion 1210'. When coupled to handle portion 1210' as shown, end cap 1211' may secure tether 1260' such that the tether coupling bone anchor 700' to the distal end of anchor loader portion 1220' is kept taught.

In an embodiment, grasping portion 1250' of suture passer 1240' may be substantially ring shaped. In an embodiment, ring portion 1250' may include clip 1251,' which is configured to couple ring portion 1250' to the distal end of anchor loading portion 1220' such that ring portion 1250' is able to slide along the longitudinal axis of anchor loading portion 1220' as depicted in FIG. 41B. FIG. 41B also shows a view of a portion of tether 1260' residing within the lumen of anchor loader portion 1220'.

FIGS. 42A-D show how a bone anchor may be tethered to anchor loading tool 1205' during use in accordance with one embodiment. Turning to FIG. 42A, anchor loading tool 1205' may include handle portion 1210' that is couplable to anchor loading portion 1220'. Handle portion 1210' may include fastening means 1214' disposed at its proximal end, and tip 1212' and it distal end. Fastening means 1214' may be configured such that cap 1211', shown in FIG. 42B may be reversibly coupled thereto. In an embodiment, fastening means 1214' may include screw threads.

Anchor loading portion 1220' may be substantially tubular in shape, with lumen 1221' extending along its length. Anchor loading portion 1220' may include loading tip 1225' disposed at the distal end thereof. FIG. 42C is an enlarged view of distal end of the anchor loading tool shown in FIG. 42B. Loading tip 1225' may be formed with flange members 1226' which are configured to engage bone anchor 700 during use (see, e.g., FIG. 38B).

Handle portion 1210' may also include bore 1215' extending from fastening means 1214' to tip 1212'. When the handle portion and anchor loading portions are coupled to form anchor loading tool 1205' shown in FIG. 42B, bore 1215' is continuous with lumen 1221' of anchor loading portion 1220, thereby defining a passage in which tether 1260' is disposed. Tether 1260' may be made of any thread or line suitable for use in surgical applications. Tether 1260' may be used to engage a portion of anchor 700' and couple it to loading tip 1225'. In an embodiment, a portion of tether 1260' may be folded around a portion of the bone anchor locking assembly (see, e.g., FIG. 42C, element 1260a). The ends of tether 1260' pass through lumen 1221' and bore 1215' of the anchor loading portion and handle portion, respectively, and emerge from fastening means 1214' as shown in FIGS. 42B and 42D. To load the anchor to loading tip 1225', the ends of tether 1260' are tensioned. The tether is kept taught by coupling cap 1211' to fastening means 1214'.

Suture Passer Devices And The Uses Thereof

Figure 43:
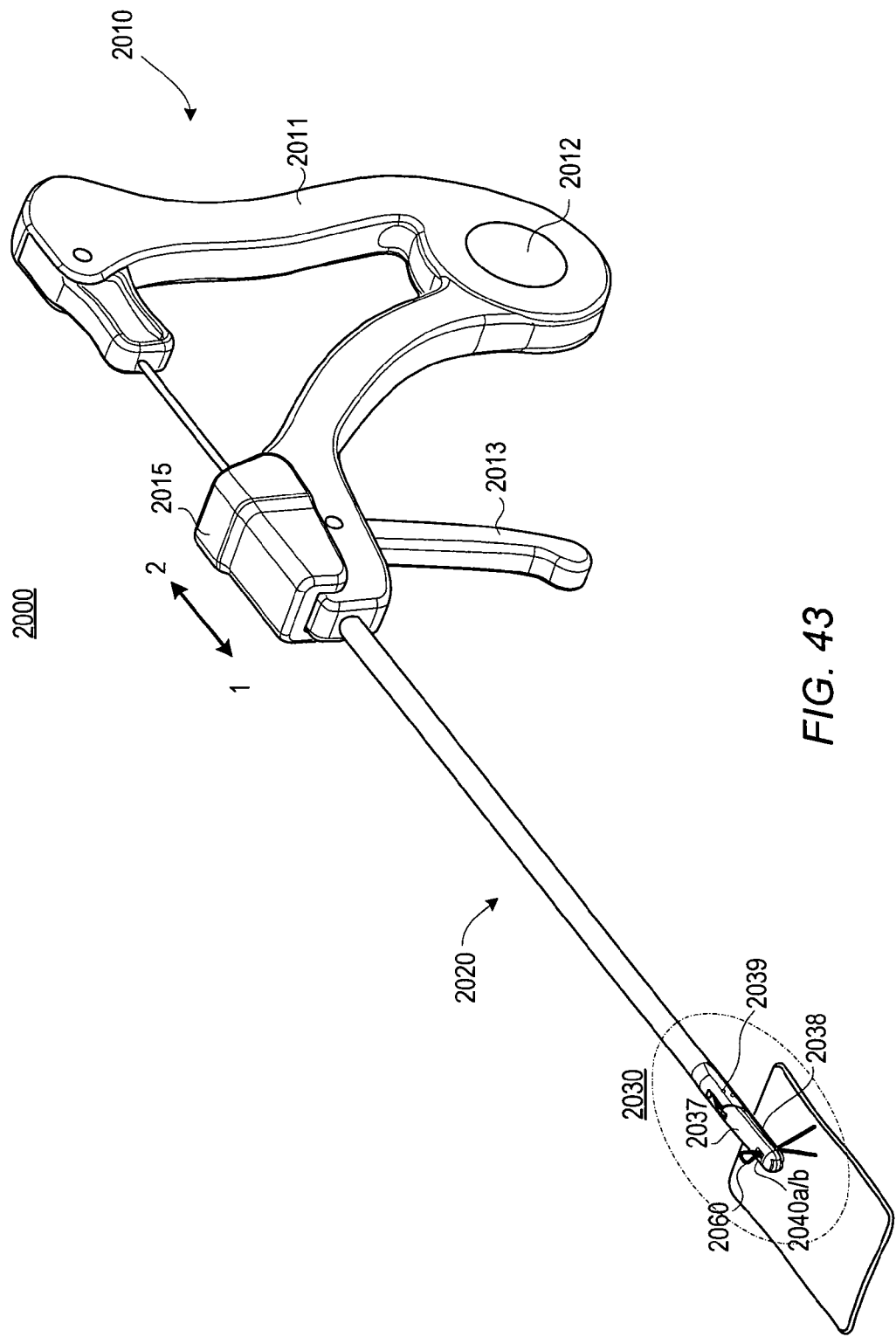
FIG. 43 is a schematic depiction of a suture passer device according to an embodiment.

In some embodiments, a bone anchor inserter system may include a suture passer device. Turning to FIG. 43, an embodiment of a suture passer 2000 is shown. Suture passer 2000 may include a proximal end 2010 having handle 2011 that is pivotable about joint 2012. Proximal end 2010 may further include grip 2012 coupled to at least a portion of the handle. Proximal end 2010 may be configured to allow a surgeon to operate the suture passer, including distal components thereof, during use. Likewise, grip 2013 may be configured to control one or more mechanisms located at the distal end of the suture passer when a surgeon compresses the grip during use. Proximal end 2010 may include a slidable engaging element 2015 coupled to at least a potion of handle 2011. In an embodiment, engaging element 2015 may be configured to slide along the longitudinal axis of the suture passer between a first position and a second position (shown by the double-headed arrow in FIG. 43). Engaging element 2015 may be operable coupled to one or more elements located distally to proximal end 2010 as discussed below. In an embodiment, positioning engaging element 2015 from the first position to the second position may allow the engagement of one or more distal elements of the suture passer.

In an embodiment, suture passer 2000 may include a rigid or semi-rigid elongated central portion 2020 extending distally from proximal end 2010. Central portion 2020 may be configured to allow the operable coupling of one or more elements of proximal end 2010 with one or more elements disposed at distal end 2030 of the suture passer.

In an embodiment, distal end 2030 may include a may include a tissue grasping means 2035. A tissue grasping means 2035 may be configured to reversibly grasp a tissue. In an embodiment, tissue-grasping means 2035 may include a lower jaw 2038 and an upper jaw 2037 rotatable coupled to the lower jaw through hinged connection 2012. Rotatable couple means 2012 may be configured to enable the reversible grasping of a tissue between the upper and lower jaws when a surgeon engages a controlling means (e.g., handle 2013) located at the proximal end. In an embodiment, upper jaw 2037 and lower jaw 2038 may each be configured to have at least one suture passage 2040 extending therethrough. Suture passage 2040 may be sized to allow passage of a suture segment and/or a suture loop 2060 through the passage.

Turning now to FIG. 44, a closer view of distal end 2030 of suture passer 2000 is shown. FIG. 44A shows tissue grasping means 2035 in a retracted state, where upper jaw 2037 is disengaged from lower jaw 2038. In this view, suture passage 2040a passing through upper jaw 2037 and suture passage 2040b passing through lower jaw 2038 can be seen.

Figure 44A:
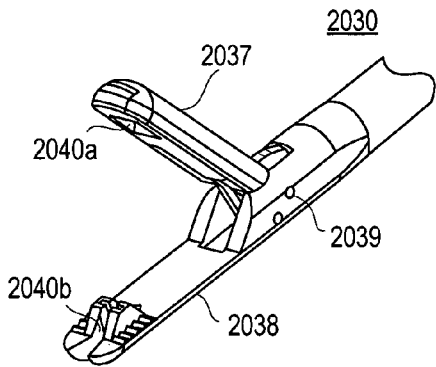
FIGS. 44A through 44E depict a sequence of steps to operate the distal end of the suture passer depicted in FIG. 43.
Figure 44B:
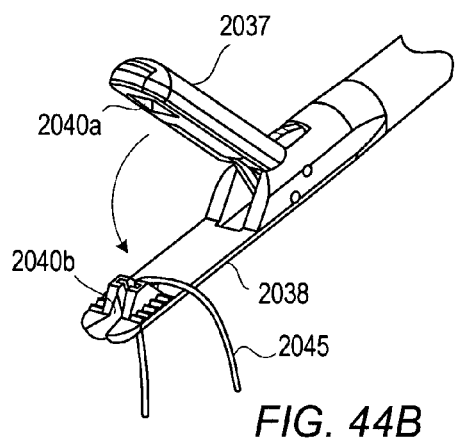
Figure 44C:
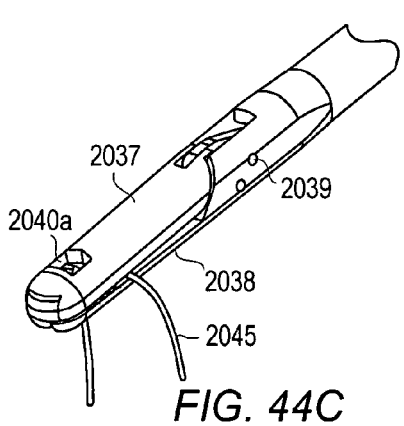

During operation, a suture length is passed though at least one of the distally located suture passages. Advantageously, the device may be configured such that the suture may be passed through the suture passage in either of the jaws. FIG. 44B shows an embodiment, wherein a suture 2045 is passed through suture passage 2040b through lower jaw 2038, although it will be recognized that the suture may also be passed through the a suture passage 2040a without departing from the sprit or scope of the presently described embodiments. Passage of the suture through suture passage 2040b occurs when upper jaw 2037 is still in a retracted state. Engagement of tissue grasping means 2035 may be operably controlled from one or more controlling mechanisms disposed at proximal end 2010 (not shown). Engagement of tissue grasping means 2035 moves upper jaw 2037 in the direction indicated by the curved arrow in FIG. 44B, and compresses suture 2045 between the upper and lower jaws.

Figure 44D:
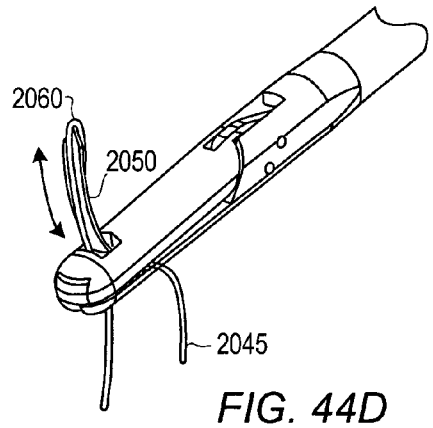
Figure 44E:
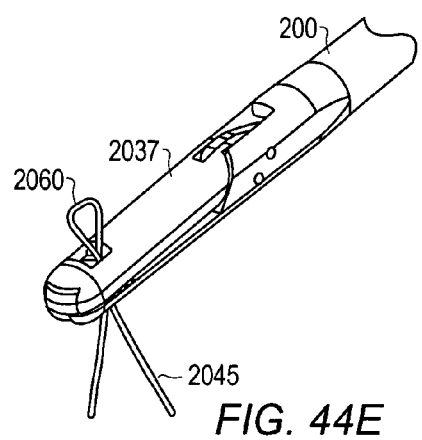

Proceeding to FIG. 44D, distal end 2030 may further include a reversibly extendable suture threader 2050. Suture threader 2050 may be made of a rigid or semi-rigid, resilient material. Suture threader 2050 may be configured to be reversibly extended in the directions indicated by the double-headed arrow in FIG. 44D when an extending mechanism controllable from proximal end 2010 is engaged. In an embodiment, suture threader 2050 may be configured such that, when extended, the distal portion thereof engages at least a portion of suture 2045 passing through the suture passage, and extends the engaged portion of suture 2045 though one of the suture passages 2040a/b to form suture loop 2060. Disengagement of suture threader 2050 allows the retraction thereof back though suture passage 2040a/b, and leaves suture loop 2060 protruding through the suture passage, as depicted schematically in FIG. 44E.

In an embodiment, suture passer 2000 may include a reversibly engageable mechanical means to retrieve the suture or suture loop after is passed though the suture passer. Engagement of the mechanical suture retrieval means during use may obviate the need for a separate device with which to retrieve the suture loop, thereby improving efficiency, maximizing working volume, and minimizing risk of contamination. In an embodiment, a mechanical suture retrieval means may include a suture capture element. Turning to FIG. 45, a top view of distal end 2030 with suture loop 2060 protruding from suture passage 2040a is shown in FIG. 45A. In an embodiment, suture capture element 2070 may be disposed at the distal portion of distal end 2030 and be moveably coupled thereto such that suture capture element 2070 may be moved along a longitudinal axis between a first retracted position 2070' shown in FIG. 45A and a second engaged position 2070" shown in FIG. 45D. Suture capture element 2070 may be operably coupled to engaging element 2015 so that manual movement of the engaging element in the distal element to first position 2015' shown in FIG. 45B positions suture capture element at retracted position 2070', and movement of the engaging element in the proximal direction to second position 2015" shown in FIG. 45C positions the suture capture element at engaged position 2070" shown in FIG. 45D. When engaged, suture loop 2060 may be compressed between edge 2071 of the suture capture element, and edge 2072 of suture passage 2040a/b allowing the facile retrieval of the suture and/or suture loop.

While preferred illustrative embodiments of the invention are described above, it will be apparent to one skilled in the art that various changes and modifications may be made therein without departing from the spirit and scope of the invention. The appended claims are intended to cover all such changes and modifications that fall within the true spirit and scope of the invention.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A bone anchor installer system comprising:
a handle portion;
a loading portion comprising a proximal end coupled to the handle portion and a distal end adapted to releasably couple to a bone anchor;
an anchor holder removably coupled to the distal end of the loading portion, the anchor holder comprising at least two portions, the at least two portions comprising a first portion releasably coupled to a second portion, and a cavity sized to accept the distal end of the loading portion and a bone anchor coupled thereto; and
a mechanism adapted to uncouple the first and second portions of the anchor holder from the loading portion while the distal end of the loading portion and the bone anchor are within the cavity.

2. The installer system of claim 1 comprising a tether releasably retaining a bone anchor to the distal end of the loading portion.

3. The installer system of claim 2 wherein the tether extends from the bone anchor to the proximal end of the loading portion.

4. The installer system of claim 2 wherein tension on the tether is variable.

5. The installer system of claim 2 wherein the tether is accessible near the proximal end of the loading portion.

6. The installer system of claim 1 comprising a cannula sized to deliver a bone anchor attached to the loading portion to a surgical site.

7. The installer system of claim 1 comprising a suture puller coupled to the anchor holder to engage a suture to a bone anchor.

8. The installer system of claim 1 comprising a suture puller engaged with the anchor holder and a bone anchor located in the cavity, the suture puller comprising;
a distal end configured to couple with one or more sutures; and
a proximal end configured to allow an operator to pull the suture puller through the anchor holder and a bone anchor to couple the suture to the bone anchor.

9. The install system of claim 8 wherein the suture puller is threaded through a two bar locking mechanism on the bone anchor.

10. The installer system of claim 8 wherein the distal end of the suture puller comprises a loop adapted to receive one or more sutures.

11. The installer system of claim 1 comprising a bone anchor coupled to the distal end of the loading portion.

12. The installer system of claim 1 comprising:
a bone anchor coupled to the distal end of the loading portion, wherein the bone anchor includes a two bar locking mechanism; and
at least one suture threaded through the two bar locking mechanism.

13. The installer of claim 12 wherein the suture is threaded between a first locking bar and the bone anchor from a side opposite a second locking bar, around the second locking bar on a side opposite the bone anchor, and back through a space between the first and second locking bars and the bone anchor.

14. A bone anchor installer system comprising:
a handle portion;
a loading portion coupled to the handle portion, the loading portion having a distal end adapted to releasably couple to a bone anchor;
an anchor holder removably coupled to the distal end of the loading portion, the anchor holder comprising:
a longitudinal axis;
a cavity extending substantially along the longitudinal axis, the cavity sized to accept the distal end of the loading portion and the bone anchor coupled thereto;
a first portion defining a first inner surface of the cavity; and
a second portion releasably coupled to the first portion, the second portion defining a second inner surface of the cavity, wherein the first inner surface is on one side of the bone anchor and the second inner surface is on another side of the bone anchor with respect to the longitudinal axis when the bone anchor is accepted in the cavity; and
a mechanism adapted to uncouple the first portion and second portions of the anchor holder from the loading portion.

15. A bone anchor installer system comprising:
a handle portion;
a loading portion coupled to the handle portion, the loading portion having a distal end adapted to releasably couple to a bone anchor; and
an anchor holder removably coupled to the distal end of the loading portion, the anchor holder comprising:
a longitudinal axis;
a cavity sized to accept the distal end of the loading portion and the bone anchor coupled thereto;
a first portion; and
a second portion releasably coupled to the first portion,
wherein the first portion and second portion surround the distal end of the loading portion and the bone anchor in a coupled configuration of the anchor holder, and wherein the first portion and the second portion are removable from the distal end of the loading portion and the bone anchor along an orthogonal direction with respect to the longitudinal axis in a released configuration of the anchor holder.

16. The bone anchor installer system of claim 1, wherein the mechanism is further adapted to uncouple the first and second portions of the anchor holder from the loading portion prior to installation of the bone anchor.

17. The bone anchor installer system of claim 14, wherein the first and second portions completely encircle the distal end of the loading portion.

18. The bone anchor installer system of claim 14, wherein the first and second portions completely encircle the bone anchor.

19. The bone anchor installer system of claim 15, wherein the first and second portions completely encircle the distal end of the loading portion.

20. The bone anchor installer system of claim 15, wherein the first and second portions completely encircle the bone anchor.

21. The bone anchor installer system of claim 14, wherein the first and second portions are separable halves of the anchor holder.

22. The bone anchor installer system of claim 15, wherein the first and second portions are separable halves of the anchor holder.

23. A bone anchor installer system, comprising:
a handle portion;
a loading portion comprising a proximal end coupled to the handle portion and a distal end releasably coupled to a bone anchor;
an anchor holder removably coupled to the distal end of the loading portion, the anchor holder comprising:
at least two portions, the at least two portions comprising a first portion releasably coupled to a second portion, and
a cavity sized to accept the distal end of the loading portion and the bone anchor coupled thereto;
a mechanism adapted to uncouple the first and second portions of the anchor holder from the loading portion while the distal end of the loading portion and the bone anchor are within the cavity;
a suture puller engaged with the anchor holder and the bone anchor located in the cavity, the suture puller comprising:
a first end configured to couple with one or more sutures; and
a second end configured to allow an operator to pull the suture puller through the anchor holder and the bone anchor, to couple the suture to the bone anchor prior to uncoupling of the first and second portions.

24. The bone anchor installer system of claim 23, wherein the first end and the second end both protrude laterally from the anchor holder.

25. The bone anchor installer system of claim 24, wherein the first end and the second end both protrude laterally on a same side of the anchor holder.

26. The bone anchor installer system of claim 24, wherein the suture puller extends into the cavity and through at least one aperture in the bone anchor.

27. The bone anchor installer system of claim 23, wherein the bone anchor comprises a first aperture and a second aperture, and wherein the suture puller extends into the cavity, through the first aperture, through the second aperture, and back out of the cavity.

28. The bone anchor installer system of claim 27, wherein the loading portion comprises a first slot and a second slot at the distal end, wherein the suture puller extends into the cavity, through the first slot, through the first aperture, through the second slot, back through the second slot, through the second aperture, back through the first slot, and back out of the cavity.

29. The bone anchor installer system of claim 28, wherein the anchor holder comprises a pin, wherein the pin at least partially spans the first and second portions prior to uncoupling of the first and second portions, and wherein the suture puller extends into the cavity, through the first slot, through the first aperture, through the second slot, around the pin, back through the second slot, through the second aperture, back through the first slot, and back out of the cavity.

* * * * *

UNITED STATES PATENT AND TRADEMARK OFFICE
CERTIFICATE OF CORRECTION

| | | |
|---|---|---|
| PATENT NO. | : 8,721,650 B2 | Page 1 of 1 |
| APPLICATION NO. | : 11/726736 | |
| DATED | : May 13, 2014 | |
| INVENTOR(S) | : Gary S. Fanton | |

It is certified that error appears in the above-identified patent and that said Letters Patent is hereby corrected as shown below:

In The Specification

In column 11 at line 56, Change "1118b" to --118b--.

In column 28 at lines 36-37, Change "allowingthe" to --allowing the--.

In column 29 at line 56, Change "further" to --farther--.

In column 30 at line 25, Change "75 lb." to --75lb.--.

In column 30 at line 27, Change "though" to --through--.

In column 30 at line 45, Change "though" to --through--.

In column 33 at line 5, Change "bole" to --bore--.

In column 34 at line 20, Change "potion" to --portion--.

In column 36 at line 25, Change "potion" to --portion--.

In column 36 at line 61, Change "though" to --through--.

In column 37 at line 1, Change "the a" to --the--.

In column 37 at line 29, Change "though" to --through--.

In The Claims

In column 38 at line 65, In Claim 9, change "install system" to --installer system--.

In column 39 at line 13, In Claim 13, change "installer" to --installer system--.

Signed and Sealed this
Seventh Day of April, 2015

Michelle K. Lee
*Director of the United States Patent and Trademark Office*